United States Patent [19]
Bloom et al.

[11] Patent Number: 6,070,761
[45] Date of Patent: Jun. 6, 2000

[54] VIAL LOADING METHOD AND APPARATUS FOR INTELLIGENT ADMIXTURE AND DELIVERY OF INTRAVENOUS DRUGS

[75] Inventors: Nicole D. Bloom, San Francisco, Calif.; Dean L. Kamen, Bedford; Richard Lanigan, Concord, both of N.H.; Charles M. Grinnell, Groton, Mass.; Kevin Grant, Manchester, N.H.

[73] Assignee: Deka Products Limited Partnership, Manchester, N.H.

[21] Appl. No.: 08/916,886

[22] Filed: Aug. 22, 1997

[51] Int. Cl.[7] ........................................................ B65B 3/00
[52] U.S. Cl. ............................. 222/81; 222/88; 222/325; 141/330; 141/367; 141/375
[58] Field of Search ............................... 222/81, 88, 162, 222/325; 141/329, 330, 367, 363, 364, 375

[56] References Cited

U.S. PATENT DOCUMENTS

| | | | |
|---|---|---|---|
| Re. 29,062 | 12/1976 | Olge | 128/214 C |
| D. 290,656 | 6/1987 | Kaleskas | D24/53 |
| 717,033 | 12/1902 | Schneider et al. | 141/372 |
| 827,926 | 8/1906 | Lavertine et al. | 222/325 |
| 1,576,214 | 3/1926 | Paskal | 141/372 |
| 1,657,782 | 1/1928 | Berg | 141/330 |
| 1,766,182 | 6/1930 | Markus | 141/330 |
| 1,811,572 | 6/1931 | Ailes | 222/325 |
| 2,138,844 | 12/1938 | Erb | 141/330 |
| 3,470,874 | 10/1969 | Accetta | 128/173.1 |
| 3,670,728 | 6/1972 | Dabney | 128/214 C |
| 3,848,112 | 11/1974 | Weichselbaum et al. | 235/61.7 |
| 3,853,158 | 12/1974 | Whitty | 141/330 |

(List continued on next page.)

FOREIGN PATENT DOCUMENTS

| | | |
|---|---|---|
| 0335378-A2 | 4/1989 | European Pat. Off. . |
| 2717919-A1 | 9/1995 | France . |
| 3605640-A1 | 8/1987 | Germany . |
| 82/00591 | 3/1982 | WIPO . |
| 87/07159 | 12/1987 | WIPO . |
| WO 94/08549 | 4/1994 | WIPO . |
| WO 94/12235 | 6/1994 | WIPO . |
| WO 95/29455 | 11/1995 | WIPO . |
| WO 96/13790 | 5/1996 | WIPO . |
| WO 96/40328 | 12/1996 | WIPO . |
| WO 97/04712 | 2/1997 | WIPO . |

OTHER PUBLICATIONS

Ogura et al., "Online Support Functions of Prescription Order System and Prescription Audit in an Integrated Hospital Information System," MED. INFORM. (1988), vol. 13, No. 3, 161–169.

Moliver et al., "Decision Support for Medical Treatment: A TPN Prescription System on a Central Hospital Computer," Proceedings of the 11th Annual Symposium on Computer Applications in Medical Care, Washington, D.C., USA, Nov. 1–4, 1987, 246–254.

(List continued on next page.)

Primary Examiner—J. Casimer Jacyna
Attorney, Agent, or Firm—Lyon & Lyon LLP

[57] ABSTRACT

The present invention is directed toward a vial-loading mechanism for a system that prepares and delivers one or more IV drugs to a patient. The vial-loading mechanism is used to load a vial onto a cassette spike and includes a vertical support member located adjacent to the spike. A holding assembly holds at least one vial. The holding assembly is mounted to the support member so as to be positionable between an upper position for loading a vial and a lower position for piercing the vial with a spike. The holding assembly has an arcuate-shaped holding member for holding the vial. A catch is provided with an engagement unit for securing the holding assembly in the lower position. This arrangement provides an easy way to add, retain, and remove vials from the system and protects the clinicians that do this from contacting the spikes and hurting themselves.

12 Claims, 50 Drawing Sheets

U.S. PATENT DOCUMENTS

| | | | |
|---|---|---|---|
| 3,921,196 | 11/1975 | Patterson | 235/61.11 D |
| 3,941,171 | 3/1976 | Olge | 141/309 |
| 4,114,144 | 9/1978 | Hyman | 340/632 |
| 4,164,320 | 8/1979 | Irazoqui et al. | 235/375 |
| 4,217,993 | 8/1980 | Jess et al. | 222/14 |
| 4,238,108 | 12/1980 | Muetterties | 251/6 |
| 4,308,866 | 1/1982 | Jelliffe et al. | 128/214 |
| 4,321,461 | 3/1982 | Walter, Jr. et al. | 235/92 |
| 4,410,321 | 10/1983 | Pearson et al. | 604/56 |
| 4,411,662 | 10/1983 | Pearson | 604/411 |
| 4,424,056 | 1/1984 | Urquhart et al. | 604/56 |
| 4,432,755 | 2/1984 | Pearson | 604/56 |
| 4,432,756 | 2/1984 | Urquhart et al. | 604/80 |
| 4,434,820 | 3/1984 | Glass | 141/375 |
| 4,439,183 | 3/1984 | Theeuwes | 604/85 |
| 4,458,733 | 7/1984 | Lyons | 141/1 |
| 4,465,471 | 8/1984 | Harris et al. | 604/56 |
| 4,474,574 | 10/1984 | Wolfe et al. | 604/85 |
| 4,476,381 | 10/1984 | Rubin | 235/375 |
| 4,479,793 | 10/1984 | Urquhart et al. | 604/85 |
| 4,479,794 | 10/1984 | Urquhart et al. | 604/85 |
| 4,498,604 | 2/1985 | Mackal | 141/329 |
| 4,525,162 | 6/1985 | Urquhart et al. | 604/56 |
| 4,534,757 | 8/1985 | Geller | 604/85 |
| 4,534,758 | 8/1985 | Akers et al. | 604/85 |
| 4,548,599 | 10/1985 | Urquhart et al. | 604/85 |
| 4,570,639 | 2/1986 | Miodownik | 128/718 |
| 4,573,967 | 3/1986 | Hargrove et al. | 604/56 |
| 4,573,994 | 3/1986 | Fischell et al. | |
| 4,576,211 | 3/1986 | Valentini et al. | 141/329 |
| 4,581,014 | 4/1986 | Millerd et al. | 604/80 |
| 4,589,867 | 5/1986 | Isreal | 604/85 |
| 4,623,334 | 11/1986 | Riddell | 604/85 |
| 4,624,661 | 11/1986 | Arimond | 604/151 |
| 4,636,950 | 1/1987 | Caswell et al. | 364/403 |
| 4,658,244 | 4/1987 | Meijer | 340/632 |
| 4,673,927 | 6/1987 | Cianciavicchia et al. | 340/621 |
| 4,696,671 | 9/1987 | Epstein et al. | 604/67 |
| 4,714,462 | 12/1987 | DiDomenico | 604/67 |
| 4,721,138 | 1/1988 | Simonazzi | 141/150 |
| 4,762,518 | 8/1988 | Kreinick | 604/245 |
| 4,764,166 | 8/1988 | Spani | 604/65 |
| 4,778,451 | 10/1988 | Kamen | 604/67 |
| 4,784,643 | 11/1988 | Siretchi et al. | 604/122 |
| 4,786,800 | 11/1988 | Kamen | 250/222.1 |
| 4,804,366 | 2/1989 | Zdeb et al. | 604/85 |
| 4,804,380 | 2/1989 | Lassen et al. | 604/385.1 |
| 4,810,243 | 3/1989 | Howson | 604/31 |
| 4,816,019 | 3/1989 | Kamen | 604/65 |
| 4,818,489 | 4/1989 | Gonner et al. | 141/329 |
| 4,826,482 | 5/1989 | Kamen | 604/67 |
| 4,828,545 | 5/1989 | Epstein et al. | 604/66 |
| 4,829,448 | 5/1989 | Balding et al. | 364/509 |
| 4,831,562 | 5/1989 | McIntosh et al. | 364/569 |
| 4,832,690 | 5/1989 | Kuu | 604/85 |
| 4,835,372 | 5/1989 | Gombrich et al. | 235/375 |
| 4,839,806 | 6/1989 | Goldfischer et al. | 364/413.02 |
| 4,842,028 | 6/1989 | Kaufman et al. | 141/330 |
| 4,847,764 | 7/1989 | Halvorson | 364/413.02 |
| 4,848,872 | 7/1989 | Shigematsu et al. | 350/96.29 |
| 4,850,972 | 7/1989 | Schulman et al. | 604/151 |
| 4,850,978 | 7/1989 | Dudar et al. | 604/201 |
| 4,853,521 | 8/1989 | Claeys et al. | 235/375 |
| 4,856,339 | 8/1989 | Williams | 73/714 |
| 4,857,713 | 8/1989 | Brown | 235/375 |
| 4,857,716 | 8/1989 | Gombrich et al. | 235/462 |
| 4,865,584 | 9/1989 | Epstein et al. | 607/67 |
| 4,874,366 | 10/1989 | Zdeb et al. | 604/56 |
| 4,898,578 | 2/1990 | Rubalcaba, Jr. | |
| 4,916,441 | 4/1990 | Gombrich et al. | 340/712 |
| 4,925,444 | 5/1990 | Orkin et al. | 604/80 |
| 4,936,829 | 6/1990 | Zdeb et al. | 604/85 |
| 4,950,235 | 8/1990 | Slate et al. | 604/65 |
| 4,959,050 | 9/1990 | Bobo, Jr. | 604/49 |
| 4,976,162 | 12/1990 | Kamen | 73/865.9 |
| 4,978,335 | 12/1990 | Arthur, III | 604/67 |
| 5,006,050 | 4/1991 | Cooke et al. | |
| 5,006,110 | 4/1991 | Garrison et al. | 604/65 |
| 5,006,699 | 4/1991 | Felner et al. | 235/472 |
| 5,024,657 | 6/1991 | Needham et al. | 604/85 |
| 5,036,852 | 8/1991 | Leishman | 128/630 |
| 5,041,086 | 8/1991 | Koenig et al. | 604/65 |
| 5,059,171 | 10/1991 | Bridge et al. | 604/67 |
| 5,062,774 | 11/1991 | Kramer et al. | |
| 5,064,412 | 11/1991 | Henke et al. | 604/65 |
| 5,072,383 | 12/1991 | Brimm et al. | 364/413.02 |
| 5,074,844 | 12/1991 | Zdeb et al. | 604/83 |
| 5,078,683 | 1/1992 | Sancoff et al. | 604/67 |
| 5,088,515 | 2/1992 | Kamen | 137/15 |
| 5,088,981 | 2/1992 | Howson et al. | 604/31 |
| 5,100,380 | 3/1992 | Epstein et al. | 604/67 |
| 5,102,392 | 4/1992 | Sakai et al. | 604/122 |
| 5,103,211 | 4/1992 | Daoud et al. | 340/608 |
| 5,116,316 | 5/1992 | Sertic et al. | 604/83 |
| 5,123,275 | 6/1992 | Daoud et al. | 73/19.03 |
| 5,127,618 | 7/1992 | Page et al. | 222/81 |
| 5,153,416 | 10/1992 | Neeley | 235/375 |
| 5,153,827 | 10/1992 | Coutre et al. | 364/413.02 |
| 5,163,585 | 11/1992 | Campbell | 141/329 |
| 5,176,631 | 1/1993 | Koenig | 604/65 |
| 5,177,993 | 1/1993 | Beckman et al. | 73/19.03 |
| 5,178,182 | 1/1993 | Kamen | 137/454.2 |
| 5,193,990 | 3/1993 | Kamen et al. | 417/474 |
| 5,203,385 | 4/1993 | Waber | 141/69 |
| 5,207,642 | 5/1993 | Orkin et al. | 604/65 |
| 5,211,201 | 5/1993 | Kamen et al. | 137/1 |
| 5,241,985 | 9/1993 | Faust et al. | 137/505.13 |
| 5,256,157 | 10/1993 | Samiotes et al. | 604/246 |
| 5,265,010 | 11/1993 | Evans-Paganelli et al. | 364/413.02 |
| 5,267,174 | 11/1993 | Kaufman et al. | 364/479 |
| 5,304,126 | 4/1994 | Epstein et al. | 604/67 |
| 5,316,053 | 5/1994 | Waber | 141/1 |
| 5,317,506 | 5/1994 | Coutre et al. | 364/413.02 |
| 5,325,478 | 6/1994 | Shelton et al. | |
| 5,329,976 | 7/1994 | Haber et al. | 141/329 |
| 5,341,854 | 8/1994 | Zezulka et al. | 141/329 |
| 5,349,852 | 9/1994 | Kamen et al. | 73/149 |
| 5,353,837 | 10/1994 | Faust | 137/624.18 |
| 5,364,371 | 11/1994 | Kamen | 604/251 |
| 5,367,555 | 11/1994 | Isoyama | 379/38 |
| 5,374,813 | 12/1994 | Shipp | 235/375 |
| 5,378,231 | 1/1995 | Johnson et al. | 604/67 |
| 5,382,232 | 1/1995 | Hague et al. | 604/65 |
| 5,385,540 | 1/1995 | Abbott et al. | |
| 5,390,238 | 2/1995 | Kirk et al. | 379/93 |
| 5,395,321 | 3/1995 | Kawahara et al. | |
| 5,401,059 | 3/1995 | Ferrario | |
| 5,401,342 | 3/1995 | Vincent et al. | 156/73.1 |
| 5,416,695 | 5/1995 | Stutman et al. | 364/413.02 |
| 5,429,602 | 7/1995 | Hauser | 604/65 |
| 5,431,627 | 7/1995 | Pastrone et al. | 604/65 |
| 5,464,392 | 11/1995 | Epstein et al. | 604/67 |
| 5,494,083 | 2/1996 | Elmore | 141/330 |
| 5,494,087 | 2/1996 | Pitelka et al. | 141/375 |
| 5,496,273 | 3/1996 | Pastribe et al. | |
| 5,526,844 | 6/1996 | Kamen et al. | 137/614.11 |
| 5,529,097 | 6/1996 | Campbell | 141/330 |
| 5,533,389 | 7/1996 | Kamen et al. | 73/149 |
| 5,536,084 | 7/1996 | Curtis et al. | 364/413.01 |
| 5,547,470 | 8/1996 | Johnson et al. | 604/67 |
| 5,555,741 | 9/1996 | Oakley | 222/81 |
| 5,555,920 | 9/1996 | Godolphin et al. | 141/329 |

| | | | |
|---|---|---|---|
| 5,594,786 | 1/1997 | Chaco et al. ............................. | 379/93 |
| 5,616,124 | 4/1997 | Hague et al. . | |
| 5,643,212 | 7/1997 | Coutré et al. . | |
| 5,651,775 | 7/1997 | Walker et al. ......................... | 604/207 |
| 5,681,285 | 10/1997 | Ford et al. . | |
| 5,685,844 | 11/1997 | Marttila . | |
| 5,758,095 | 5/1998 | Albaum et al. . | |
| 5,758,096 | 5/1998 | Barsky et al. . | |
| 5,764,034 | 6/1998 | Bowman et al. . | |
| 5,766,155 | 6/1998 | Hyman et al. . | |
| 5,772,635 | 6/1998 | Dastur et al. . | |
| 5,781,442 | 7/1998 | Engleson et al. .................. | 364/478.02 |
| 5,791,880 | 8/1998 | Wilson . | |

OTHER PUBLICATIONS

Ogura et al., "On–Line Prescription Order and Prescription Support in an Integrated Hospital Informaiton System," MED. INFORM. (1985), vol. 10, No. 4, 287–299.

Edmond et al., "Prevention of Mis–Prescribing in the Elderly: A Potential Use for Micro–Computers," Proceedings of the 8th Annual Symposium on Computer Applications in Medical Care, Washington, D.C., USA, Nov. 4–7, 1984, 357–360.

Bates et al., "The Costs of Adverse Drug Events in Hospitalized Patients" JAMA 277(4) 307–311 (1997).

Belkin, "How Can We Save the Next Victim?" N.Y. Times Magazine 28–33 (1997).

Classen et al., "Adverse Drug Events in Hospitalized Patients" JAMA 277(4) 301–306 (1997).

Cohen et al., "Confusing & Dangerous Medical Abbreviations that Should Never Be Used" The Pennsylvania Nurse.

Cohen et al., "Minimizing Look Alike Generic Mix–ups" American Pharmacy NS34 (3) (1994).

Cohen et al., "Pharmacy Label Mix–Ups" American Pharmacy NS32 (1) 26–27 (1992).

Davis et al., "More Look–Alike and Sound–Alike Errors" American Pharmacy NS33(10) 32 (1993).

Flynn et al., "Observational Study of Accuracy in Compounding I.V. Admixtures at Five Hospitals" Am. J. Health–Syst Pharm. 54, 904–912 (1997).

Leape, et al., "Error in Medicine" JAMA 272(23) 1851–1857 (1994).

Schneider et al., "Cost of Medication–Related Problems at a University Hospital" Am. J. Helath–Syst. Pharm. 52, 2415–2418 (1995).

"Medication Errors: A Special Report. New Initiatives are Launched as Problems Worsen" Drug Utilization Review 14(3) 37–56 (1998).

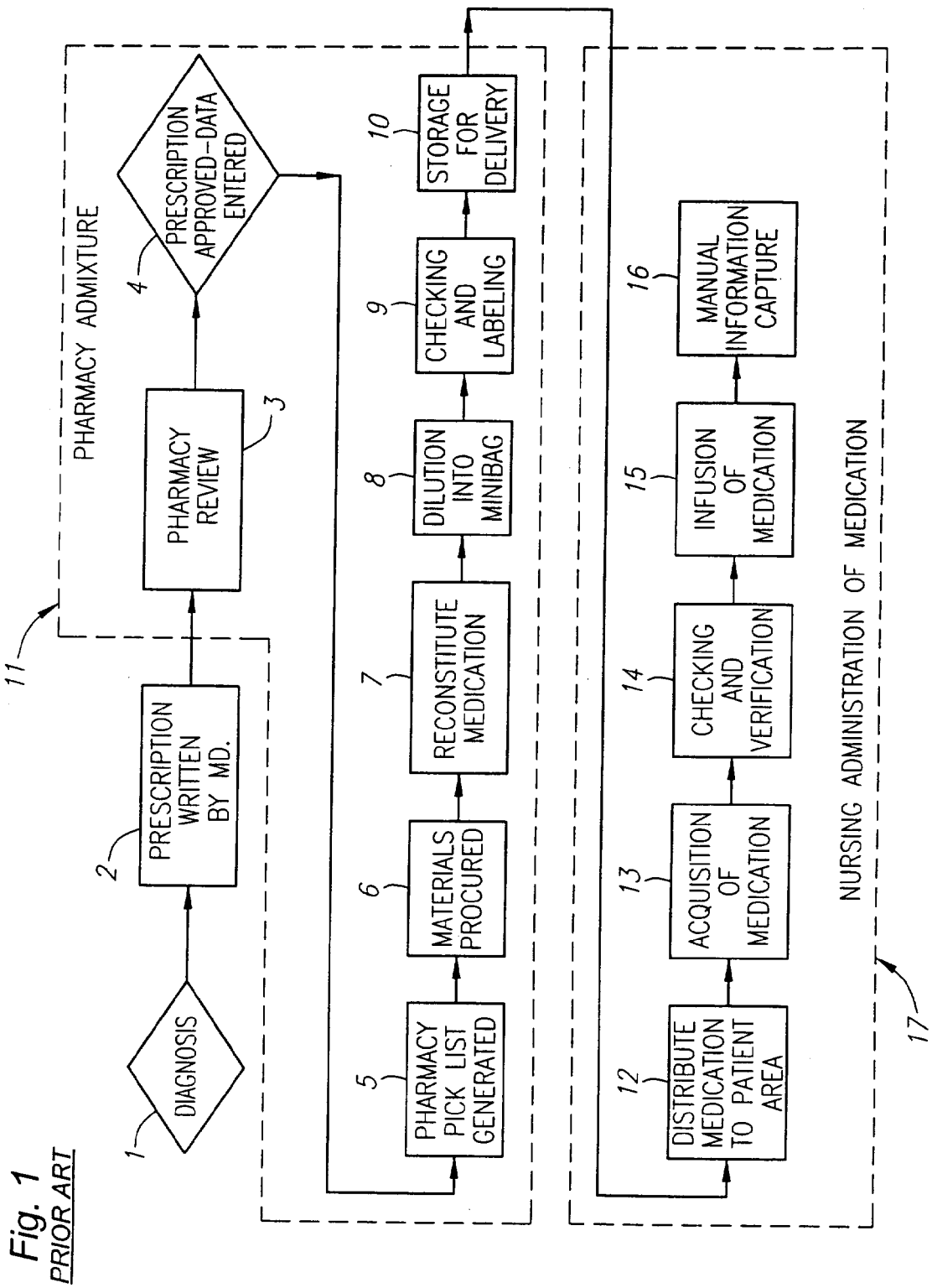

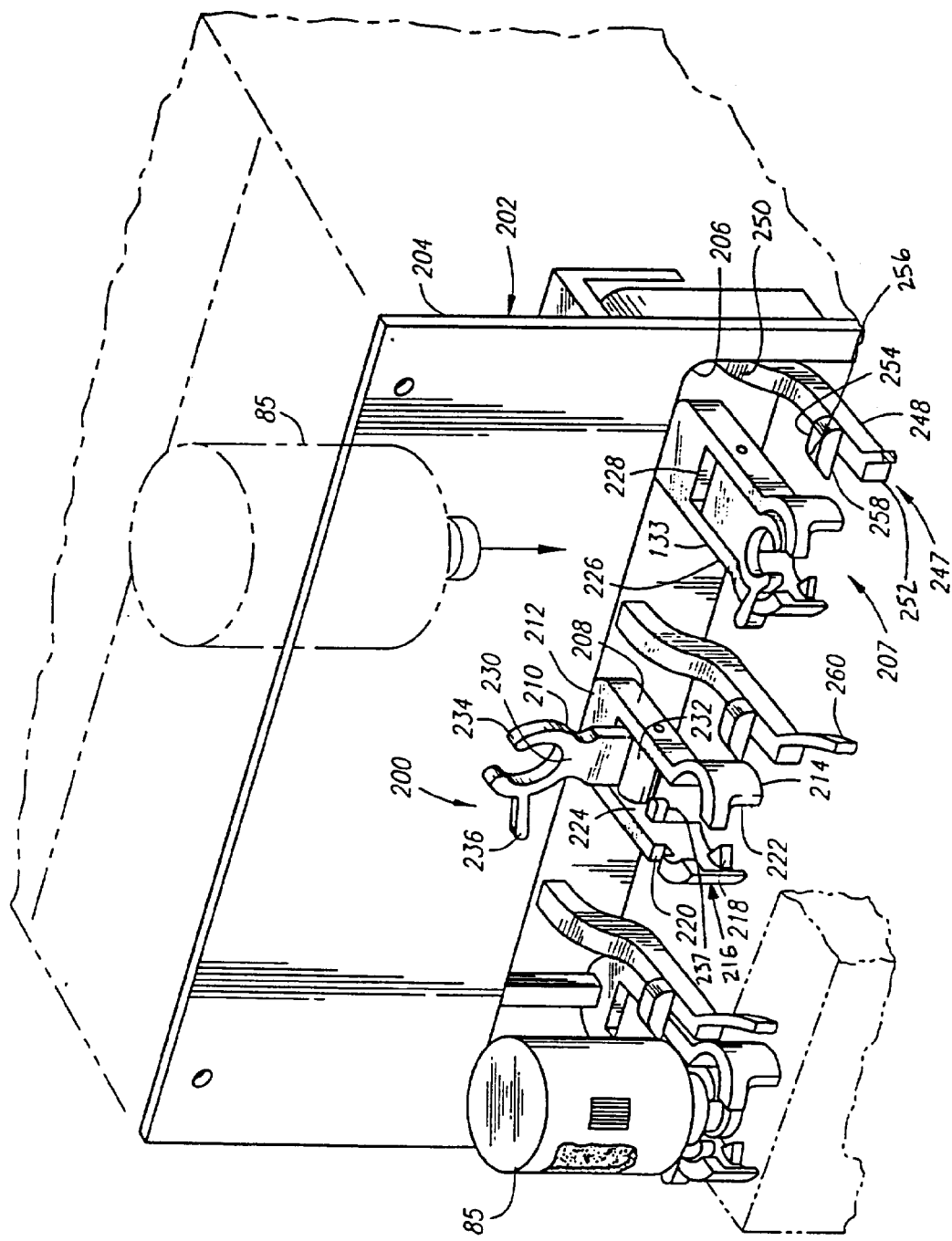

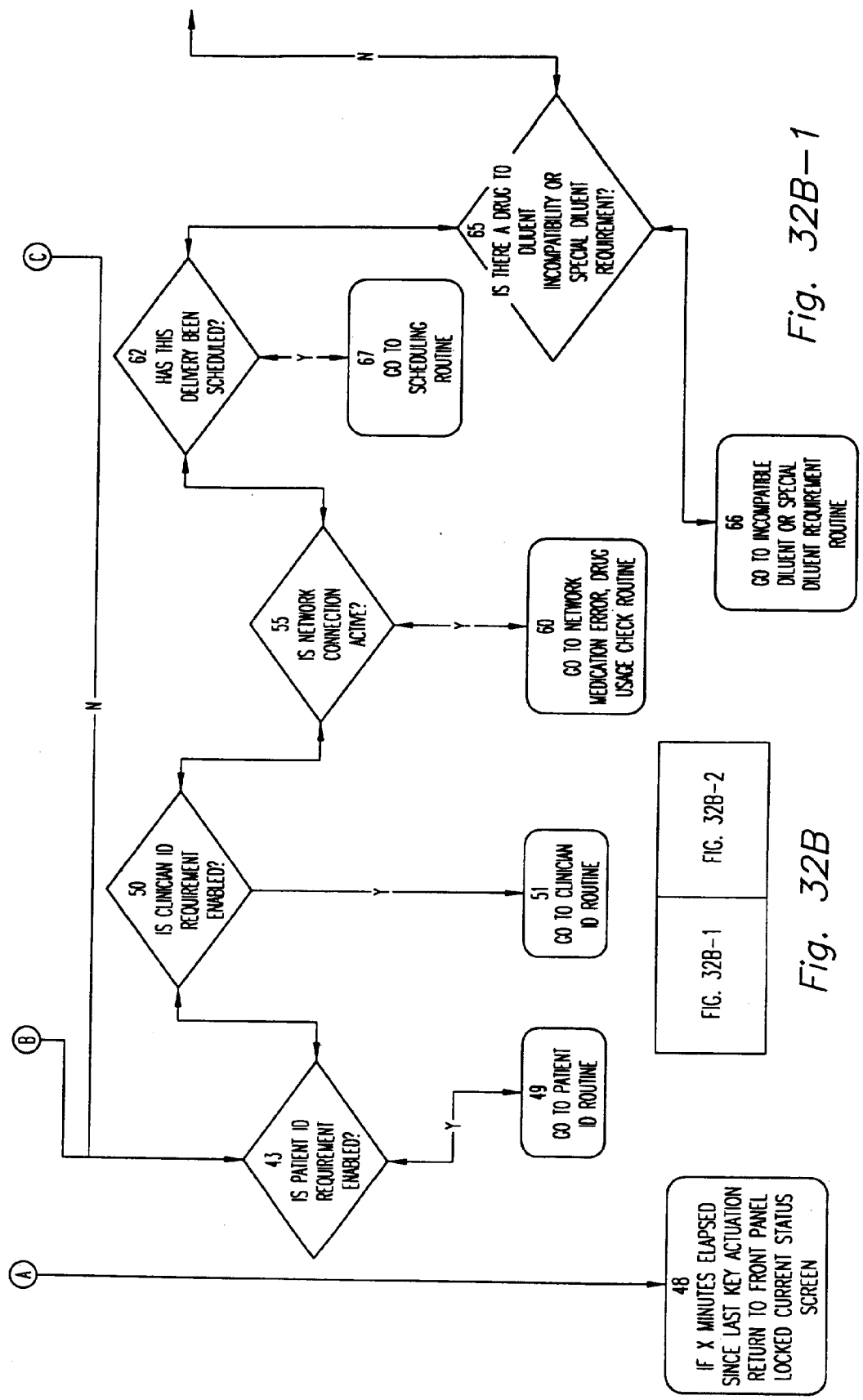

VIAL LOADING METHOD AND APPARATUS FOR INTELLIGENT ADMIXTURE AND DELIVERY OF INTRAVENOUS DRUGS

RELATED APPLICATIONS

The present application is related to U.S. patent applications Ser. No. 08/918,492, titled "Health Care System and Method for Physician Order Entry," Ser. No. 08/916,889, titled "Automated Health Care System," and Ser. No. 08/916,887, titled "System and Method for Intelligent Admixture and Delivery of Medications," each of which are filed concurrently herewith and each of which are incorporated herein by reference as if reproduced in full below.

BACKGROUND OF THE INVENTION

This invention relates to methods and apparatus for intelligent admixture and delivery of intravenous drugs and for tracking and pre-delivery and post-delivery verification and recording of drug dosages however administered to patients.

Although physicians, pharmacists, nurses, care givers and other health-care providers strive for error-free patient care, because of the complexity of modern medicine and the trend to minimize costs of delivery resulting in fewer and lower paid nurses, pharmacists, technicians and hospital employees, they frequently fall short of the mark. Indeed, the frequency of injuries from improperly formulated or delivered medication, (sometimes referred to as "adverse drug events") is rapidly increasing. Reduction of such injuries is an urgent need in light of the following statistic: researchers estimate that 180,000 people die in the U.S. annually from adverse drug events. That number of deaths is the equivalent of 3 jumbo jet crashes every 2 days. The severity of the problem is compounded by a general lack of awareness, amongst both clinicians and the general public, that a problem even exists. L. Leape, *Error in Medicine Journal of the American Medical Association,* Dec. 21, 1994, Vol. 272 No. 23, p. 1851.

Many of these adverse drug events result from errors in administering intravenous (IV) therapy. During any type of extensive hospitalization, a patient typically will receive some form of intravenous therapy because it is a fast and efficient route for the delivery of needed fluids and medications to a patient. The IV thus serves as the preferred transport vehicle for the intermittent delivery of a drug.

There are at least six basic classes of IV drugs: total parenteral nutrition (TPN); biotechnology (growth hormone for example); pain medication; continuous critical care medications; chemotherapy; and intermittents. Intermittent IV drugs are typically delivered in 4–6 doses spread out over a given period, such as a day, although other dosing intervals can be encountered.

Intermittent IV drugs can include, but are not limited to, antibiotics, antiemetics, H2 antagonists, steroids, and diuretics. IV drugs are typically prepared by the pharmacy or the manufacturer. Intermittent IV drugs represent one of the largest segments of medications delivered in a hospital.

For ease of use, manufacturers of intermittent IV drugs typically package the drugs into vials such as single-dose vials, multiple-dose vials and custom-dose vials. A single-dose vial is defined as a vial whose entire contents is acceptable or intended for use as a single dose to a patient. A multiple dose-vial is defined as a vial containing several doses of a drug. A custom dose vial is defined as a vial containing an amount of drug that is not prepackaged in a single or multiple dose "unit of use" configuration. The custom-dose vial can be used where a patient requires more or less than the contents of a single vial. Custom dosing can dictated by factors such as, for example, the patient's body weight, the patient's body surface area, lab results, and other factors.

Although clinicians may administer intermittent IV drugs quite often, the single- or multiple-dose vial configuration is typically not suitable for immediate intravenous delivery. This is because such drugs are normally packaged in a powdered, lyophilized or concentrated liquid form. Therefore, these drugs require conversion into a form more suitable for intravenous delivery. This conversion of intermittent IV drugs into a form suitable for intravenous delivery is known as the IV admixture process or simply admixture.

The admixture process normally includes a reconstitution step (if the medication is powdered or lyophilized, for example) and a dilution step. A pharmacist or technician ordinarily performs the admixture process after receipt of the prescription. This procedure is labor intensive and costly as well as fraught with potential error. Cohen M R, Davis N M. *Medication Errors: Causes and Prevention,* 1981. Schneider P J, Gift M G. *Cost of medication-related problems at a university hospital. Am J Health-Syst Pharm.* 1995; 52:2415–18. Belkin, *Who's to Blame? It's the Wrong Question.* N.Y. Times Magazine 1997, p 28–

Reconstitution, in the case of a lyophilized or powdered drug, involves the pharmacist or technician injecting a small amount of sterile water or other agent into the drug vial and agitating the vial to thoroughly dissolve the drug. Repetition of this procedure under aseptic conditions is difficult. Additionally, constant exposure of the technician to drugs, many of which are toxic in concentrated form, represents a hazard to the technician's health.

After reconstitution, a few of these drugs are now properly prepared for intravenous delivery. However, many drugs, after reconstitution, are too highly concentrated for immediate intravenous delivery. Such a concentrated solution could irritate or injure sensitive venous tissue. Thus, for most drugs, whether reconstituted or already available in concentrated liquid form, they must typically be diluted to prevent vein or tissue injury.

Dilution can be performed using a number of different techniques. One such technique is carried out by reinserting a syringe into the vial containing the reconstituted drug and withdrawing the appropriate amount of drug into the syringe. The contents of the syringe are then injected into a container holding a larger volume of solution commonly termed "diluent." The amount of dilution is a function of the characteristics of the drug, dosage, concentration, and can also be based on a patient's weight or body surface area, as well as other factors. The dilution volume of a drug can range from 0 ml up to a liter, or higher.

One leading method of dilution involves injecting the contents of the syringe containing reconstituted medication into a flexible plastic bag sometimes known as a minibag. The minibag is a single use, sterile package containing an appropriate amount (e.g., 50- or 100- ml's) of diluent. The drug is typically added to the container through an injection port on the minibag.

After the drug has been reconstituted and/or diluted, the pharmacist or technician affixes a preprinted patient-specific label to the bag. A pharmacist verifies the work and signs off on the label. The prepared minibag is then placed into refrigerated storage until delivery to the patient's location.

Despite the verification made by the pharmacist, given the number of IV drugs required by a typical hospital daily, prescription, admixture and delivery errors can still arise. Errors can include, for example: improperly mixed drugs, dosages delivered too early, too late or not all, incorrect dosages ordered by the physician, lost tracking and billing, and costly drug waste. Indeed, a recent report notes that the observed error for compounding I.V. admixtures was 9%. Flynn et al., *Observational Study of Accuracy in Compounding I.V. Admixtures at Five Hospitals, American Journal of Health Systems Pharmacia,* Vol. 54, Apr. 15, 1997, p. 904. Cohen M R, Davis N M. *Confusing and dangerous medical abbreviations that should never be used. Penn Nurse.*1991; 46(5):4–5. Cohen M R, Davis N M. *Pharmacy label mix-ups. Am Pharm.* 1992; NS32(1):26–7. Cohen M R, Davis N M. *Minimizing look-alike generic mix-ups. Am Pharm.* 1994; NS34(3):22–3. Cohen M R, Davis N M. *More look-alike and sound-alike errors. Am Pharm.* 1993; NS33(10) :32. An incorrect drug delivery can result in increased patient stays and, in some cases, serious injury or death. Studies indicate the average hospital spends approximately $2.8 million annually due to hospital stays extended because of preventable medication errors. Bates D W, *The Cost of Adverse Drug Events in Hospitalized Patients, JAMA* Jan. 22/29, 1997; Vol.277 No.4, 307–311. The national cost of these extended stays is estimated to exceed $4.2 billion annually. Classen D C, *Adverse Drug Events in Hospitalized Patients, JAMA* Jan. 22/29, 1997; Vol.277 No.4, 301–306.

In addition to being labor intensive and error-prone, the admixture procedure just described is also wasteful. Often, the reconstituted and diluted drug has a short shelf life. Even with refrigeration, the solution should be discarded after its shelf life has expired, often within a few days after the admixture process. Thus, if a batch is prepared and subsequently not needed, it will likely be wasted.

Furthermore, the use of minibags can lead to fluid overloading of the patient, particularly when multiple drugs are delivered to the patient intravenously. Because multiple drugs usually cannot be diluted simultaneously within the same minibag due to incompatibility potentials, each drug is diluted in its own minibag. This compounds the fluid overloading problem.

Alternatives to the labor-intensive IV admixture process just described have undesirable properties as well. Convenience packaging systems represent an alternative falling into two major categories. The first is premix or frozen premix which is a manufacturer prepackaged drug that is stable when diluted or when diluted and frozen. This method still suffers from the fluid overloading problem discussed earlier. Also, even though the drug stability is extended, there is still a limited shelf life. Additionally, this method suffers from the fact that manufacturers form strategic alliances with specific pharmaceutical companies and package that company's "brand name" drug with their minibag, charging a premium in the process. This prevents a hospital from using the cheaper generic form of the drug should the use of a premixed minibag be desirable.

A second alternative are minibags with vial adapters. A unit dose vial is attached to the minibag's vial adapter and the vial adapter's seal is then broken. The nurse reconstitutes and simultaneously dilutes the drug by moving fluid from the minibag into the vial. This category of minibags suffers from high cost, reduced ability to utilize generic drug substitutes, fluid overloading and the potential for drug waste. In addition, because nurses are not trained as pharmacists, the potential for errors are compounded when the pharmacy does not control the admixture process and nurses perform the so-called "mix and match" on the floor of the hospital.

Referring now to FIG. 1, we illustrate the multiple labor intensive and costly steps which must be carried out for the prior art manual IV admixture process. After a diagnosis 1, an order is written by the medical doctor 2. A pharmacist reviews the order 3, and approves and enters the prescription date 4. Prior to procuring the necessary materials 6, the pharmacist generates a pharmacy pick list of the required items 5. Typically a pharmacy technician then reconstitutes the drug 7 and dilutes the reconstituted medication into a minibag or other container 8. Then the pharmacist checks the work of the technician, initials and places a label on the minibag 9 before the minibag is stored for delivery 10. Steps 3 through 10 represent the pharmacy admixture process 11.

The minibags are thereafter distributed for delivery to the patient. Typically, the minibags are delivered to nursing stations in the general patient area 12 of the hospital. The nurse or other clinician reads the patient's prescription and acquires the medication 13 from the administration station. The clinician checks and verifies that particular medications are correlated with particular patients as per the prescription 14. The medications are then infused into the patient 15. The final step is the logging of the dose delivery and time, denoted as "manual information capture" 16. Steps 12 through 16 represent the administration of medication process 17.

In a effort to avoid the problems associated with the labor-intensive prior art IV admixture process, machine-aided reconstitution systems have been implemented. For example, various embodiments of a reconstitution and delivery system are disclosed in U.S. Pat. No. 4,410,321; U.S. Pat. No. 4,411,662; U.S. Pat. No. 4,432,755; and U.S. Pat. No. 4,458,733. The systems disclosed by these patents, however, require that a number of operations be manually performed by the operator before infusion of the reconstituted medication can be performed. A automated system for reconstituting a drug and delivering the drug intravenously is disclosed in U.S. Pat. No. 5,116,316. Among other potential shortcomings, none of these conventional systems address the problem of preventing medication errors by verifying patient's prescription and drug dosage in the crucial gap between the preparation of the drug through the admixture process and its administration and delivery to a patient.

Whether a drug is manually reconstituted and/or diluted through a manual admixture process or by machine as described in the above patents, the prepared IV drug is delivered into the veins of the patient at bedside. One conventional technique for delivery of the prepared IV drug is for a clinician to use a syringe and simply inject the prepared drug directly into a vein. However, to prevent vein irritation, in some instances it is necessary for the clinician to take several minutes to slowly inject the contents of the syringe into the vein. Moreover, many drugs require larger dilution volumes and longer delivery times than can be practically provided for by manual use of a syringe.

Another conventional technique for delivery of a prepared IV drug is through the use of a syringe pump. For such pumps, a pharmacist selects the appropriate size syringe, fills it, applies a label, attaches a specialized IV set, and delivers this to the clinician. The clinician loads the syringe into a syringe pump and starts the system. The syringe pump delivery system suffers from the costs associated with the labor required by the pharmacist in preparing the syringe and also does not have verification and recording features.

One of the most popular conventional mechanized delivery systems is the peristaltic infusion pump which operates by squeezing the delivery line to force the prepared drug into a vein of the patient. Such a delivery system is illustrated in FIG. 2. The system 32 includes three bags 36, 38, and 39, and a bottle or hard containers 40, each of which contains a fluid to be delivered to the patient. The containers are coupled by flexible fluid flow conduits or tubes 42, 44, 46, and 48, the end of which are coupled to catheters or similar devices for delivering fluid to the patient. Each of the flow lines 42 and 44 includes a conventional peristaltic infusion pump 50 which may be adjusted to deliver a specific volumetric flow to the patient.

Peristaltic pumps exert a great deal of force on the IV line to effectuate pumping. After repeated squeezing, the line loses its round shape, becoming oblong from the pinching force of the peristaltic pump. Such a misshapen line may restrict flow. Thus some peristaltic pumps cannot deliver precise amounts of fluid due to this line distortion phenomenon. Finally, these pumps cannot control air within the line. Although these pumps may have air-in-line sensors at the output of the pump, these pumps cannot detect bubbles at points upstream of the pump outlet and circulate them in a way so as to avoid air being pumped into the pump outlet altogether. The resulting air bubble alarms are a constant nuisance for nursing staff, especially considering that most of the detected bubbles are medically insignificant.

Finally, hospital information systems are frequently less than adequate. Because pharmacists are overworked, they make mistakes and approve orders which they should not have. For example, they may approve: a prescription for a patient with known allergies to the prescribed drug; a prescription to a patient already receiving a different drug which is incompatible with the additional prescribed drug; a drug inappropriate to the patient's diagnosis, an inappropriate amount of a drug when lab values indicate new dosage levels. These mistakes are created by a lack of an integrated information system.

Thus, there is a need for a drug delivery system, which will: automatically reconstitute and dilute medications; is capable of delivering precise amounts of fluids into a patient; can detect air bubbles and recirculate them before they are pumped outside of the pump outlet; can provide a bedside verification that the patient is receiving the correct drug (whether oral, IV, or topical), diluted with the correct diluent, in the correct amount; at the correct time and correct route and will record and document all drugs administered to the patient.

SUMMARY OF INVENTION

The present invention is directed toward a vial-loading mechanism for a system that prepares and delivers one or more IV drugs to a patient. The vial-loading mechanism is used to load a vial onto a cassette spike and includes a vertical support member located adjacent to the spike. A holding assembly holds at least one vial. The holding assembly is mounted to the support member so as to be positionable between an upper position for loading a vial and a lower position for piercing the vial with a spike. The holding assembly has an arcuate-shaped holding member for holding the vial. A catch is provided with an engagement unit for securing the holding assembly in the lower position. This arrangement provides an easy way to add, retain, and remove vials from the system and protects the clinicians that do this from contacting the spikes and hurting themselves.

BRIEF DESCRIPTION OF THE DRAWINGS

FIG. 12 is a diagram illustrating the vial loading mechanism according to one embodiment.

DESCRIPTION OF THE PREFERRED EMBODIMENT

The present invention is directed toward an improved vial loading mechanism for an automated medication delivery system.

Automated Medication Management System

Figure 2:
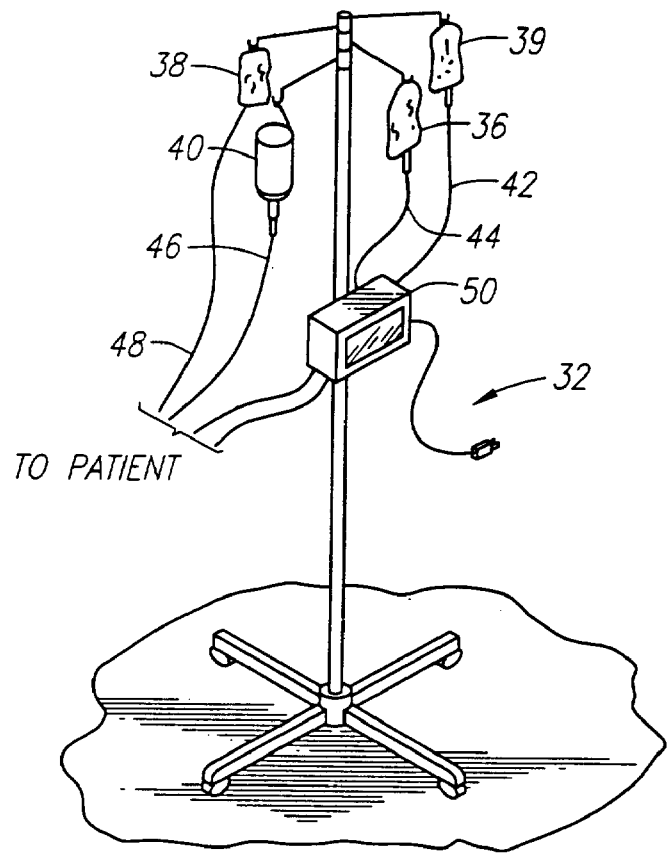
FIG. 2 is a perspective view of a conventional peristaltic infusion pump used to deliver IV solution to a patient.
Figure 3:
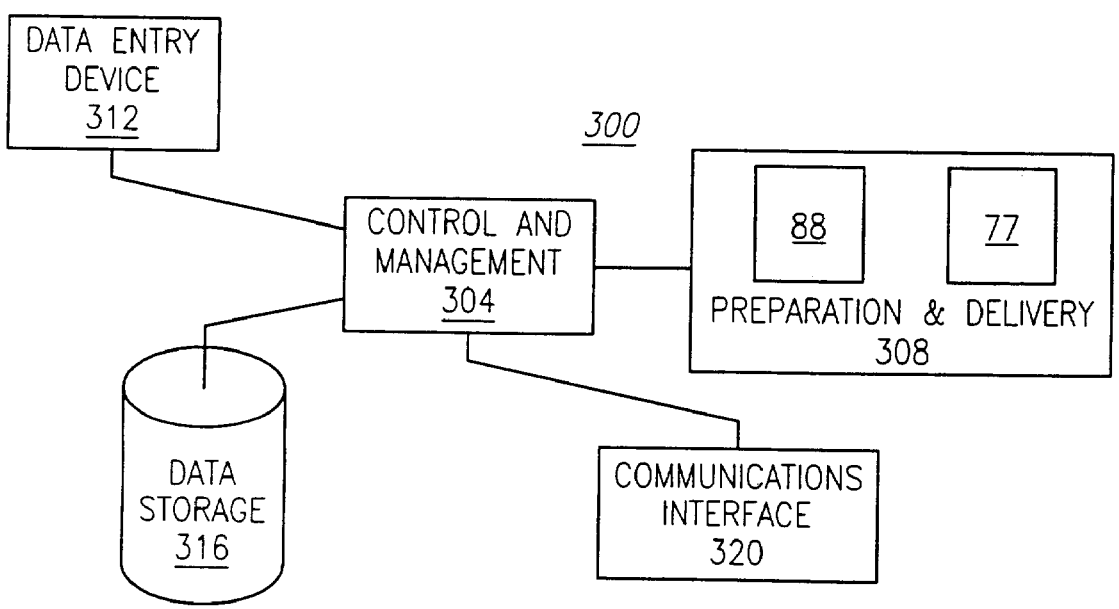
FIG. 3 is a diagram generally illustrating an automated medication management system according to one embodiment of the invention.

FIG. 3 is a diagram generally illustrating an automated medication management system 300 according to one embodiment of the invention. Referring now to FIG. 3, the automated medication management system in this embodiment includes a control and management module 304, and a preparation and delivery module 308. The automated medication management system 300 can also include a data entry device 312 and internal data storage 316. Additionally, a communications interface 320 can be provided for communication to external entities such as, for example, an external database 332, an external server (not illustrated), or other remote or external device(s), networks, or entities.

In the illustrated embodiment, preparation and delivery module 308 includes fluid delivery module 88 and cassette 77. Preparation and delivery module 308 provides automated reconstitution and dilution of medications, where required or appropriate. In one embodiment, cassette 77 incorporates one or more pressure conduction chambers, which are operated on by positive and negative pneumatic pressure supplied by fluid delivery module 88 to perform reconstitution, dilution and metering of the medication. Fluid delivery module 88 is controlled by control and management module 304.

Control and management module 304 determines the appropriate admixture process to be followed for the subject medication and controls fluid delivery module 88 to reconstitute and/or dilute the medication as determined. Control and management module 304 also controls delivery of the medication to the patient.

Control and management module 304 can receive data to determine the appropriate admixture process from one or more sources. These sources can include, for example, data entry module 312, external sources via communications interface 320 and internal data storage 316. Control and management module 304 can also use data from such sources to determine the appropriateness of the medication to be delivered to the particular patient.

Data entry device 312 can comprise one or more devices for inputting data such as, for example, a bar code reader, a keypad or keyboard, a touch-screen display, a magnetic card reader or other data entry device. The data entered using data entry device 312 can include, for example, patient data, medication data, clinician identification and other pertinent or related data. Entered data can be used for control and management of the delivery system and stored for later recall.

In one embodiment, data entry device 312 includes a bar code reader which can be used to scan bar codes on the medication to be administered to the patient. The bar code reader can also be used to scan bar codes indicating information such as, for example, patient ID's or other patient information from the patient's chart, wristband or other source; the clinician's ID (e.g., from an ID is encoded on a badge) and other information. In one embodiment, the combination of a bar code reader and a keyboard, for example, allows entry of scanned and manually entered data.

Internal data storage 316 can comprise one or more data storage devices for internally storing pertinent information. In one embodiment a medication administration record is stored internally for later retrieval or download. In another embodiment, an internal database can be included for storing information such as patient information, medication information and other pertinent information. Communication interface 320 can be used to communicate with external devices such as, for example, external databases, servers, controllers, or other entities. In one embodiment, communication interface is a network interface for connection to, among other network entities, a network database comprising information such as medication information, pharmacy information, patient information and other information.

In one embodiment, the system cross checks the medication to be administered against data contained in one or more databases to provide a safeguard against administration of improper medications or at improper dosage levels. In this embodiment, control and management module 304 checks the intended medication against information in the one or more databases and enables delivery only after verification that the particular patient is to receive a prescribed drug in the correct amount, with the proper diluent if required, at the proper time. Because this system provides a safety check before delivery of a drug, errors in delivering the incorrect drug or the incorrect amount are reduced.

Such a safety check can be performed any time after the prescription is entered and ideally, before the prescribed medication is administered to the patient. For example, the check can be performed at the time of prescription entry, before the prescription is prepared by the pharmacy, or before administration of the medication to the patient.

Having generally described an example architecture of the automated medication management system 300, its operation is now described in an example environment. The automated medication management system, according to the present invention, is suitable for use in numerous environments in which medications are delivered to a patient. Embodiments of the invention are now described in terms of one such environment. This description is provided to facilitate discussion of the invention in an example operational environment and is not intended to limit the invention to application in such an environment. In fact, after reading this description, it will become apparent to one skilled in the how to implement the invention in numerous alternative environments.

Figure 4:
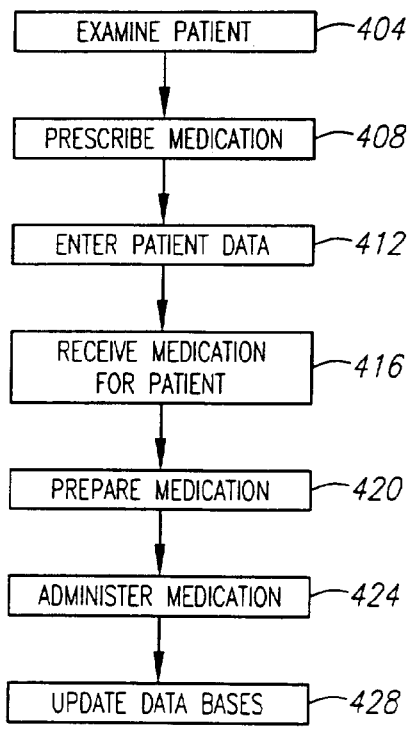
FIG. 4 is an operational flow diagram illustrating a method by which a patient treatment process performed according to one embodiment of the automated medication management system.

FIG. 4 is an operational flow diagram illustrating the operation of automated medication management system 300 in an example environment. In a step 404, a patient is evaluated by a health care professional such as, for example, a physician. The health care professional determines whether any medication is required or recommended to treat the patient's condition. If so, the appropriate medication, dosage and dosing interval are determined for that patient. In one embodiment, the physician can access a prescription analysis package that aids in the selection of the appropriate medication. This clinical decision-making database can be used to check diagnosis, patient demographics, known allergies, and current lab values to assist the physician in selecting the optimal medication.

In a step 408, after the health care professional determines which medication is appropriate to treat the patient's condition, a prescription is generated by that health care professional. The prescription is then delivered to and filled by a pharmacy, such as, for example, the hospital pharmacy. In one embodiment, the prescription is hand carried by a clinician or delivered by other manual means to the pharmacy so that it can be filled.

In an alternative embodiment, the physician order for the prescription can be entered into the data entry terminal and the prescription can then be electronically or otherwise automatically delivered to the pharmacy such as, for example, by electronic mail or by other electronic means. In yet another embodiment, the prescription can be entered using data entry device 312. The prescription can then be transferred to the pharmacy or other entity electronically via communications interface 320.

In an embodiment where the prescription information is entered electronically and stored in a database, the physician order can be automatically distributed to the pharmacy as it is entered into the database. Alternatively, the prescription can be subsequently retrieved from the database and sent to the pharmacy either automatically or by a health care professional. In other words, through the use of networking or other communication techniques, the delivery of the prescription to the pharmacy can be fully or partially automated.

Upon entry of a prescription, or prior to filling the prescription, the prescription information can be checked against one or more databases to determine the propriety of the prescription. If it is determined that the prescription as written or entered into the system may be inappropriate, steps are taken to warn of the error and allow the prescription to be verified or altered before administration of the prescribed medication. This process is described in greater detail below with reference to several embodiments.

In a step 412, pertinent patient data useful for the administration of the medication is entered into the automated medication management system 300. In one embodiment the information is stored in a patient database, and can be downloaded from the patient database to automated delivery system 300. This too can be done by a hard-wired or a wireless communication link. In one embodiment, the patient database or a duplicate copy thereof is resident in automated medication management system 300, allowing direct access of patient data.

In one embodiment, the identification of the patient is entered into automated delivery system 300, and this identification is used to retrieve one or more data records from the one or more databases. The patient data can be entered by the clinician using data entry device 312. Where data entry device 312 is a keypad, touch-screen display, keyboard, or other terminal-like device, the information is simply manually entered by the clinician. Where data entry device 312 includes an automated code reader such as a bar code scanner or magnetic reader or other code- or data-reading device, pertinent patient information can be scanned in using bar codes, magnetic stripes, voice recognition or other coded materials.

In one embodiment, the patient data entered into the automated medication management system 300 can include patient identification as well as other information pertaining to the patient.

In order to identify the health care professional to automated medication management system 300, his or her ID (identification) can also be entered. The ID can be a name, employee number or other identifying code or designation. In one embodiment, the ID can be entered by using a bar code or magnetic scanner to scan an identifying code provided by the health care professional. Such a code can be provided, for example, on the health care professional's badge. Additional security can be provided by requiring the health care professional to enter a PIN (personal identification number) or other password associated with his or her ID. Additionally, manual entry of ID and PIN can be provided by keypad or touch screen display. Alternative data entry means can also be utilized for identification.

In a step 416, the prescribed medication which has been received from the pharmacy is loaded into automated medication management system 300. This medication may be unprepared in that it requires reconstitution and/or dilution before it can be administered to the patient.

The automated delivery system can access information in a pharmaceutical database to determine whether reconstitution and/or dilution are required for each of the medications entered as well as the rate of delivery for the prepared medications. In one embodiment, control and management system 304 determines the proper admixture process and controls preparation and delivery module 308 for the admixture and infusion of the prescribed medications. Control and management system 304 may utilize internally or externally stored information such as, for example, IV templates to determine the correct reconstitution and dilution levels.

For example, control and management system 304 can look up a prescribed medication in a pharmaceutical or other database and determine from the database the appropriate reconstitution and dilution levels. Alternatively, this information can be dictated by the prescription and either manually entered or automatically downloaded to the automated medication management system 300.

In one embodiment, the medication information can be entered by data entry module 312 such as by the operator keying in the identification information or utilizing a bar code scanner or other code reader to read a bar code label on the medication container. The scanner can be a hand-held scanner connected to automated medication management system 300 via a wired or wireless interface.

In another embodiment, a bar code scanner or other code reader is integrated into the system such that the bar code label or other coded information is read from the medication vial when the vial is loaded into the system. As would be apparent to one of ordinary skill in the art after reading this description, other data entry techniques can be used as well.

The manner in which medicine is loaded into automated medication management system 300 is described in detail below. As described below, safeguards are provided to ensure that the chances of accidental exposure of the medication to the health care professional are minimized.

Various safeguards are provided to ensure that the appropriate medications are being loaded into the automated medication management system 300. In one embodiment, the clinician enters an identification of the medication into automated medication management system 300 and automated medication management system 300 verifies that this is the correct medication as prescribed to the patient by looking into the patient's database, or into a prescription database for example.

Automated medication management system 300 can also check various prescription, medication and patient information to ensure that the proper medication is being administered to the proper patient and at the correct dosage, and dosing interval.

For example, automated medication management system 300 can check the patient database to determine whether the prescribed medications conflict with any information in the patient database such as patient allergies, patient conditions, patient demographic information, or other information which would indicate an actual or possible incompatibility with the prescribed medication; current patient drugs which may be incompatible with the prescribed medication; whether the patient has already been prescribed medication to treat the condition to perform duplicate therapy checking; or other concerns which may be raised as a result of the prescription of the medication to the patient based on the stored information. If a concern or incompatibility does exist, a flag can be raised to the clinician via a warning sound, indicator light, message, or other display or indication on the automated medication management system or by a transmission of a message or signal to an appropriate location.

Automated medication management system 300 can also check a pharmaceutical database which contains information pertaining to the various medications. The pharmaceutical database can include one or more databases with information regarding drug interaction precautions and other drug incompatibility problems, as well as drug parameters, and IV template information. The information in this database can be stored locally in the automated medication management system 300 (either as original data or a duplicate copy), or stored remotely and accessed by automated medication management system 300 prior to administration of medication.

As an example of a check which may occur consider a scenario in which a patient suffers from high blood pressure. As is well known, there are certain medications which may further aggravate or compound the high blood pressure problem. If such a medication is prescribed for the patient, control and management system 304 can check the medication against known conditions which the medication may aggravate, determine from the patient database whether the patient suffers from any of these conditions, and, if so, raise an appropriate flag or warning.

In another example, other information such as either the dose or dosing interval of the medication or feedback on a patient's condition from a laboratory can be checked against the patient's age, weight, physical condition, or other factors to determine whether the prescription is within acceptable bounds. As such, a more fail-safe mechanism is provided as a cross check against the prescription of medication which may not be ideally suited to the particular patient given his or her condition.

This error-checking process can be similar to, or even duplicative of, the error checking process described below with reference to a physician order entry of the original prescription. One feature added at this stage, however, is the ability to verify the identification of the patient to whom the medication is actually going to be administered just prior to administration.

In one embodiment, delivery of the medication is not allowed to proceed if the error-checking process determines that it may be inappropriate to administer the medication as prescribed. In one embodiment, the halted system can be overridden by a health care professional with the appropriate authorization clearance level.

In one embodiment, if a warning flag is raised or the system halted, the condition can be overridden by the appropriate health care professional where that professional deems that the prescribed medication is appropriate under the circumstances despite the warning. For example, the physician prescribing the medication may note that it does aggravate a condition such as high blood pressure but may decide that the patient's need for the medication outweighs the risk in administering the medication and may therefore consider that the prescribed medication is still appropriate. In this situation, the physician simply overrides the alarm and allows the delivery to proceed. In one embodiment, the physician may do a preemptive override at the time of making the physician order in advance of receiving the actual warning. This override can be stored in the database so that the alarm is avoided. Additionally, occurrences of alarms and overridden alarms can be recorded for historical and statistical purposes.

In one embodiment, multiple levels of authorization are accommodated. Thus, different users may have different levels of "clearance" to perform operations such as prescribe medication, override alarms, administer medication, or perform other operations. For example, a user ID or other code may be required for the health care professional to operate the automated delivery system as well as a password or PIN. Different users can be provided with different levels of security, authorization, or access. For example, in this environment, a physician may be provided with the ability to enter a prescription and override a drug warning, whereas a nurse or other clinician may not. As would be apparent to one of ordinary skill in the art after reading this description, differing levels of hierarchy and various authorization levels can be provided based on the goals of the administration of the delivery system and the composure of the infrastructure in which it is implemented.

In a step 420, the medication is prepared for the patient. In this step, where reconstitution and/or dilution are required, preparation and delivery system 308 performs these operations. In one embodiment, as described below, the admixture process takes place in cassette 77 where the medications are properly reconstituted and/or diluted as required.

As discussed above, control of the admixture process is undertaken by control and management system 304 to ensure proper admixture is performed. Additional details on the manner in which the admixture process is performed according to one or more embodiments are provided below.

In a step 424, the prepared medication is delivered to the patient by preparation and delivery unit 308. The medication is properly metered such that the patient receives the correct dose over the defined period of time. The system can be set to provide alarms when air is present in the delivery lines.

In a step 428, one or more databases are updated to indicate that the patient has been administered the medication. This information can include information such as the medication administered, the dose administered, the date and time on which the medication was administered, and other important information. In one embodiment, this data is stored in an internal database (e.g., data storage 316) which can then be downloaded to an external database for record-keeping or archival purposes. In this embodiment, the internal database can be used as a history log recording a medication administration record performed by automated medication management system 300 over a period of time.

Thus, automated medication management system 300 can be transported from patient to patient for delivery of medication and keep an internal log of the deliveries and surrounding information. The information stored in the history log can be printed or displayed to provide health care professionals with information regarding recent transactions.

In alternative embodiments, the automated medication management system 300 can be more permanently connected or networked to an external database such that an internal log need not be kept to update patient, hospital, medication, or other records. Information from automated medication management system 300 can also be provided to accounting and other departments for billing, inventory, statistics collection, or other record-keeping purposes.

Example Implementation of Automated Medication Management System 300

Figures 5A, 5B:
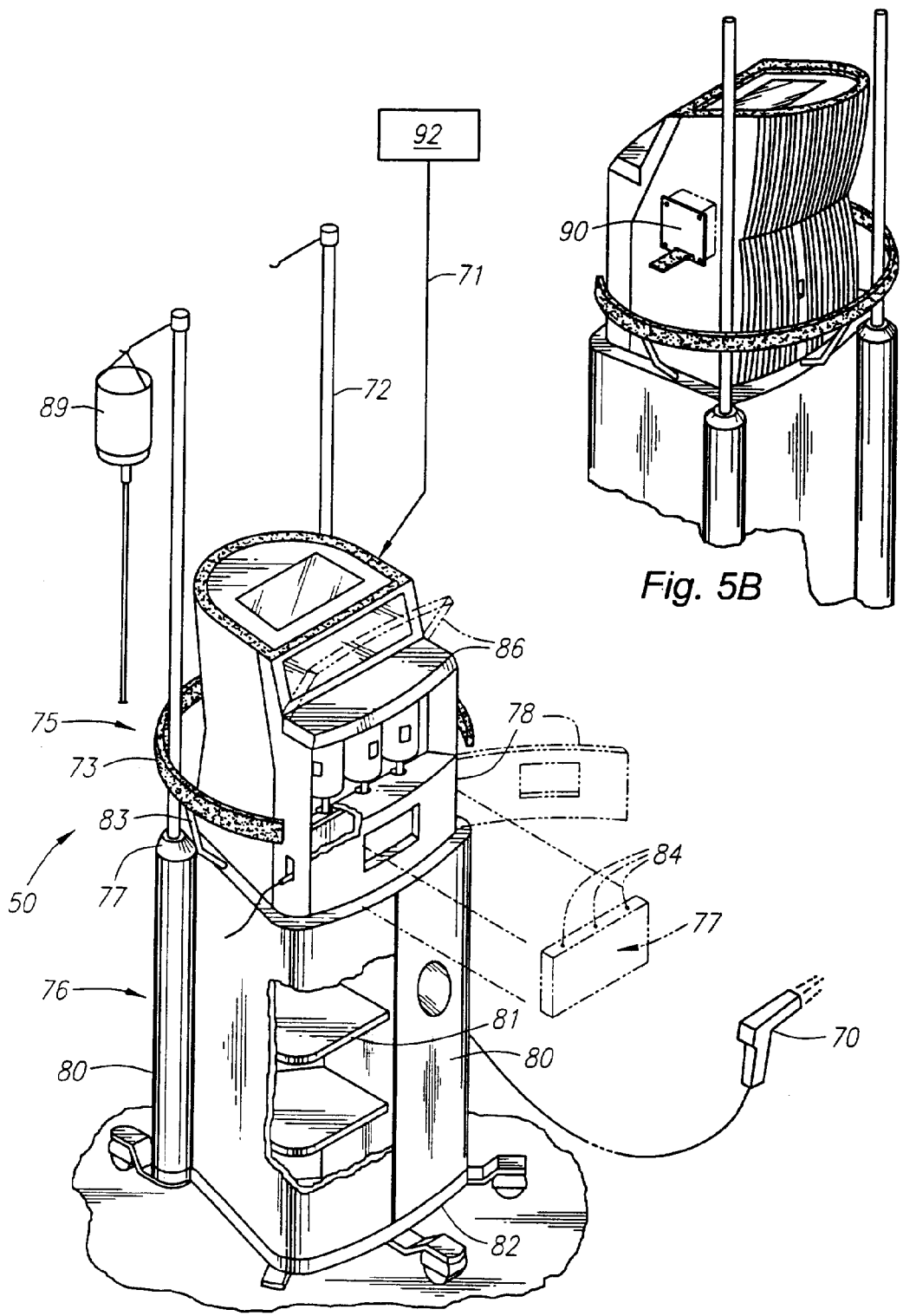
FIGS. 5A and 5B are perspective diagrams of an automated medication management system according to one embodiment of the invention.

An example implementation of automated medication management system 300 is now described with reference to FIGS. 5A and 5B. After reading this description, it will become apparent to one skilled in the art how to implement automated medication management system 300 utilizing alternative configurations. A detailed view of a bedside control and delivery unit 50 is shown in FIGS. 5A and 5B according to one embodiment. The Bedside control and delivery unit 50 includes a head unit 75 mounted on a base plate 77. The base plate 77 rests on the base assembly 76. Base assembly 76 includes side doors 80 which pivot open to reveal shelves 81, useful for storing medical paraphernalia. Also attached to base assembly 76 are IV poles 72 and a caster base 82. Ambulation bar 73 attaches to base assembly 76 through supports 83. The combination of caster base 82 and ambulation bar 73 allow stable patient ambulation.

Head unit 75 includes cassette 77 through which fluids and air are transported by fluid delivery module 88 (not shown). Cassette 77 is preferably disposable and not re-used for other patients or for delivery of subsequent medications to the same patient. Vial loading spikes 118 are disposed along the top of cassette 77. When cassette 77 is mounted in unit 75, drug vials 85 may be pierced by spikes 118 so that fluid from within cassette 77 may be forced into vials 85 to reconstitute the drug contained therein. Hinged door 86 covers vials 85 in ordinary use.

A clinician mounts cassette 77 by opening outer door 78 and inner door 87 (not shown) and positioning cassette 77 against fluid delivery module 88. The clinician then closes inner door 87 and outer door 78. In one embodiment, inner door 87 provides the necessary force to keep cassette 77 stationary against fluid delivery module 88 so that fluid delivery module 88 may pneumatically operate cassette 77. Outer door 78 serves as a safety check because if inner door 87 is opened, cassette 77 is disabled or otherwise prevented from contacting other patients. After inner door 87 is opened, fluids in cassette 77 could commingle and flow to the patient which can be hazardous. A disablement is provided to prevent this condition. Because cassette 77 is disabled once inner door 87 opens, a warning is displayed to the operator when outer door 78 is opened to prevent unnecessary disablement.

Bar code reader 70 or other data entry device can be used to scan the bar codes or other coded label on vials 85, pharmacy-prepared labels, manufacturer-prepared labels, and can also scan coded patient, physician and clinician identification. After the clinician enters or scans this information, unit 75 accesses drug database 92 which can be internal or an external database. Bedside control and delivery unit 50 verifies that the particular patient has been prescribed the particular drug being administered and that the diluent and additives in bag 89 are proper by accessing stored information such as, for example a patient profile contained in the patient database and the medication information stored in a pharmaceutical database. In addition, Bedside control and delivery unit 50 provides an alarm for dosages which exceed safe levels to be delivered by Bedside control and delivery unit 50.

Referring now to FIG. 5b, a back view of unit 75 is illustrated. Because in this embodiment Bedside control and delivery unit 50 contains a substantial amount of electrical and electro-mechanical hardware, a means for dissipating heat resulting from this hardware is provided. Because a fan could result in noise bothersome to patients, one embodiment of Bedside control and delivery unit 50 employs a large heat sink 91 instead. Other heat dissipation means can be used.

Also shown in FIG. 5b, a printer 90 can be utilized to print records of medications delivered to the patient. Rather than requiring a clinician to manually keep records of administered medications, in one embodiment as described above, Bedside control and delivery unit 50 records all drug events and can then print those events on printer 90 or download them to a database. Alternatively, the system can access a remote printer at the nurse's station via a network connection. In one embodiment, a caster base 82 or other rollers are provided to facilitate ambulation of the system.

Figure 6:
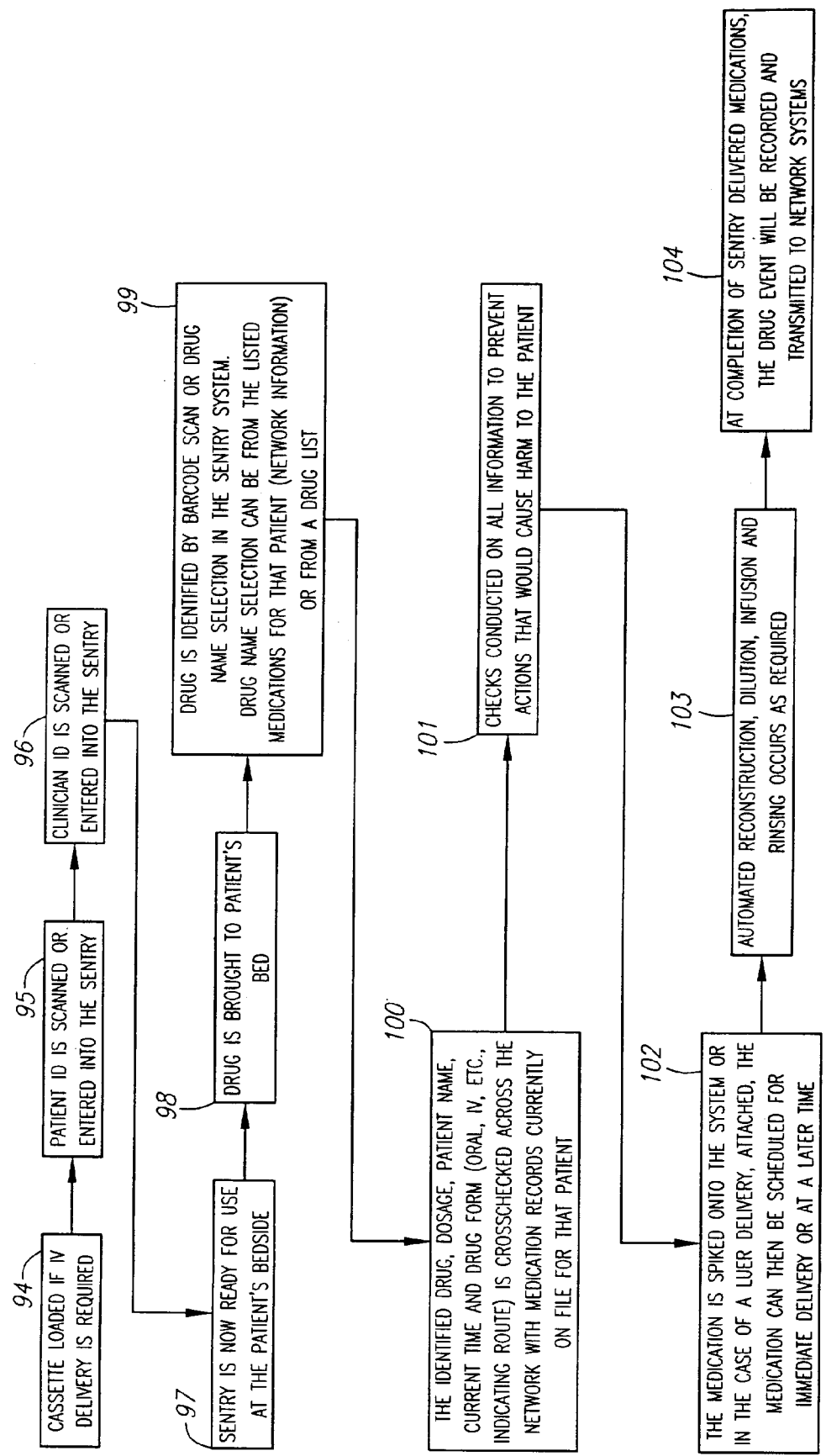
FIG. 6 is a flow diagram indicating the steps which are utilized for data entry compounding, confirmation of the identity of patient, and drug and recording and monitoring drug usage and delivery according to one embodiment of the invention.

FIG. 6 is a block diagram generally illustrating the use of automated medication management system 300 for administering medication to a patient in the embodiment described in FIGS. 5A and 5B. To begin the process, in a step 94, the system is brought to the patient's bedside. A cassette 77 is loaded if IV delivery is required. In one embodiment, a network connection is established by powering up the system.

In a step 95, The patient's identification is scanned through the use of scanner 70, so that the system can be set up to support the specific patient and can check that the medication is actually prescribed for the identified patient. At step 96, the clinician's identification can be scanned as well and his or her password entered. This acts as a security measure, to help prevent unauthorized personnel from altering drug delivery parameters or administering drugs without authorization. Alternatively the identification can be entered manually or via other data-entry means.

As discussed above, in one embodiment the system uses the patient identification to check one or more databases as a cross check against the medication being provided to the patient in the instant infusion.

After completion of the above, the system is ready for use as shown in step 97. Now, the clinician may bring the drug to be administered to the patient's bedside for installation in automated medication management system 300 at step 98. The drug is identified, such as for example by barcode scan at step 99. If the drug does not have a barcode label, the clinician may identify it through a list imported from the network 71 or through a drug list residing in memory within the system or by manual data entry.

In step 100, the system verifies that the identified drug, dosage, patient name, time of delivery, and route of delivery correspond with prescription information on file. Should all information be correct, in step 101, the system proceeds with its operation.

The clinician is notified of inaccuracies and asked to correct them if he or she still wishes to proceed. However, in certain circumstances, such as for example where the requested dosage exceeds the maximum allowed level, the system does not allow or approve delivery. In one embodiment, the system can be overridden with the appropriate authorization.

At step 102, the clinician loads the desired drug vial 85 onto the cassette 77. For medications which are not delivered through cassette 77, the user enters the information into bedside control and delivery unit 50 so that the drug event data can be transferred to other databases within the hospital.

In step 103, the system reconstitutes, dilutes, and infuses cassette-prepared medications. After infusion, the cassette is rinsed so that no incompatible drug reactions occur upon the next drug delivery cycle. Finally, at step 104, the system records all delivered drug events, whether administered through the cassette or through other routes. That information may be transmitted to other databases within the hospital.

Figure 7:
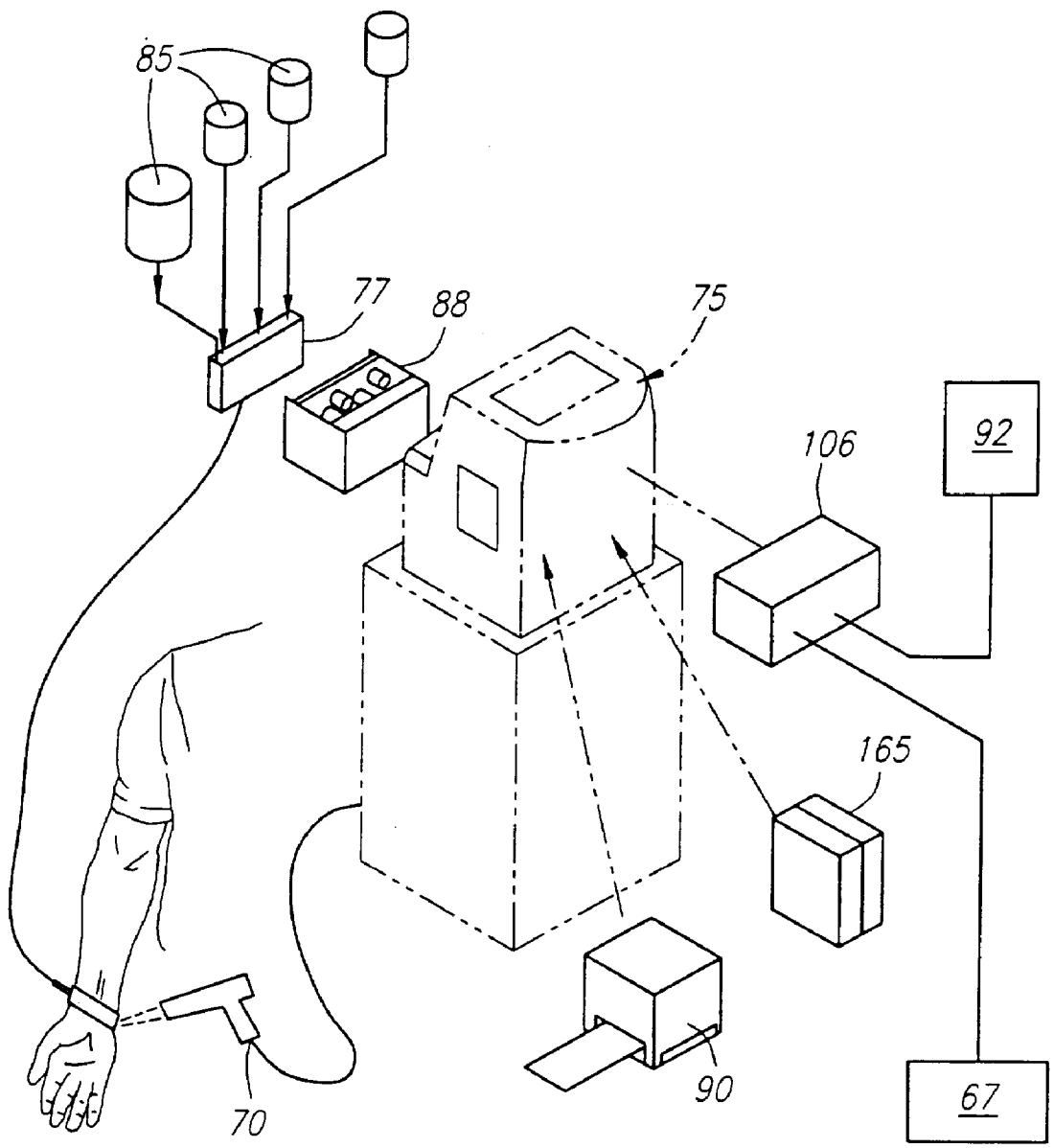
FIG. 7 is an exploded view of the automated medication management system according to one embodiment of the invention.

FIG. 7 is a diagram illustrating a simplified exploded view of head unit 75 according to the example implementation illustrated in FIGS. 5A and 5B. Fluid delivery module 88 pneumatically operates cassette 77 so as to reconstitute vials 85. Inside unit 75 is the control and management unit 304 which controls overall operation of Bedside control and delivery unit 50, using software 67 and database 92.

A battery 105 or other alternative power source allows mobile use and uninterrupted operation in case of power failure. Bar code scanner 70 is shown reading a patient's identification bar-code on a wristband. Such information will eventually be recorded by Bedside control and delivery unit 50 as part of all drug events monitored or delivered by the present invention.

Control and management module 304 controls fluid delivery module 77 so as to provide automated reconstitution, dilution, infusion, and rinsing of medications delivered through cassette 77. Module 304 also works to communicate with database 92 for verification and recording of all other medication deliveries. Fluid delivery module 88 operates on cassette 77 so that fluids and air can be moved through cassette 77 without any contact with fluid delivery module 88. In one embodiment, module 304 includes an X86 processor-based system such as, for example, a 386 CPU and associated peripherals.

Example Implementation of Cassette 77

Figure 8:
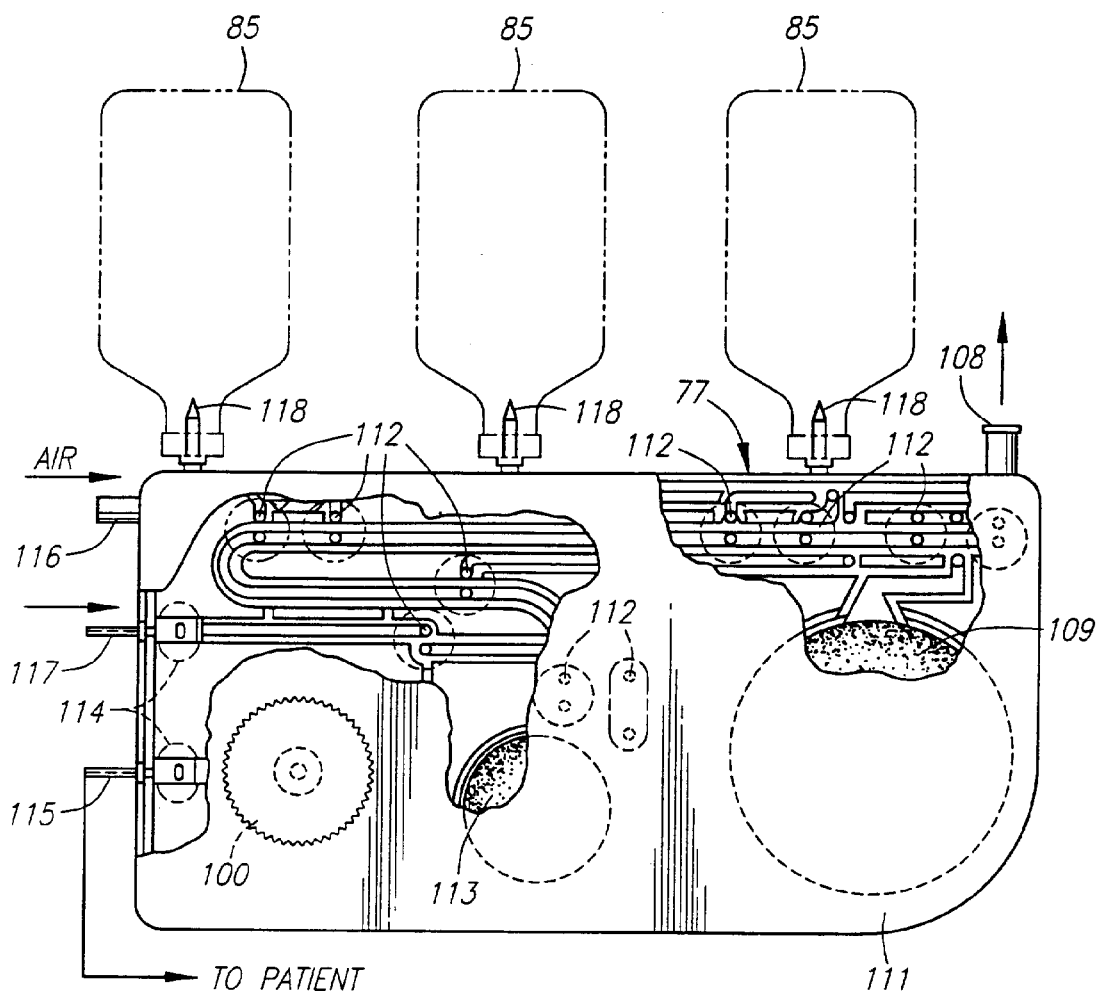
FIG. 8 is a detailed illustration of an example implementation of a cassette with vials mounted thereon according to one embodiment.

FIG. 8 is a detailed illustration of an example implementation of a cassette 77 with vials 85 mounted thereon according to one embodiment of the invention. The components and relevant materials of the cassette 77 according to one embodiment are listed in the table below. Alternative materials can be used to implement cassette 77.

| COMPONENT | MATERIAL |
| --- | --- |
| Valves 112 | Santoprene 281-64 |
| Mixing chamber diaphragm | Santoprene 281-64 |
| Delivery chamber diaphragm | Santoprene 281-64 |
| Control Wheel Seat Insert | Santoprene 281-64 |
| Control Wheel Seat Base | Pro Fax PD-626 from Himont |
| Midbody 113 | Monsanto Lustran ABS 248-2002 (white) |
| Control Wheel 600 | Monsanto Lustran ABS 248-2002 (white) |
| Front Cover 111 | BASF Terlux 2812TR |
| Rear Cover 111 | BASF Terlux 2812TR |
| Spikes 118 | Monsanto Lustran 248-2002 (white) |
| Spike Covers 126 | Polyethylene |
| Luer Lock Cap | Polyethylene |
| Vented Air Cap | Polyethylene |

The cassette 77 according to this embodiment is now described. The cassette is comprised of a mid-body 113 which contains the fluid delivery pathways and seats for the diaphragms and valves. Midbody 113 is ultrasonically welded to the two covers which sandwich the diaphragms, valves and control wheel 110 in an assembly. Spikes 118 are separately molded pieces which are also ultrasonically welded to midbody 113 and inner and outer covers 111. Tubing is bonded to the cassette for both the proximal 117 and distal ports 115 and air input port 116. Standard set components make up the remainder of the administration set.

The cassette and set are packaged and sterilized to provide a sterile fluid pathway. All cassette and set materials have been tested for biocompatibility and meet ISO 10993 standards. Caps 126 on the three vial spikes 118, the luer port 108, the proximal tubing port 117 and the distal tubing port 115 provide sterile barriers so that the set and cassette assembly is a closed loop system and is preserved sterile when it is removed from the package. Once the cassette 77 is loaded in the Bedside control and delivery unit 50, the vial spikes 118 and luer port 108 are maintained sterile by keeping the caps 126 in place until the time of use for each respective port.

On both sides of cassette 77 are rigid plastic covers 111 covering cassette 77. Pressure conduction chambers 109 and 110 have windows fashioned on inside cover 111, thus exposing the flexible diaphragm for each chamber. The valves 112 are formed in an analogous fashion. Fluid delivery module 88 can apply positive or negative pressure to the pressure conduction chambers 109 and 110.

When applied to the flexible diaphragm covering pressure conduction chambers 109 and 110, the pressure acts to draw fluid into the chambers or expel fluid out of the chambers. The valves 112 are controlled by DC motors which are cam actuated. The cam actuation opens and closes valves 112. In this way, through a combination of positive and negative pressure applied to the chambers 109 and 110, and the actuation of valves 112, fluid delivery module 88 can pump fluid from inlet line 117 into the vials 85, reconstitute the medicine therein, and withdraw the fluid from the vials 85 back into chamber 109. Repetition of fluid movement into a vial 85 and back into chamber 109 assures that the medicine is entirely reconstituted. This fluid can then be precisely diluted in chamber 109 which is denoted the mixing chamber. Chamber 110 is denoted the metering chamber because the fluid is precisely measured and pumped into outlet line 115. Movement of fluids in this fashion is disclosed in U.S. Pat. Nos. 4,848,872; 4,778,451; 4,786,800; 4,804,380; 4,816,019; 4,826,482; 4,976,162; 5,088,515, 5,178,182, 5,193,990, 5,241,985, 5,353,837; 5,364,371; 5,401,342, which are incorporated herein by reference.

Fluid delivery module 88 also possesses acoustic volume sensing technology whereby a loudspeaker transmits sound waves into an acoustic volume sensing (AVS) chamber of fluid delivery module 88 and thereby measures the resonant frequency of the AVS chamber. The AVS chamber of the fluid delivery module is in communication with chamber 110 of the cassette. By measuring the volume of air in the AVS chamber through resonant frequency monitoring, the volume of fluid within chamber 110 can be calculated by a microprocessor contained within fluid delivery module 88. In addition, should air bubbles be entrained in the fluid within the pressure conduction chamber 110, these bubbles will be detected by AVS. The microprocessor will monitor for the presence of air bubbles and will not pump liquid containing bubbles from the cassette 77 to the patient. Instead, the liquid/bubble mixture is either pushed back to the fluid source 89 or will be kept in chamber 109 until it is safe to expel the bubble to 89. Air can enter vials 85 through the air channel 116, preventing a vacuum condition from occurring as vials 85 are drained into mixing chamber 109. Acoustic volume sensing technology is set out in U.S. Pat. Nos. 5,211,201; 5,349,852; 5,526,844; 5,533,389, which are incorporated herein by reference.

Figure 9:
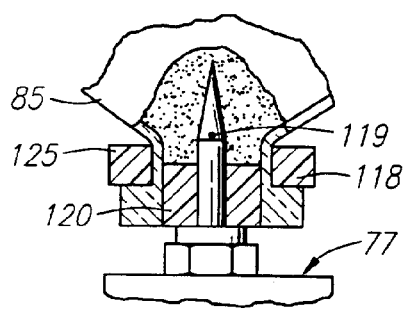
FIG. 9 is a diagram illustrating a vial mounted to a cassette spike according to one embodiment.
Figure 10:
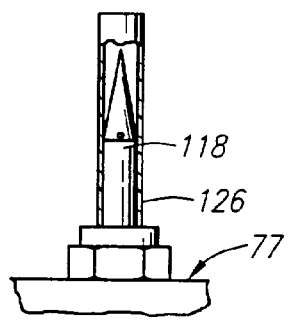
FIG. 10 is a cross-sectional view of a spike with a cap mounted thereon.

Fluid within cassette 77 is pumped into vials 85 from mixing chamber 109. The means by which vials 85 are attached to cassette 77 is illustrated in FIG. 9 according to one embodiment. Vial 85 is held by clamp 125, part of a vial-loading mechanism discussed below. Spike 118 has a lumen 119 through which fluids and air may pass into cassette 77. When vial 85 is mounted on spike 118, the sharpened end of spike 118 pierces elastic seal 120 of vial 85 so that lumen 119 is now in contact with contents of vial 85. The elasticity of seal 120 ensures an airtight seal about spike 118. Clamp 125 holds vial 85 stationary during system operation. When vial 85 is not mounted, a protective cap 126 covers spike 118 to maintain sterility and to protect users as illustrated in FIG. 10.

Figure 11:
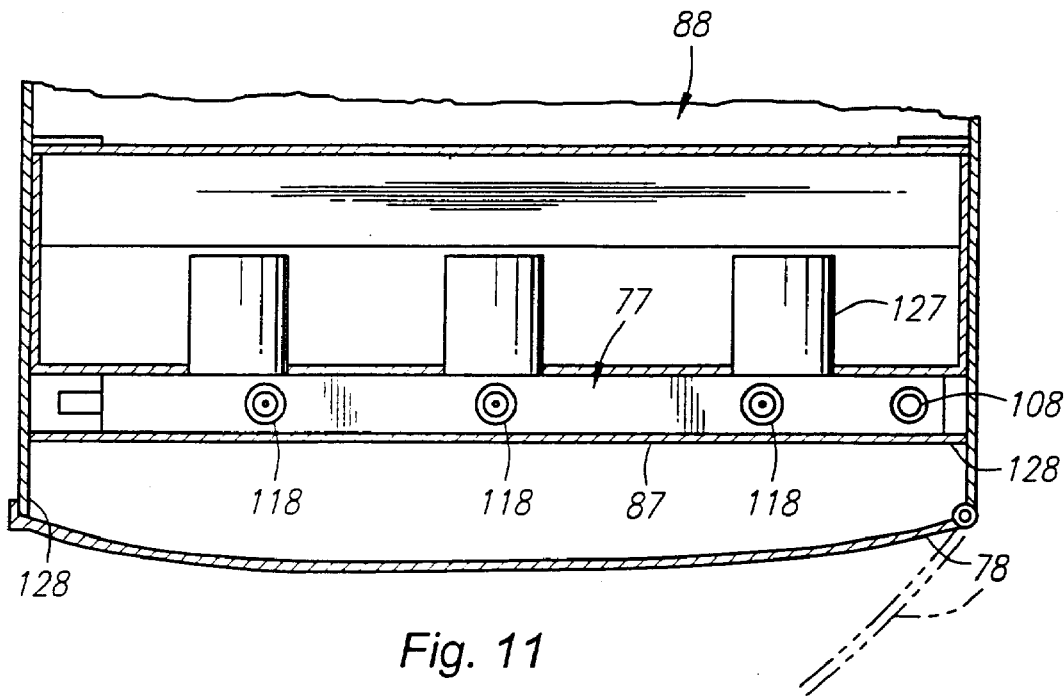
FIG. 11 is a diagram illustrating a downward view of how a cassette mounts on unit 75 according to one embodiment.

A downward view illustrating how cassette 77 mounts on unit 75 according to one embodiment is shown in FIG. 11. Spikes 118 and luer port 108 are shown without any connections. To mount cassette 77, outer door 78 is pivoted open in one embodiment. Inner door 87 pivots at its bottom to swing open. After cassette 77 is placed against fluid delivery module 88, inner door 87 is pressed shut. In one embodiment, spring-loaded cams 128 are pushed aside as door 87 closes. When inner door 128 is fully closed, cams 128 return to their locking position. In this way, inner door 87 is held with sufficient force against fluid delivery module 88 so that pneumatic drivers can apply positive and negative pressure against the diaphragms of chambers 109 and 110 without leakage of pressure.

Figure 15:
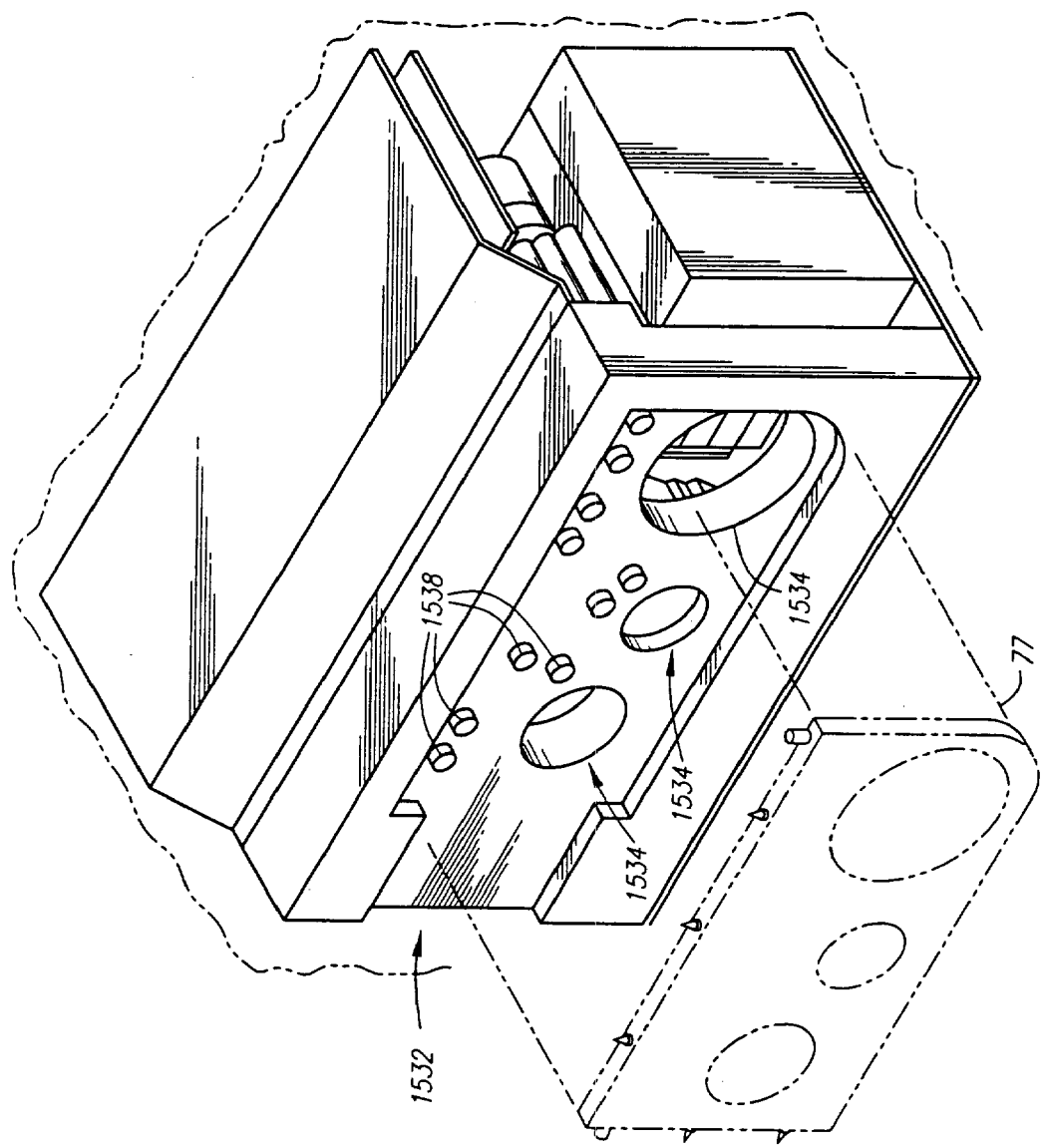
FIG. 15 is a diagram illustrating a perspective view of a cassette and a mounting structure for the cassette according to one embodiment of the invention.

FIG. 15 is a diagram illustrating a perspective view of a cassette 77 in proximity with a portion 1532 of automated medication management system 300 designed to accept cassette 77. As illustrated in FIG. 15, one or more openings 1534 are provided to allow FMS and/or AVS actuation to to control the operation of Pressure conduction chambers 109 and 110 on cassette 77. Actuators 1538 are used to control the operation of valves 112.

Example implementations of cassette 77 are disclosed in in application numbers, titled "System, Method and Cassette for Mixing and Delivering Intravenous Drugs," and "Cassette for Intravenous-Line Flow-Control System." These documents are incorporated herein by reference to illustrated one example implementation of a cassette 77. Alternative implementations of cassette 77 can be used in conjunction with automated medication management system 300, including numerous alternative currently commercially available cassettes.

Vial Loading Mechanism

Figure 13:
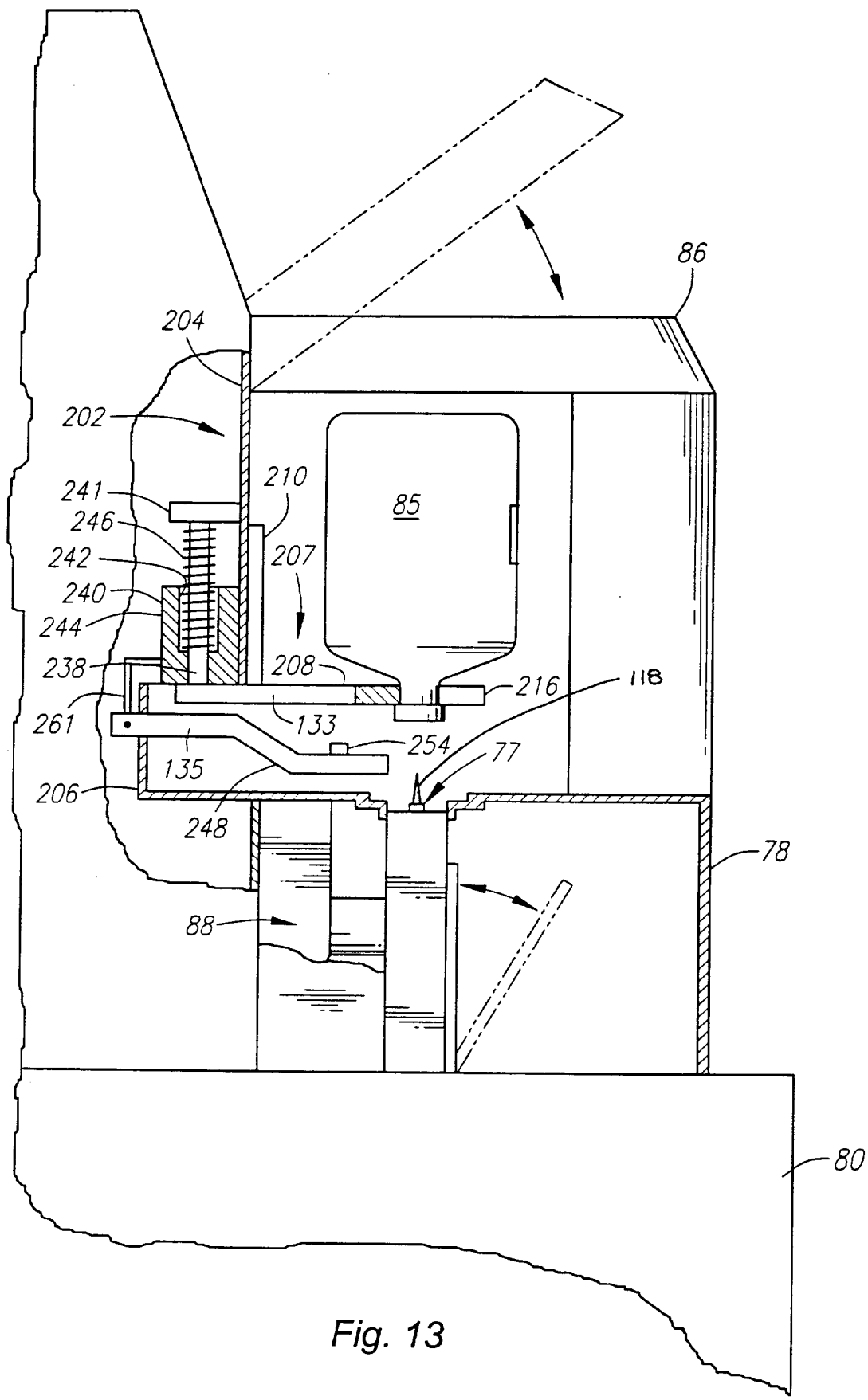
FIG. 13 is a diagram illustrating the vial loading mechanism according to one embodiment.

FIGS. 12 and 13 illustrate a vial loading mechanism according to one embodiment of the automated medication management system 300. As would be apparent to one of ordinary skill in the art after reading this description, alternative vial loading mechanisms can be implemented.

In order to connect the vials 85 to the cartridges 77, the membrane seals 120 of vials 85 are pierced. The clinician accomplishes this by inverting each vial 85 and lowering the vial 85 onto the spike 118 so as to pierce seal 120 with spike 118.

With reference to FIGS. 12 and 13, to prevent the clinician from accidentally contacting the spikes 118 and injuring oneself, a vial loading mechanism, indicated generally by the reference numeral 200 can be provided. Vial loading mechanism 200 includes a panel assembly 202. Panel assembly 202 has an upper portion 204 and a recessed portion 206.

In front of recessed portion 206, a plurality of holders 207 are provided. Each holder 207 includes an outer holding arm 208 and an inner holding arm 210. The outer holding arm 208 includes a proximate end 212 adjacent to the panel assembly 202 and a distal end 214. The distal end 214 includes an arcuate holding portion 216. A tang 218 extends inwardly from a lower part of one side of the arcuate holding portion 214. A groove 220 is provided in an upper portion of this side. A cutout 222 is provided in the lower part of the opposite side of the arcuate holding portion 214. The cutout 222 allows the head of the vial 85 to fit into the arcuate holding portion 216 and the tang 218 supports the head of the vial 85. A rectangular cutout or slot 224 is provided in the outer holding arm 208 and is defined by a pair of opposing walls 226 and an end 228.

The inner holding arm 210 is pivotally connected to the opposing walls 226. The inner holding arm 210 includes a main body 230 with a sleeve 232 at one end and a penannular holding portion 234 at an opposite end. Both the arcuate holding portion 216 and the penannular holding portion may have a corrugated, a rubber or an other friction-prompting inner surface to enhance the frictional engagement between the vial 85 and holding portions 216, 234. A projection 236 extends in a generally lateral direction from the holding portion 234.

The inner holding arm 210 is pivotally connected at the sleeve 232 to the walls 226 of the outer holding arm 208 through a pin, or other similar fastening means. The inner holding arm 210 pivots from a raised (out-of-the-way) position to a lowered position, where the inner holding arm 210 is stopped by a tang 237. FIG. 12 illustrates the inner holding arm 210 in both of these positions. Although not shown, a spring may be provided to bias the inner holding arm 210 to the raised and/or lowered position. Also, a locking device may be provided to retain the inner holding arm 210 in the raised and/or lowered position.

With reference to FIG. 13, a shaft 238 extends from the outer holding arm 208 at its proximate end 212 and terminates at a head plate 241. The shaft 238 vertically reciprocates within a bushing 240. The bushing 240 includes a bore 242 and a lip 244. A helical spring 246 surrounds the shaft 238. The spring 246 is disposed at least partially within the bore 242 of the bushing 240, between the lip 244 and the head plate 241.

When the holder 207 is lowered, the shaft 238 reciprocates within the bushing 240 and the spring 238 is compressed. This causes an upwards restoring force, in the opposite direction.

To retain the holder 207 in a lowered position, a locking device 247 is provided. The locking device 247 includes a worm-like locking arm 248 that extends alongside and in the same direction as each holder 207. The locking arm 248 includes a proximate end 250 and a distal end 252. Near the distal end 252, a moon-shaped cam 254 is provided. The cam 254 has a curved upper surface 256 and a flat lower surface 258. A curved projection 260 extends from the distal end 252 of the locking arm 248. Near the proximate end 250, the locking arm 248 is connected to the bushing 240 by a torsion or spring bar 261. The torsion bar 261 provides a restoring force on the locking arm 248 when the locking arm is moved in a manner to be described. Alternatively, the locking arm 248 may have a construction that eliminates the need for a torsion bar 261. For example, the locking arm may be directly connected to the bushing 240 if the locking arm 248 is made of a resilient material.

The vial loading mechanism 200 will now be described in use. The vial loading mechanism is designed to be used with two different, industry standard size vials—a 13 mm size vial and a 20 mm size vial, but can be built to utilize other sizes as well.

If the 13 mm size vial is to be used, the clinician must make sure that the inner holding arm 210 is in the lowered position. This can be done by pivoting the inner holding arm 210 with the help of projection 236. The vial 85 is inverted and the neck of the vial 85 is snapped into, or frictionally engaged with, the holding portion 234 of the inner holding arm 210. The clinician forces the holder 207 to be lowered so that the spike 118 pierces the membrane seal 120 of the vial 85. Because the spring 246 provides an upward force on the holder 207 when compressed, the holder 207 must be retained or locked in the lowered or locked position. This is accomplished through the locking device 247. As the holder 207 is lowered, the lower part of one of the walls 226 contacts the cam 254 of the locking arm 248, causing the locking arm 248 and cam 254 to move out of the way. The holder 207 is further lowered until the locking arm arm is allowed to move back to its original, locked position. In the locked position, the flat lower surface 258 of the cam 254 retains the holder 207 in this position, regardless of the restoring force of the spring 244.

The bedside device monitors whether the vial 85 is in the locked position by a vial-attachment sensor (not shown).

To remove the vial 85 the locking arm 248 is moved laterally with the projection 260 until the flat lower surface 258 of the cam 254 no longer blocks or retains the holder 207. The restoring force in the spring 246 causes the holder 207 to rise to its original position where it is maintained in an unlocked position by the force of the spring 246. The vial 85 is then removed from the holding arm 210.

In the event that a vial 85 or protective cap 126 does not replace the unloaded vial, the system will disenable the cassette 77 in order to maintain aseptic conditions.

If the 20 mm size vial 85 is used, the inner holding arm 210 must be located in the upward (out-of-the-way) position. This may be done by pivoting the arm 210 upwardly using projection 236. This allows the larger-size vial 85 to fit within the arcuate holding portion 216 of the holder 207 and be lowered onto the spike 118 in the same manner as that described above.

The vial loading mechanism of the present invention provides an improved, safe, and easy way of loading, retaining, and unloading vials in a bedside delivery system. The vial loading mechanism inhibits clinicians from contacting the spikes 118 of the system and hurting themselves.

Example User Interface

Figure 14:
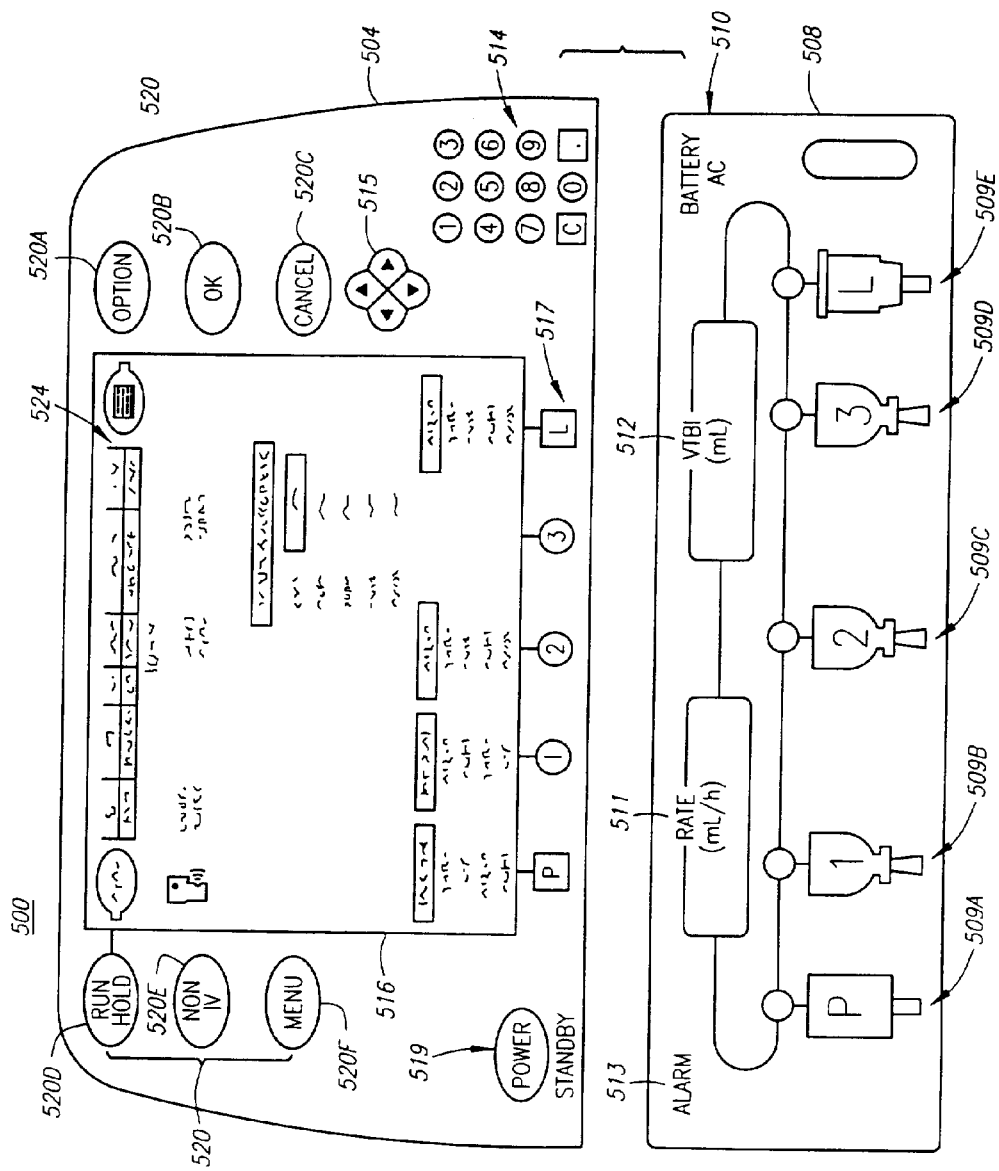
FIG. 14 is a diagram illustrating an example user interface for an automated medication management system according to one embodiment of the invention.

FIG. 14 is a diagram illustrating an example user interface for an automated medication management system 300 according to one embodiment of the invention. More specifically, FIG. 14 illustrates a specific interface implemented in conjunction with the bedside control and delivery units illustrated in FIGS. 5A and 5B. As would be apparent to one of ordinary skill in the art after reading this description, automated medication management systems 300, including the bedside delivery and control units, can be implemented with alternative user interfaces. The description of the user interface now described is provided by way of example only.

The user interface according to the embodiment illustrated in FIG. 14 is comprised of two sections, a user operation and interface section 504 and a display section 508. Display section 508 includes indicator lights and displays to provide a clinician with information regarding medications being administered to a patient. Indicators 509A–509E provide the clinician with information as to which of a plurality of IV ports are currently being used to administer medication. In the embodiment illustrated, there are three IV ports as denominated by indicators 509B, 509C, and 509D, a luer port denominated by indicator 509E, and a primary port indicated by 509A.

A rate indicator 511 provides a numerical display as to the rate at which medication is being administered to the patient. In a preferred embodiment, this is provided in units of ml/hr. Display 512 provides an indication of the volume of the medication which has yet to be administered to the patient. In a preferred embodiment, this display is provided in units of milliliters.

In one embodiment, indicators 511, 512 are implemented using LED or LCD display providing numerals of sufficient size and intensity such that they are easily legible. In alternative embodiments, alternative display technologies are utilized to provide a legible display.

Power indicator 510 informs a user whether the system is running off of battery or AC power and an alarm indicator 513 provides an indication as to whether an alarm condition is present. These indicators are backlit such that the characters are illuminated when the indicator is activated. Alternative indicator types can be utilized as would be apparent to one skilled in the relevant art.

User operation and interface portion 504 is comprised of a plurality of buttons and a display screen to function as the primary user interface for the system. a power button 519 is used to power the system on or to place the system in a stand-by mode. a keypad 514 is used to allow manual entry of data by a user. The keypad 514 illustrated in FIG. 14 is a numeric keypad allowing only the entry of numeric data. In alternative embodiments, alphanumeric keys, function keys and other types of keypads can be provided to allow the entry of additional data. Additionally, a cursor control keypad 515 is provided to move a cursor on display screen 516.

In the embodiment illustrated in FIG. 14, display screen 516 is a computer display screen such as that commonly used in personal computers. Display screen 516 can be used to provide information to the user and to allow the user to enter control information. In one embodiment, the automated medication management system 300 is a Windows-based system. In this embodiment, display screen 516 is used to provide menu options or window screens to the user to allow the user to control the system as well as to provide information regarding the operation of the system. a cursor keypad 515 is provided to allow the operator to position a cursor on display screen 516 to enable selection.

Additional buttons 520 are provided to allow additional control selections to be made by the operator. Buttons such as option button 520A, O.K. button 520B, cancel button 520C, run/hold button 520D and non-IV button 520E and menu button 520F are used to select a pull-down menu 524, confirm a selection, cancel a selection or operation, pause or resume an operation or to allow an operator to designate that a medication being administered is other than an I.V.-type medication. Indicators 517 are used to indicate which portions of display screen 516 provide information with regard to particular I.V. ports.

As stated above, alternative configurations can be provided for the user interface depending on the application and environment for the system. The embodiment illustrated in FIG. 14 provides an example of a specific user interface in one embodiment of the system. After reading this description, it will become to a person skilled in the relevant art how to implement alternative user interfaces which allow control, operation and monitoring of the system. In a more generic embodiment, for example, the entire user interface can be implemented using a computer display screen in conjunction with a keyboard and/or a mouse. In this embodiment, all of the control and display operations are accomplished using conventional computer interface techniques.

Example Architecture For An Automated Medication Management System 300

Figure 16:
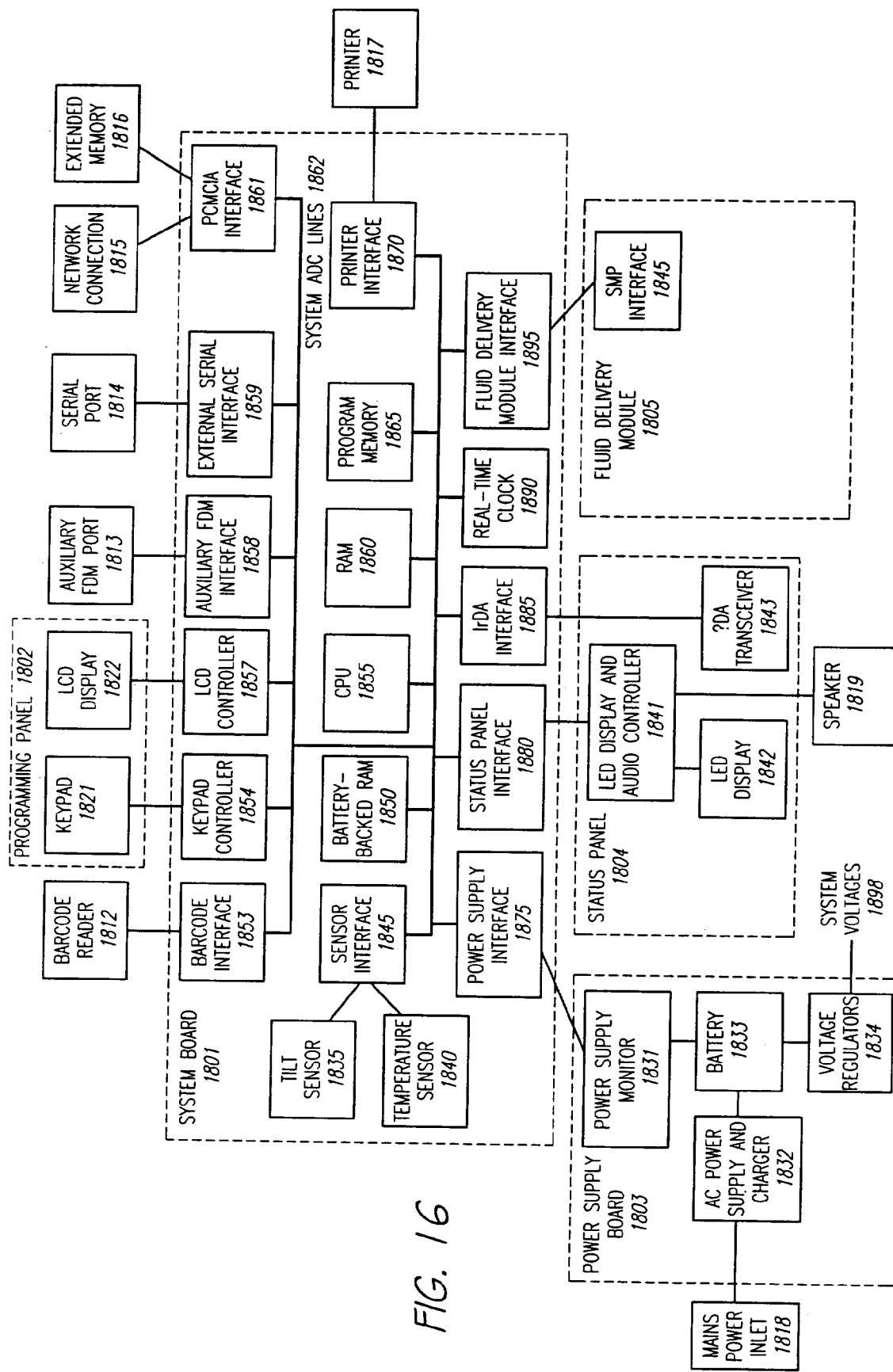
FIG. 16 is a block diagram illustrating an example architecture for an implementation of automated medication management system according to one embodiment.

FIG. 16 is a block diagram illustrating an example architecture for an implementation of automated medication management system 300. This example architecture is now described with reference to FIG. 16. After reading this description, it will be apparent to a person skilled in the relevant art how to implement automated medication management system 300 using alternative architectures.

The architecture illustrated in FIG. 16 is comprised of five primary modules: system board 1801, programming panel 1802, power supply board 1803, status panel 1804, and fluid delivery module 1805. Additionally, the architecture illustrated in FIG. 16 includes several auxiliary elements.

System board 1801 is primarily responsible for the control and operation of automated medication management system 300. System board 1801 is a processor-based board controlled by CPU 1855. In one embodiment, system board 1801 is an X86-based board capable of running the DOS or the Windows 3.1 or Windows 95 operating systems. In the illustrated architecture, RAM 1806 and program memory 1865 are used to store data necessary for the operation of CPU 1855. Instructions for controlling the operation of CPU 1855 are stored in program memory 1865. RAM 1860 is used by CPU 1855 to store operating information. Additionally, battery-backed RAM 1850 is provided to store information that needs to be maintained between power cycles of the system. A real time clock 1890 is provided to maintain synchronization of CPU 1855.

System board 1801 also includes a tilt sensor 1835 and a temperature sensor 1840 to sense the operating environment of the system. These boards communicate with CPU 1855 via a sensor interface 1845. As would be apparent to one of ordinary skill in the art, additional sensors can be included to receive and provide data regarding the operating environment or numerous other parameters important to the operation of automated medication management system 300. In addition to the above-described components, system board 1801 includes a plurality of interfaces and controllers used in communication with the other modules, external peripherals, and other systems and devices.

The interfaces include a power supply interface 1875, a status panel interface 1880, and IrDA interface 1885 (infrared device interface), a fluid delivery module interface 1895, a printer interface 1870, a PCMCIA interface 1861, an external serial interface 1859, an auxiliary FDM (fluid delivery module) interface 1858, an LCD controller 1857, a keypad controller 1854, and a bar code reader interface 1853. Each of these interfaces and controllers provide the communications necessary to interact with the devices and modules to which they are connected. Each of these interfaces and controllers are discussed below with reference to the modules and devices with which they interact.

Programming panel 1802 is provided to allow an operator or user of the system to program or otherwise control the operation of the automated medication management system 300. a key pad 1821 allows the user to enter data or control the operation of automated medication management system 300. Key pad 1862 in one embodiment has a simple numeric key pad in combination with four arrow keys to provide cursor control. With a simple key pad such as this, a user can navigate his or her way around options displayed on a screen such as a CRT, and select those options to operate the system. More complex key pads including alphanumeric buttons and/or function keys can be utilized to provide additional levels of control. Key pad 1821 is interfaced to system board 1801 by a key pad controller 1854.

LCD display 1822 is utilized to provide a display to the user. Control information for operation of the system can be provided in the form of menus or other displays which can be used by the operator during normal operation of the system. LCD display 1822 interfaces with system board 1801 via LCD controller 1857. Although the embodiment illustrated in FIG. 16 utilizes an LCD display, other types of displays can be utilized including, for example, a CRT type display. In addition to key pad 1821, input devices such as a mouse, joystick, or other data entry or control device can be utilized.

Power supply board 1803 is used to control and monitor the power provided to automated medication management system 300. Power supply board 1803 communicates with system board 1801 via power supply interface 1875 and includes a power supply monitor 1831, an AC power supply and charger 1832, a battery 1833, and voltage regulators 1834. Power supply board 1803 receives its source of power from a main power inlet 1818 and provides various system voltages 1898 to operate automated medication management system 300. AC power supply and charger, in combination with voltage regulators 1834, receives AC power from main power inlet 1818 and provides the necessary AC and/or DC voltages required to operate the system as system voltages 1898. Additionally, AC power supply and charger 1832 provides a charging signal utilized to charge batteries 1833. Batteries 1833 provide an alternative source of power for automated medication management system 300 should the AC power source become unavailable, substandard, or otherwise inadequate. Power supply monitor 1831 monitors the condition of the AC power supply and charger 1832, battery 1833, and voltage regulators 1834 to determine the condition and integrity of power sources and the power being provided to automated medication management system 300. Power supply monitor 1831 utilizes this information to make decisions regarding the source of power for the system and to inform system board 1801 regarding the status of the power supply.

Status panel 1804 is used to provide status and additional information to a user or operator of the system. Status panel 1804 interfaces with system board 1801 via status panel interface 1880. Status panel 1804 includes an LED display and audio controller 1841 and an IrDA transceiver 1843. LED display and audio controller 1841 provides drivers for an LED display 1842 and a speaker 1819. In this manner, audio and visual information can be provided to the user regarding the status and operation of the system.

IrDA transceiver 1843 is used to communicate with an external device having an infrared communication transceiver. IrDA transceiver 1843 provides the necessary conversions between the infrared communications signal and electronic communications signal such that system board 1801 can communicate with a device having an infrared communication port. IrDA transceiver 1843 communicates with system board 1801 via IrDA interface 1885.

Fluid delivery module 1805 is a module responsible for controlling the admixture and delivery process. Fluid delivery module 1805 communicates with system board 1801 via fluid delivery module interface 1895. More specifically, an SMP interface 1845 is provided to return status information regarding the operation of fluid delivery module 1805.

Printer 1817, which interfaces with system board 1801 via printer interface 1870, is utilized to provide a hard copy printout of information relevant to the operation, maintenance and control of automated medication management system 300.

A bar code reader 1812 is utilized to read information coded in the form of optical bar codes. The information from a scanned bar code is provided to system board 1801 via bar code interface 1853. Bar code reader 1812 can be implemented using a hand-held bar code reading device which is easily positioned in proximity with the bar code to be scanned. Bar code reader 1812 can be hard wired or can have a wireless interface to bar code interface 1853. One form of bar code reader 1812 suitable for use with automated medication management system 300 is the type of hand-held bar code reader often seen at the checkout line of many retail establishments.

Auxiliary FDM port 1813 which interfaces with system board 1801 via auxiliary FDM interface 1858 is utilized to provide communications with one or more auxiliary fluid delivery modules. As such, system board 1801 can be utilized to provide control and operation of a plurality of fluid delivery modules. Serial port 1814 and network connection 1815 are utilized to provide communications interface with external entities. Serial port 1814 can be an RS-232 or other serial communications port and interfaces with system board 1801 via external serial interface 1859. Network connection 1815 typically operates at a higher data rate than serial port 1814, and is utilized to connect system board 1801 to a network. In the embodiment illustrated in FIG. 16, the network connection is made by way of a PCMCIA interface 1861. a PCMCIA interface is desirable due to its small size and low power consumption features. However, as will be apparent to one of ordinary skill in the relevant art, the network connection need not be of the PCMCIA variety. Extended memory 1816, utilized to store data, is also interfaced with system board 1801 via PCMCIA interface 1861. Various components of system board 1801 are connected via system ADC lines 1862. In one embodiment, system ADC lines 1862 are a conventional bus structure having address, data and control lines, as well as control logic necessary for the operation thereof.

This architecture presented in FIG. 16 is described to provide a detailed example of one possible implementation of an architecture for automated medication management system 300. After reading this description, it will be apparent to one of ordinary skill in the art how automated medication management system 300 can be implemented using alternative architectures and that the implementation of an automated medication management system in accordance with the invention is not limited to the architecture depicted in FIG. 16. Additionally, numerous features and components of an automated medication management system are described elsewhere in this document and are not illustrated as being implemented in the example architecture illustrated in FIG. 16. However, it will likewise be apparent to one of ordinary skill in the art how these additional components and/or features can be implemented in conjunction with this or an alternative architecture.

Automated Health Care Environment

Figure 17:
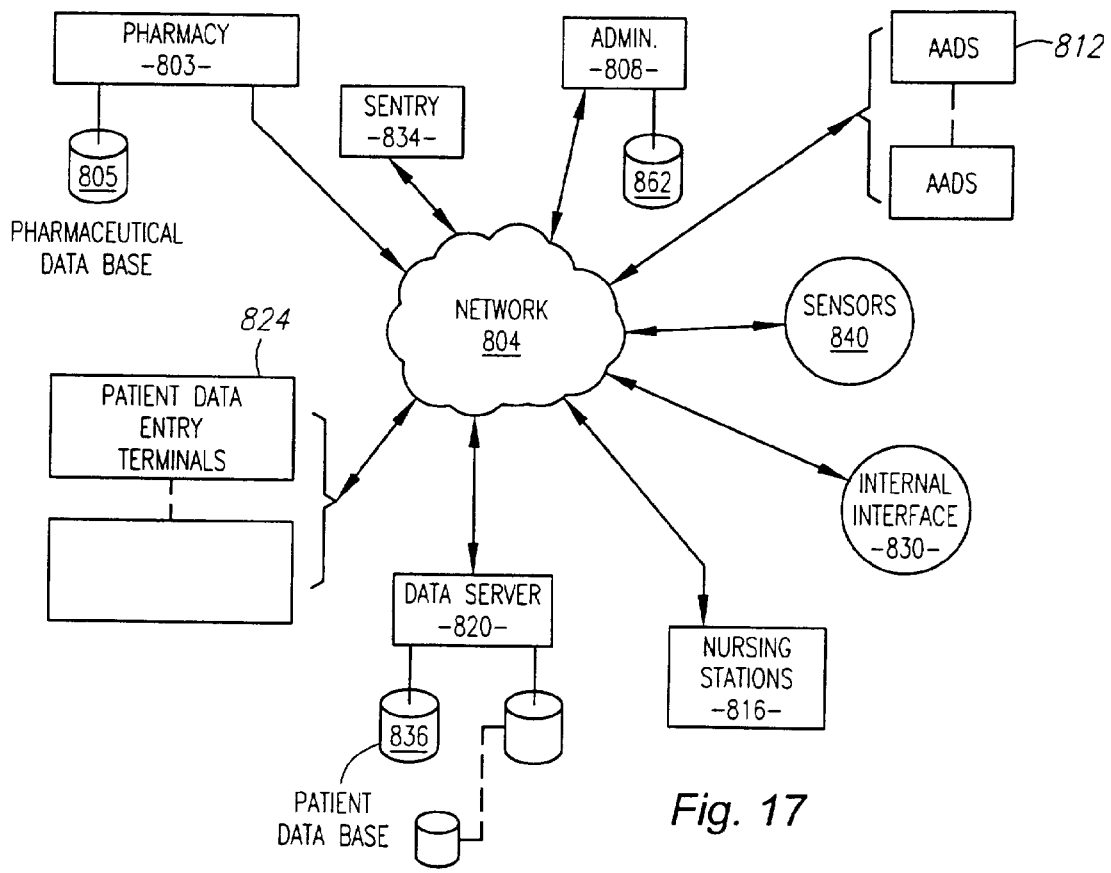
FIG. 17 is a diagram illustrating an example implementation of an automated health care facility according to one embodiment.

As discussed above, the automated medication management system 300, in accordance with one or more embodiments, can be integrated with a health care facility through a network or other communication means. FIG. 17 is a diagram illustrating an example implementation an automated health care facility 800 according to one embodiment of the invention. As will be apparent to one of ordinary skill in the art after reading this description, numerous alternative architectures can be used to implement the health care facility and provide the described functionality.

The automated health care facility 800 in this embodiment includes a network 804 which is used to integrate the various components of the health care facility. Network 804 can be implemented using local-area or wide-area network technologies and can be a single network as illustrated in FIG. 17, or can comprise a plurality of interconnected networks. Alternative techniques for interconnecting the elements of automated health care facility 800 can be utilized as well.

The health care facility illustrated in the example embodiment of FIG. 17, includes one or more pharmacies 803, one or more administration entities 808, one or more automated medication management systems 300, one or more nursing stations 816, one or more sentries 834 one or more data servers 820, and one or more data entry terminals 824. Also included in the illustrated embodiment are one or more external interfaces 830, as well as one or more automated admixture and delivery units 812.

As would be apparent to one of ordinary skill in the art after reading this description, additional facilities can be integrated with the network to provide additional functionality to suit the particular implementation of the health care system. Additionally, portions of the described facility which may not be needed for particular implementations can be omitted. Furthermore, alternative configurations can be implemented without departing from the spirit and scope of the invention.

The manner in which patient and medication information are handled in the health care facility is now described according to several example embodiments. As described above, health care professionals in the course of treating a patient often prescribe medication to be administered to the patient. This information can be entered into the system using data entry terminals, such as data entry terminals 824. These can be portable (such as, for example, hand held, or otherwise transportable) data entry terminals or stationary data entry terminals located at convenient locations for the entry of data. Additionally, clinicians and other health care professionals can use these terminals to enter other information germane to the treatment of the patient and his or her stay at the facility.

Examples of the types of data which can be entered in the data entry terminals 824 include patient information, medication information, and other information. Patient information can include, for example, the patient's vital signs, the patient's condition, patient allergies, existing patient medications, as well as other information which may be useful in the diagnosis or treatment of the patient. This patient information is ultimately stored on a patient database.

In a typical hospital or other health care environment, information pertaining to the patient's condition and the prescribed medications, dosage and dosing intervals are entered into the patient's chart. In one embodiment of the invention, this information is entered into a database containing patient information for one or more patients at the health care facility. This database is referred to in this document as a patient database. This database can include additional information about the patient such as other medications the patient may currently be taking, either intravenously, orally, or otherwise; allergies the patient may have; patient demographics, such as, for example, the patient's age, weight, sex, and other like information; or other relevant or pertinent information including other information from the patient's chart. All of the information normally found on the patient's chart may be stored in the patient database to create a "virtual chart" for the patient. This virtual chart can be linked by a communication interface to one or more entities or facilities such as a pharmacy and other facilities. In this manner, data from the chart can be accessed from multiple locations.

The data entry terminal can be a portable data entry terminal that can be carried or otherwise transported by a health care professional from patient to patient; or one which is stationary and located, for example at a central location or in the patient rooms.

In one embodiment, such information can also be entered using data entry device 312 in automated medication management system 300. In this embodiment, the information may be stored in automated medication management system 300 (such as, for example in data storage 316) as well as shared with other entities or databases through the use of communication interface 320.

Data entry terminals 824 can include a wired or wireless communication interface providing direct or networked connection to the one or more entities or facilities with which the terminal communicates. For example, a fixed data entry terminal 824 located in the patient's room or near the patient, can have a hard-wired or wireless connection to network 804 so that information can be transmitted from data entry terminal 824 to the appropriate database or data server 820 or to pharmacy 803. The portable data entry terminal can include wireless or hard-wired communications as well.

Additionally, in one embodiment the portable data entry terminal can store entered data in a local memory as the health care professional is performing his or her rounds. In this embodiment, the health care professional may carry the portable data entry terminal 824 with him or her while conducting the rounds. As each patient is seen, examined or diagnosed, information pertaining to that patient obtained during the visit can be entered using the terminal. Such information can include the various types of patient information described in this document as well as a diagnosis of the patient and a prescription to treat the diagnosis.

At the completion of the rounds, or at other periodic intervals, the data can be downloaded from the data entry terminal to appropriate elements in the health care facility. For example, in the environment of the health care facility illustrated in FIG. 17, a prescription may be forwarded to pharmacy 803, patient information may be stored in patient database 836, and so on. This can be done by wireless communications or by interfacing the portable data entry terminal to a hard-wired connection such as, for example, an RS232 port or a network interface card.

Additionally, the communications between data entry terminals 824 and other network elements or other health care facility entities can be continuous (e.g., via an open channel of communication) or frequent enough such that the health care professional interacts with these entities and elements in real time. In this manner the health care professional can receive feedback from these entities and elements as data is entered. For example, where a physician enters a prescription for a patient, the physician can receive real-time feedback regarding the propriety of administering the prescribed medication to the patient. As another example, where the physician enters a patient diagnosis and utilizes an analysis package to recommend treatments, the physician can receive real-time feedback. As illustrated by these two examples, in this embodiment, the physician can make on-the-spot decisions regarding therapies prescribed for the patient.

In the embodiment illustrated in FIG. 17, a patient database 836 is used to store the patient data information entered from patient data entry terminals 824. From the data regarding a patient, patient profiles can be created to provide a synopsis of pertinent information pertaining to the patient. Thus, the patient database can include detailed information regarding each patient as well as patient profiles.

In the embodiment illustrated in FIG. 17, a patient database 836 is illustrated as being accessed by a data server 820. In alternative embodiments, patient database 836 can be located elsewhere within the architecture or distributed among a plurality of locations.

A pharmaceutical database 805 is provided to store information relating to one or more of the medications dispensed by the pharmacy. This information can include drug IV template and other information such as drug interaction precautions, recommended doses, side effects, warnings and other information which may be relevant to a decision regarding whether to administer the prescribed medication. Pharmaceutical database 805 can also include a hospital formulary list indicating the medications available to that pharmacy or for the hospital to which the patient is admitted.

Although illustrated as directly tied to pharmacy 804, pharmaceutical database 805 can alternatively be located elsewhere within the architecture or accessed by a server, such as, for example, data server 820 or distributed among several entities.

In one embodiment, sensors 840 can be used to monitor a patient's vital signs and condition and to provide telemetry regarding the sensed patient information to update patient database 836. Additionally, information from sensors 840 can be used to provide information directly to the nursing stations 816. Examples of sensors 840 can include heart rate, blood pressure, body temperature, and other sensors to sense a patient's condition. Sensors 840 can be hard wired to the network or other device or can use a wireless communication interface. Sensors 840 are illustrated as being interfaced directly to network 804. Alternatively, sensors 840 can be interfaced via one or more entities, such as, for example, data entry terminals 824.

In one embodiment, when prescription information is entered into data entry terminal 824 (or via data entry device 312), the prescription is forwarded to the pharmacy 804. The delivery can be fully automatic, that is, delivery happens without further user intervention, or a command may be required to actually forward the prescription to pharmacy 804. Pharmacy 804 can include display screens, printers, terminals or other devices to provide the prescription information to the pharmacist. Patient and other information can be provided to the Pharmacist as well. Upon receipt of this information, the pharmacist fills the prescription.

Prescriptions sent to pharmacy 840 can also include an identification of the patient. According to one embodiment, patient database 836 is checked in conjunction with the prescription to determine whether the patient has any allergies, conditions, or other factors which may indicate that the prescribed medication is not ideally suited to that patient. This check can be used to help prevent the prescription and administration of medications to a patient where that patient has a condition which renders the medication unsuitable for that patient or where the patient has already been prescribe the same or another medication to treat the current condition. This check can be performed by comparing the prescription information with information stored in patient database 836. A simple example of such a check would be to look into patient database 836 to determine whether the patient is allergic to the prescribed medicine.

Additionally, the prescribed medication and information regarding the patient and his or her condition in patient database 836 can be compared against pharmaceutical database 805 to determine whether the patient has any conditions or there are other circumstances which would give reason to reexamine the decision to prescribe the identified medication.

Such a check can be performed as the physician enters the prescription information into data entry terminals 824, and thereby provide real time feedback to the health care professional. At this point, the health care professional can decide whether to proceed with the original prescription, performing a preemptive override of future alarms if necessary, change the prescription, or perform further investigation, examination, tests, or studies to determine the appropriateness of the prescribed therapy.

This check can also be performed by pharmacy 804, automated medication management system 300, or other entity having access to this information. In one embodiment a sentry 834 is provided specifically to perform this medication-error-prevention function. In this embodiment, sentry 834 is a dedicated device which examines one or more of patient information, patient profiles, prescription information, and pharmaceutical information to determine whether the prescribed medication, dosage, and dosing interval are appropriate. Again, this can be done in real-time to provide immediate feedback, or offline.

Once a prescription is checked to determine whether it is appropriate a message can be generated and provided to various elements of the health care facility. For example, where real-time feedback is provided to the prescribing physician, a message may be sent indicating the prescription was entered and accepted; or that the system has determined the prescription to be inappropriate and the reasons why such a determination has been made, and perhaps suggestions of alternative therapies to be prescribed. Such messages can assist the physician in making decisions regarding the treatment of patients.

Administration 808 can utilize information obtained by a network 804 to enhance and further automate the administration functions performed by the health care facility. For example, administration 808 can use drug event information and patient information to update its billing records; maintain and manage inventory; schedule the availability of operating rooms, hospital beds, diagnostic and/or treatment equipment; and schedule or manage the use of other health care facilities. Additionally, it may be desired to have pharmacy 804 maintain its own inventory, especially for critically controlled substances. Thus, in one embodiment, certain inventories can be performed by administration 808 and others by pharmacy 804.

Administration 808 can have its own dedicated databases 862, or can utilize databases interfaced to data server 820. Additionally, administration 808 can draw data from existing databases serving other network entities.

Automated admixture and delivery systems 812 can retrieve information from and provide information to network 804. As described above, in one embodiment, automated admixture and delivery systems 812 can be relocated and interfaced to network 804 as needed for data transfers. For example, automated admixture and delivery systems 812 can be moved from one patient to the next to deliver medication. In one embodiment, an example implementation of an automated admixture and delivery system 812 can be an automated medication management system 300.

Data server 820 can be used to provide interface to one or more databases such as, for example, patient database 836. Other databases as needed or desired can be interfaced via data server 820 to network 804. Additionally, in an alternative configuration from that illustrated in FIG. 17, databases such as pharmaceutical database 805 and administration database 862 can be accessed via data server 820. As will be apparent to one of ordinary skill in the art after reading this description, data server 820 and its associated database can use mirroring, shadowing, or other techniques to provide redundancy as a safeguard against lost or tainted data.

Nursing stations 816 can be provided at various points throughout the health care facility to provide a location for nurses, clinicians, and other health care professional to enter data into network 804 or to retrieve data from network 804. In one embodiment, nursing stations 816 are implemented using a PC or other small computer with a network interface. Alternatively, they can be implemented using a terminal with a keyboard, mouse and monitor. Data entry devices such as, for example, a bar code reader may be provided as well. a nursing station 816 implemented with data entry capabilities can be used as an alternative (or in addition to) data entry terminals 824 to enter patient and other information.

Additionally, a printer may be provided at nursing stations 816 to provide hard copy printouts for use in the treatment of patients and the administration of the health care facility. Additionally, a printer at nursing stations 816 can be used to create and print bar code labels to be used for things such a patient identification and other identification tasks. Printed labels can be provided with a sticky back so that they can be affixed to the patient's chart, or other items appropriate for identification.

In one embodiment, nursing station 816 includes a port for interfacing to the portable data entry terminals. In this embodiment, the health care professional interfaces the portable data entry terminal with the nursing station to download data to network 804.

External interface 830 can be used to provide an interface for network 804 to the outside world. Such an interface can be used to contact suppliers for supply information and ordering, to provide information to health care professionals outside of the hospital, and for other communication interfaces.

The automated health care facility can also include an analysis feature to assist the health care professional, such as the tending physician for example, in determining a suitable medication to prescribe for the patient based information such as patient information, medication information, and other information which may be relevant. In this aspect of the invention, an analysis package is provided which considers a diagnosis of the patient, patient information from the database as well as information pertaining to the medications available in a designated pharmacy to suggest to the physician which medications may be appropriate to administer to the patient, and at what dosage levels and intervals. The package may provide list of alternative medications which can be used to treat the diagnosed condition and may also recommend alternative treatments or therapies as well.

According to this analysis package, the system accepts the diagnosis of the patient as entered by the physician and checks the pharmaceutical database to determine which medications available in the formulary may be appropriate to treat the diagnosed condition. In one embodiment, the system may also recommend medications not in the hospital formulary.

Medication information available in one or more databases, such as, for example IV template information described below, is used to suggest recommended dosage levels and intervals to the physician for the suggested medications. The prescription analysis feature may also use other patient information to assist in the decision making process, such as, for example, patient allergies, patient demographics, other patient medications, or other patient information provided in the patient database or entered by the physician.

The analysis package may rule out certain medications or highlight other medications based on this additional patient information. The analysis package may also recommend specific dosage levels based on the patient information. According to another aspect of the analysis package, the system may prompt the physician to enter additional information to aid in the decision making process. For example, consider a scenario where the patient's weight is not available in the patient database and this information is desired to accurately determine the dosage level. The system may ask the physician to enter the patient's weight into the system. Ideally, however, all of the patient's key information is already entered into the system or otherwise available from a database.

In one embodiment, the analysis package also provides the health care professional with additional information pertaining to the recommended medications. For example, the physician may request a list of side effects for a recommended medication. This information can be used to assist the physician in the decision-making process as well as to allow the physician to pass this information on to the patient.

This additional information, such as side effects and other information can also be provided to other professionals such as the health care professional administering the medication. In this manner, the administering clinician can inform the patient of likely side-effects at the time of administration.

In one embodiment, such information can be provided to health care professionals at a terminal such as a data entry terminal 824 and can be protected based on clearance levels.

Additionally, links may be provided to on-line references and documents or to references and documents available on the Internet, for example, to provide the health care professional with quick and easy access to available on-line resources. For example, CD-ROM or other electronic versions of the *Physicians Desk Reference* or other documents may be provided and linked for access via data entry terminals 824 or other terminals.

FIG. 17 provides a representative functional architecture for the health care facility. As would be apparent to one of ordinary skill in the relevant art after reading this description, the functionalities described herein can be distributed among entities in alternative architectures.

Example Architecture For An Order Entry Terminal

Figure 18:
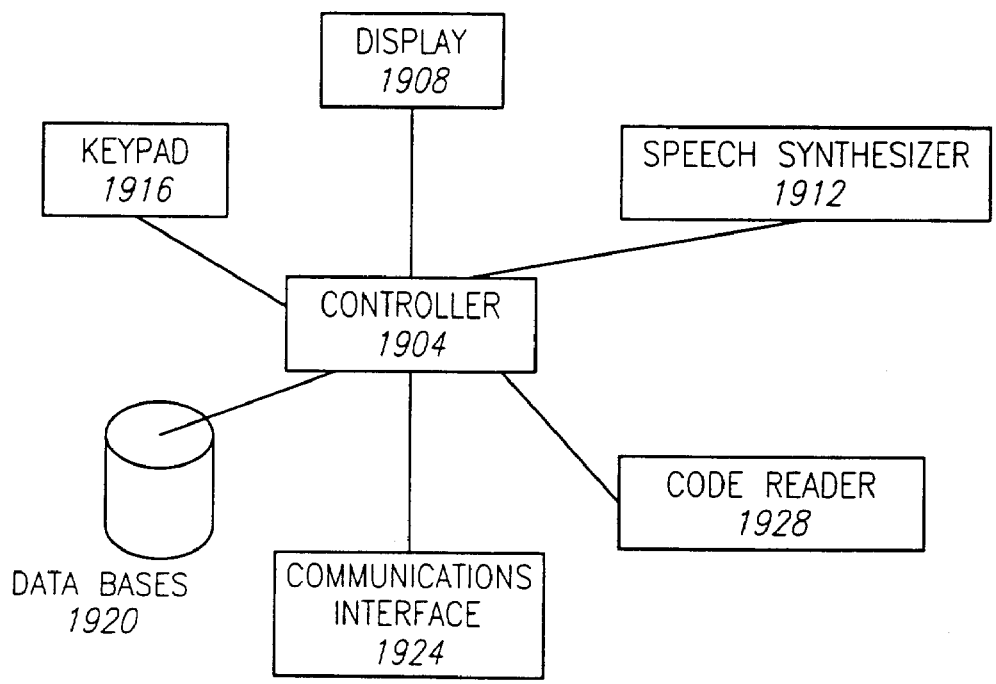
FIG. 18 is a diagram illustrating an example architecture for a data entry terminal according to one embodiment.

FIG. 18 is a diagram illustrating an example architecture for a data entry terminal 824 according to one embodiment of the invention. Data entry terminal 824 in this embodiment includes a controller 1904, which controls the operation of the terminal. Controller 1904 may be implemented, for example as a microprocessor or other processor-based system.

A display 1908 and appropriate display drivers (not illustrated) can be used to provide messages to the user. Display 1908 can be implemented using, for example, an LCD display, an active matrix display, a CRT or other display device. Other indicators, such as, for example, LED's or other indicator lights can be used as well.

A speech synthesizer 1912 can be provided to compose vocal messages to be provided to the user. Both the display and the vocal messages can be used to prompt the user for input, inform the user of medication alerts or provide other messages to the user. For a hand-held device, a smaller display, such as an LCD display may be desired. For a larger device, a partial or full size CRT screen will provide more area for display.

In an embodiment where the physician enters a diagnosis and the system provides suggestions regarding possible medications to prescribe, information regarding those medications and links to other references, a larger screen may be more desirable, although not required.

Keypad 1916 can be used to provide data entry to the user. Keypad can be numeric or alphanumeric and can include function keys or other special keys. Alternatively a full keyboard and mouse or other pointing device can be provided. In a hand-held device, it is generally desirable to use a smaller keyboard or even a keypad. For a stationary terminal a full keyboard provides additional flexibility.

Databases 1920 are illustrated as a part of data entry terminal 824. As discussed above, patient and/or medication information can be stored locally. In alternative embodiments, databases 1920 are not required and the data is retrieved by communications interface 1924.

Processing of information to perform prescription checks or prescription analysis can be performed locally, for example by controller 1904, or remotely by sentry 834, pharmacy 803 or other processing element.

Communications interface 1924 provides uni- or bi-directional communications with other entities. Interface 1924 can be a serial or parallel interface and can be wired or wireless. Peripherals 1932 can be interfaced to the terminal as well, including printers, disk drives and other devices.

A code reader 1928, such as for example, a bar code reader, magnetic code reader, or other reader may be interfaced as illustrated. Code reader can be integrated with the terminal or in a separate housing.

The integrated embodiment is ideal for the hand-held implementation. In the integrated embodiment, the reader may be disposed in the housing of the terminal with a window or other "receiver" positioned, for example, at the top edge of the terminal or on the bottom side of the terminal. In this manner, the hand-held terminal can be held up to the bar code, or magnetic stripe or other code and read the code. No wires or separate housings are required.

For an embodiment where the reader is separate, the reader may be hand-held and moved about freely such that the scanner can be positioned to read codes. The reader may be either wired or wireless. Either version, and particularly the wireless version, may have internal storage to allow storage of read data and downloading via batch transfers.

As would be apparent to one skilled in the art after reading this description, alternative architectures can be provided for implementing data entry terminals 824.

Hardware And Software Implementations

Figure 19:
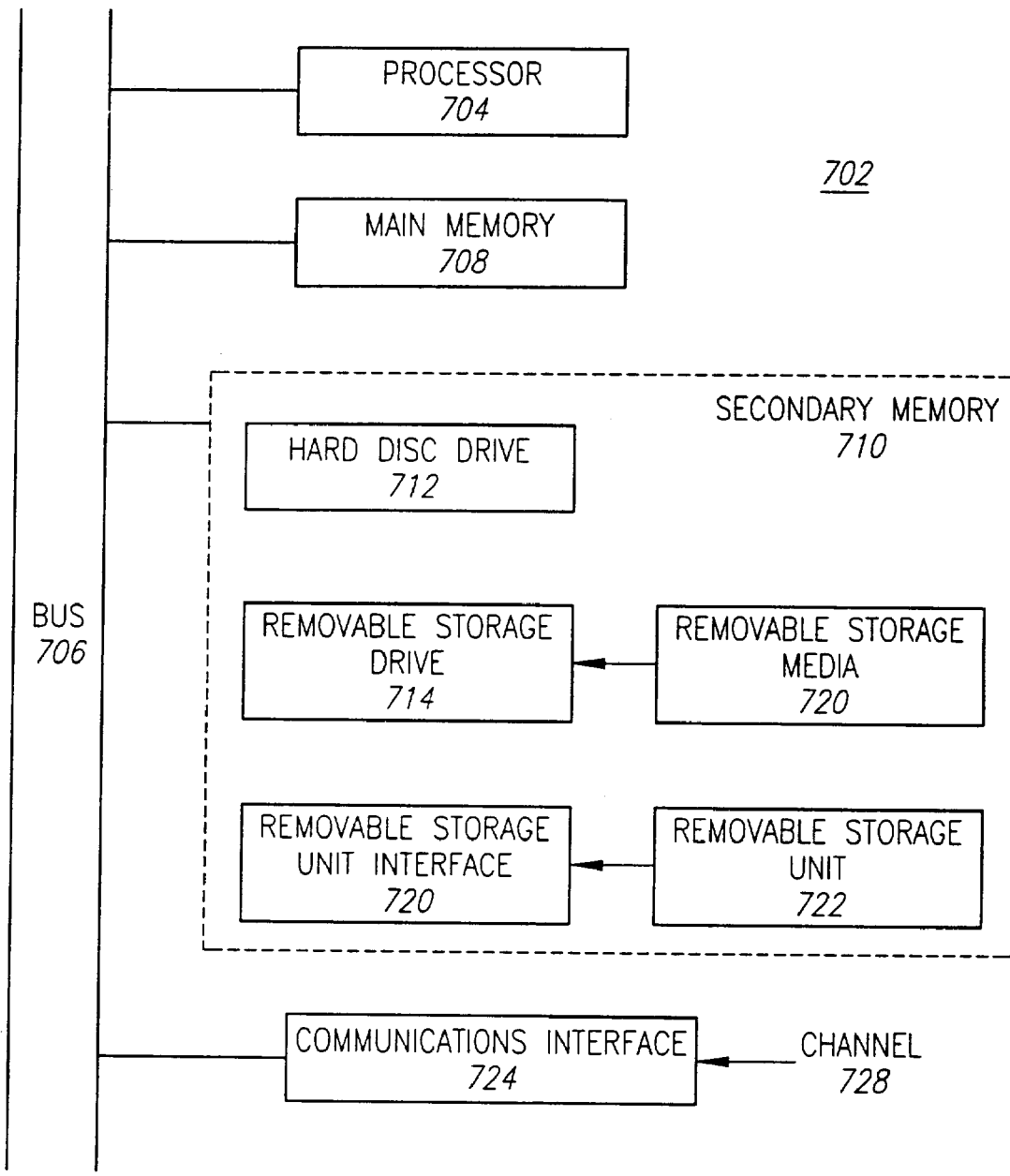
FIG. 19 is a diagram illustrating an example hardware and/or software implementation of elements of the invention according to one embodiment.

The various devices, components, and entities described above and illustrated in block diagram form may be implemented using hardware, software or a combination thereof and may be implemented in a computer system or other processing system. In fact, in one embodiment, these elements are implemented using a computer system capable of carrying out the functionality described with respect thereto. An example computer system 702 is shown in FIG. 19. The computer system 702 includes one or more processors, such as processor 704. The processor 704 is connected to a communication bus 706. Various software embodiments are described in terms of this example computer system. After reading this description, it will become apparent to a person skilled in the relevant art how to implement the invention using other computer systems and/or computer architectures.

Computer system 702 also includes a main memory 708, preferably random access memory (RAM), and can also include a secondary memory 710. The secondary memory 710 can include, for example, a hard disk drive 712 and/or a removable storage drive 714, representing a floppy disk drive, a magnetic tape drive, an optical disk drive, etc. The removable storage drive 714 reads from and/or writes to a removable storage medium 718 in a well known manner. Removable storage media 718, represents a floppy disk, magnetic tape, optical disk, etc. which is read by and written to by removable storage drive 714. As will be appreciated, the removable storage media 718 includes a computer usable storage medium having stored therein computer software and/or data.

In alternative embodiments, secondary memory 710 may include other similar means for allowing computer programs or other instructions to be loaded into computer system 702. Such means can include, for example, a removable storage unit 722 and an interface 720. Examples of such can include a program cartridge and cartridge interface (such as that found in video game devices), a removable memory chip (such as an EPROM, or PROM) and associated socket, and other removable storage units 722 and interfaces 720 which allow software and data to be transferred from the removable storage unit 718 to computer system 702.

Computer system 702 can also include a communications interface 724. Communications interface 724 allows software and data to be transferred between computer system 702 and external devices. Examples of communications interface 724 can include a modem, a network interface (such as an Ethernet card), a communications port, a PCMCIA slot and card, etc. Software and data transferred via communications interface 724 are in the form of signals which can be electronic, electromagnetic, optical or other signals capable of being received by communications interface 724. These signals are provided to communications interface via a channel 728. This channel 728 carries signals and can be implemented using a wireless medium, wire or cable, fiber optics, or other communications medium. Some examples of a channel can include a phone line, a cellular phone link, an RF link, a network interface, and other communications channels.

In this document, the terms "computer program medium" and "computer usable medium" are used to generally refer to media such as removable storage device 718, a hard disk installed in hard disk drive 712, and signals on channel 728. These computer program products are means for providing software to computer system 702.

Computer programs (also called computer control logic) are stored in main memory and/or secondary memory 710. Computer programs can also be received via communications interface 724. Such computer programs, when executed, enable the computer system 702 to perform the features of the present invention as discussed herein. In particular, the computer programs, when executed, enable the processor 704 to perform the features of the present invention. Accordingly, such computer programs represent controllers of the computer system 702.

In an embodiment where the elements are implemented using software, the software may be stored in a computer program product and loaded into computer system 702 using removable storage drive 714, hard drive 712 or communications interface 724. The control logic (software), when executed by the processor 704, causes the processor 704 to perform the functions of the invention as described herein.

In another embodiment, the elements are implemented primarily in hardware using, for example, hardware components such as application specific integrated circuits (ASICs). Implementation of the hardware state machine so as to perform the functions described herein will be apparent to persons skilled in the relevant art(s).

In yet another embodiment, elements are implemented using a combination of both hardware and software.

IV TEMPLATES

In one embodiment, software is provided enabling the pharmacy to choose their formulary drugs and the respective drug delivery parameters from a comprehensive list of alternatives. One or more of the drugs in the formulary will preferably have a list of parametric limits associated with it. For example an IV template can contain the following fields of information relative to the mixing and delivery of a medication:

| Sample Template Fields | Contents |
| --- | --- |
| Diluent Exceptions | Diluents which are prohibited from being used with the specified drug |
| Additive Exceptions | Additives which are added to the IV solution source and are prohibited from being used with the specified drug |
| Maximum Delivery Rate | Maximum delivery rate set by the pharmicist for a specific drug |
| Maximum Dilution Volume | Maximum volume to be infused set by the pharmicist for a specific drug |
| Minimum Delivery Rate | Minimum delivery rate for the corresponding drug |
| Minimum Dilution Rate | Minimum volume to be infused for the corresponding drug |
| Nominal Delivery Rate | Delivery rate recommended by the pharmacy for the corresponding drug |
| Nominal Dilution Volume | Recommended volume to be infused by the pharmacy for the corresponding drug |
| Nominal Reconstitution Volume | Volume of diluent to be used in the reconstitution |
| Stability Time | Time which drug will remain stable after reconstituting and/or diluting |
| Drug Requiring Reconstitution | Indicate whether drug is powdered of lyphilized requiring reconstitution |

The pharmacy can then set the IV Template parameters to preferred values. Once the parameters are set for the medications in the hospital pharmacy formulary, the data can be imported via, for example, wired or wireless communication, or the network, into each bedside device where it is resident for dose administration, or in the data entry terminals where it is resident for prescription entry. When the hospital formulary is changed from time to time, the pharmacy may add or delete items from the pharmaceutical database.

As discussed above, automated medication management system 300 allows the clinician identify the drug and the diluent during setup via the bar code scanner or selection from a drop down menu or entry via other user interface. In one embodiment, the identified drug must match an item in the pharmaceutical database for the system to begin mixing and/or infusing. Once the match is made by the present invention, the recommended mixing and/or delivery parameters are displayed on the user interface for the clinician to review. The parameters can be changed by the clinician as long as the change conforms to the minimum and maximum recommendations set forth in the pharmaceutical database. If the change does not conform, the clinician is notified that the parameters are out of range. In one embodiment, administration of the medication will not be permitted to proceed unless a professional with the proper level of authorization allows the out of range delivery.

In the event that the IV solution source is prohibited according to the pharmaceutical database for an inappropriate diluent or incompatible additive, the clinician may be required to change the solution source container to an appropriate diluent with the proper additive. After changing the solution source container, the system automatically reprimes the fluid pathways with the new diluent prior to beginning the cycle.

INSTRUCTIONS FOR USE

In one embodiment, the general sequence of steps for the user to operate the automated medication management system for delivery of an IV drug, is as follows:

| SECTION | CONTENTS |
| --- | --- |
| 1. Instrument Preparation | Turn power on and load cassette and set if IV delivery is desired through the device |
| 2. Selecting the IV Source Solution | Identify Patient ID and Cilinician ID by bar code scan or keypad entry. Identify IV Source Solution by bar code scan or select from displayed list Select the prescribed base solution additives from the displayed list and enter the volume for each with the keypad |
| 3. Priming the Delivery Set | Press Prime key to automatically prime the proximal tubing and cassette Press and hold Prime key to prime the distal tubing |
| 4. Loading the Vial | Insert the vial into the adapter and press the vial on to the vial spike until the vial retention latch clicks into place. (The device will acknowledge that the vial is loaded properly and prompt user) The clinician is reminded to utilize aseptic techniques to avoid touch contamination of the vial spikes or luer port adapter. |
| 5. Scheduling Primary Delivery | Select the Primary Delivery key Enter the Rate and Volume To Be Delivered Enter time for delivery to begin (If there is a scheduling conflict the user will be prompted to change the start time) |
| 6. Scheduling a Vial Port | Press a Vial Port Key. Scan the vial bar code or select the drug from the displayed list. The IV Template information in the Pharmacy preset will be displayed. Clinician may change the delivery rate, duration of delivery and total dilution volume within the Pharmacy boundary limits. If the scheduled delivery time exceeds the respective Drug Stability time, the clinician will be prompted to change the delivery time. If there is an incompatibility with the IV Source Solution or Additives, the Clinician will be prompted to change the IV Source Solution container. After changing, the device will automatically reprime fluid pathways with new IV Source Solution. |

-continued

| SECTION | CONTENTS |
|---|---|
| Scheduling the Luer Port | Press the Luer Port key Scan the bar code or select the drug from the displayed list. The IV Template information in the Pharmacy preset will be displayed. Clinician may change the delivery rate, duration of delivery and total dilution volume within the Pharmacy boundary limits. |
| Starting Admixture and Delivery | After scheduling the ports, the clinician presses run and the fluid delivery cycle begins |

This sequence is provided as an example only to illustrate the operation of one embodiment of the invention. After reading this description, it will become apparent to one of ordinary skill in the art how alternative embodiments may be operated using alternative procedures.

Figure 20:
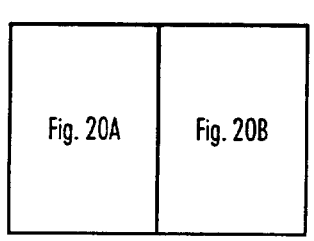
FIG. 20 is a flow chart illustrating a system start-up overview according to one embodiment of the invention.

FIG. 20 provides an overview of an example automated medication management system 300 according to one embodiment. After powering automated medication management system 300 on, if the system is connected to the network, the system checks the version of the software resident in the system with that available over the network. If the system's version does not match the version carried on the network, the system updates the version and operates off that new version.

The clinician enters a password to enable the system to unlock the front panel and display a start-up screen. The front panel lock feature can be set up by the health-care facility in a preference-setting section within the software so that after a timeout period of no activity has expired, the instrument automatically goes into front panel lock. This provides security against unauthorized use of automated medication management system 300. The user may also enter into front panel lock on a predetermined command.

After display of the startup screen, the clinician may press a number of different keypad buttons to access different routines. If any of the keypad buttons P, 1, 2, 3 or L are pressed, the system checks whether a cassette is loaded. Should a cassette be loaded and be uncompromised, the system proceeds to the cassette priming procedure, illustrated in FIG. 23.

Figure 21:
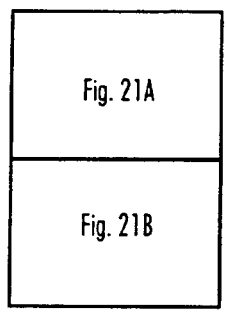
FIG. 21 is a flow chart illustrating a patient Identification routine according to one embodiment of the invention.

FIG. 21 illustrates a Patient ID Routine according to one embodiment. This routine describes a sequence of events for identifying the patient to automated medication management system 300. Whether this feature is enabled can be determined by the health care facility. If the patient identification feature is not desired, the system exits this subroutine immediately. Should patient ID be desired, the system checks to see if the patient ID has already been entered. If it has not already been entered, it can now be entered via bar code, or it can be entered via keypad entry. The identification can be in the form of the patient ID number or the patient's name or other code. This information can be used for accessing one or more databases to pull the patient profile information or other patient information. By accessing such data, automated medication management system 300 can perform medication error checking.

Figure 22:
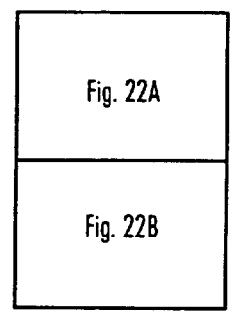
FIG. 22 is a flow chart illustrating a clinician ID routine according to one embodiment of the invention.

FIG. 22 illustrates a Clinician ID Routine according to one embodiment of the invention. The clinician ID routine is analogous to that performed for the patient ID as described above with reference to FIG. 21. Clinician ID is performed according to facility preference. Should a health care facility prefer to track information based on a particular clinician's actions, the identification feature can be enabled. The system can accept a barcode or a keypad entry of the clinician's ID, name, PIN or other identifiers.

Figure 23:
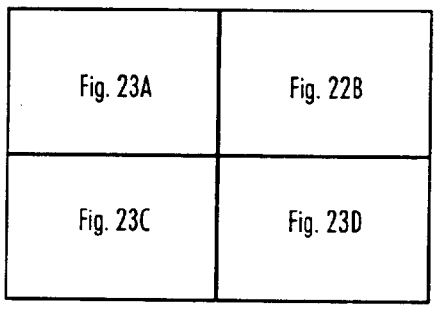
FIG. 23 is a flow chart illustrating a cassette loading and priming routine according to one embodiment of the invention.

FIG. 23 illustrates a cassette loading and priming procedure according to one embodiment. After a clinician opens and closes both the inner and the outer door, the system determines whether a cassette 77 is in place. In one embodiment, should cassette 77 be present and have been used before, it will have been irreversibly compromised by operation of the two shut-off valves or by some other means. If the cassette is not compromised, then the clinician may proceed to the cassette priming sequence. If any of the P, 1, 2, 3 or L buttons are pressed on the keypad, the system checks to determine whether a cassette 77 is in place. If no cassette 77 is in place, automated medication management system 300 prompts the clinician to install the cassette and performs a check for a compromised cassette.

Once cassette 77 is loaded, the system prompts the clinician to identify the primary solutions for administration by either bar code scan of the solution container label, or to enter in all the components of that solution via a set of lists that are supplied in the user interface. Should the patient profile or other patient information be available, the system checks the solution being administered versus what was actually prescribed. Should the system find no errors, it initiates "automatic priming." The user is prompted to press "OK," and then the system automatically primes the cassette from the bag all the way to the distal exit port. At this point, the system then initiates a manual priming sequence, which is a user-activated and controlled sequence. The system prompts the user to press and hold a prime button until the user sees fluid coming out the distal end of the tube, at which point the user releases the button.

Figure 31:
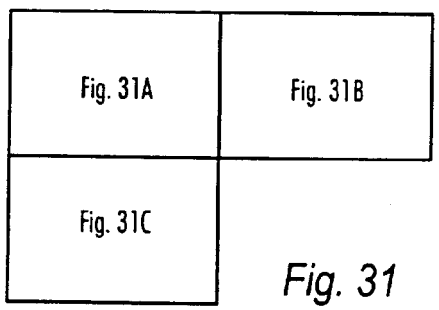
FIG. 31 is a flow chart illustrating a primary IV setup according to one embodiment of the invention.

Once the cassette is properly primed, the user can press P, 1, 2, 3, or L. Automated medication management system 300 begins the programming sequence the selected port. For example, in FIG. 31, the P button has been pressed. This indicates that the primary solution delivery, or the primary port, is about to be programmed. When the primary button is pressed, programming of that port is initiated. All parameters that have been previously entered appear for modification or verification and approval. Empty data fields such as rate of delivery or the volume to be infused (VTBI) can be entered. Required data fields, as determined by the hospital, must be completed. Upon entry of the necessary data, the user is prompted to approve the entries by pressing OK. When "OK" is pressed, the port is programmed and the programmed operation is initiated.

Figure 32A:
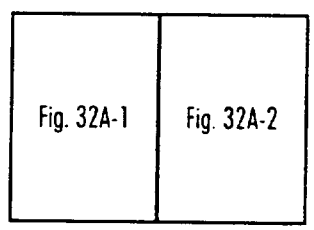
FIGS. 32A and 32B are a flow chart illustrating a vial port programming routine according to one embodiment of the invention.
Figure 32B:
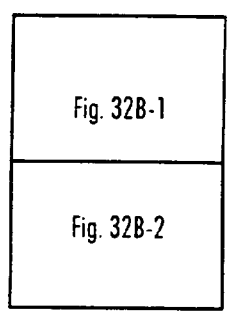

FIGS. 32A and 32B are flow diagrams illustrating programming of ports 1, 2, and 3 according to one embodiment. Ports 1, 2, and 3, are the vial attachment ports. When a port button is pressed, the instrument prompts the user to identify the drug by either scanning the bar code of the drug vial, or selecting the drug from the drugs that are listed in the current Patient Profile (networked), or by use of a larger drop down list. If the drug is selected from the comprehensive list and not from the patient profile, the drug name is again displayed for verification. This action forces a review of the planned action for correctness of drug and patient, and helps to reduce medication errors.

If the drug was identified via a bar code scan, the bar-code-scanned drug can be checked against data such as the patient profile. If the drug is present on the patient profile list the user is allowed to proceed. If not present, the user is notified of the situation and asked to review their planned action for correctness of drug and patient. The user is also asked if they still wish to proceed.

Figure 24:
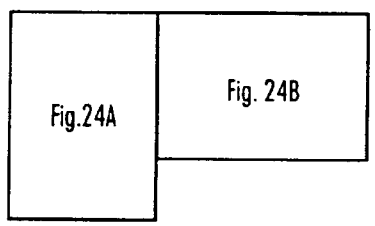
FIG. 24 is a flow chart illustrating a vial attachment routine according to one embodiment of the invention.

Once the drug has been identified, and verified against the patient profile, and/or accepted by the user, the instrument references the IV templates. Information in the IV templates includes the final dilution volume, the diluent the drug will be put into, solutions this drug is compatible or incompatible with, suggested rates of delivery, reconstitution volumes, and other data elements important to the safe delivery of this drug. The user can confirm those settings or make modifications to fields where permitted. Once this programming is complete, the instrument checks the drug to primary solution compatibility. If the drug and solution are compatible, all the programming is done and the instrument prompts the user to attach the drug vial to the port, this is Vial Attachment Routine, illustrated in FIG. 24.

The Vial Attachment Routine Flowchart highlights two levels of sensing on the vial attachment mechanism. The ability to sense whether the vial loading mechanism is up or down, and the ability to detect whether the vial attachment locking mechanism is locked or unlocked. These sensing mechanisms enable the instrument to monitor ports that are being manipulated to notify the user of the appropriateness of their actions. If the vial lock mechanism was moved from the locked to the unlocked position on an incorrect port, the instrument warns the user of the consequences of proceeding and the user is able to recover from that situation.

Once the vial has been correctly attached, the user is instructed to schedule the delivery of this medication as illustrated on charts 24 and 25. The ability to schedule medication for delivery in advance is a key feature of the device. In one embodiment, the delivery can be scheduled as much as 24 hours in advance.

Figure 33:
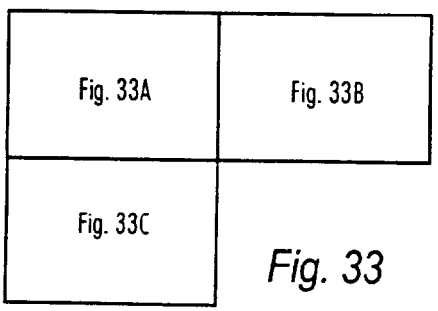
FIG. 33 is a flow chart illustrating a drug to diluent incompatibility and special diluent requirement routine according to one embodiment of the invention.

A drug to diluent incompatibility process, illustrated in FIG. 33, demonstrates a process the instrument and user go through if it is determined that the drug and the primary solution (diluent) are incompatible. In this situation, if the solution is incompatible with the drug, the instrument first looks at port L to see whether it is available for use. If port L is not already programmed for use, the instrument suggests a different solution source to be attached to that port for use with this drug when it is time to deliver that drug. If the Luer port is active and in use, the system suggests that the user schedule the incompatible drug to be delivered at some later time.

Figure 35A:
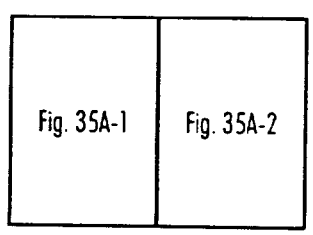
FIGS. 35A, 35B, and 35C are a flow chart illustrating a luer port programming routine according to one embodiment of the invention.
Figure 35B:
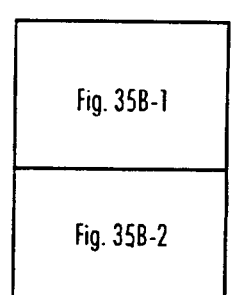
Figure 20A:
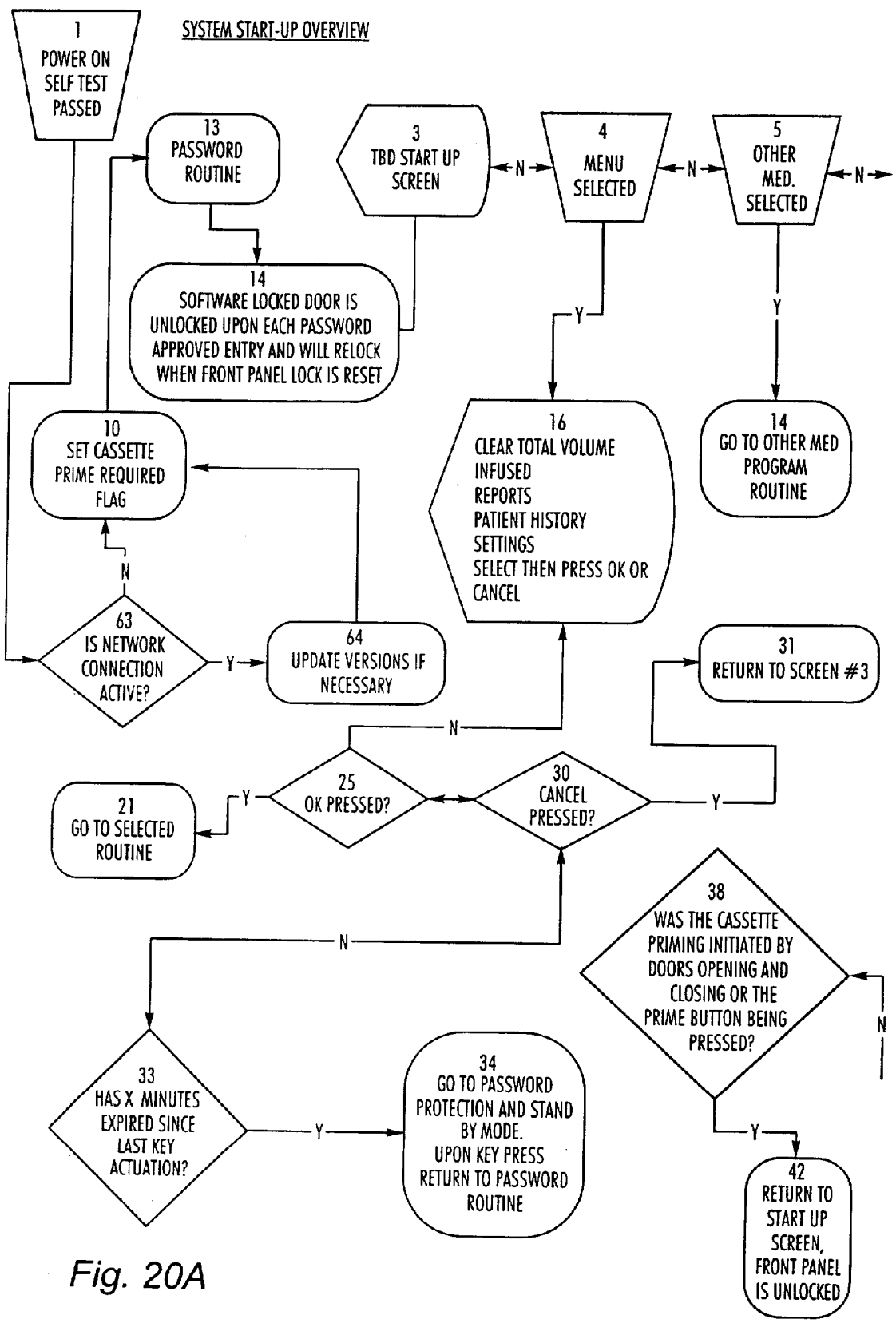
Figure 20B:
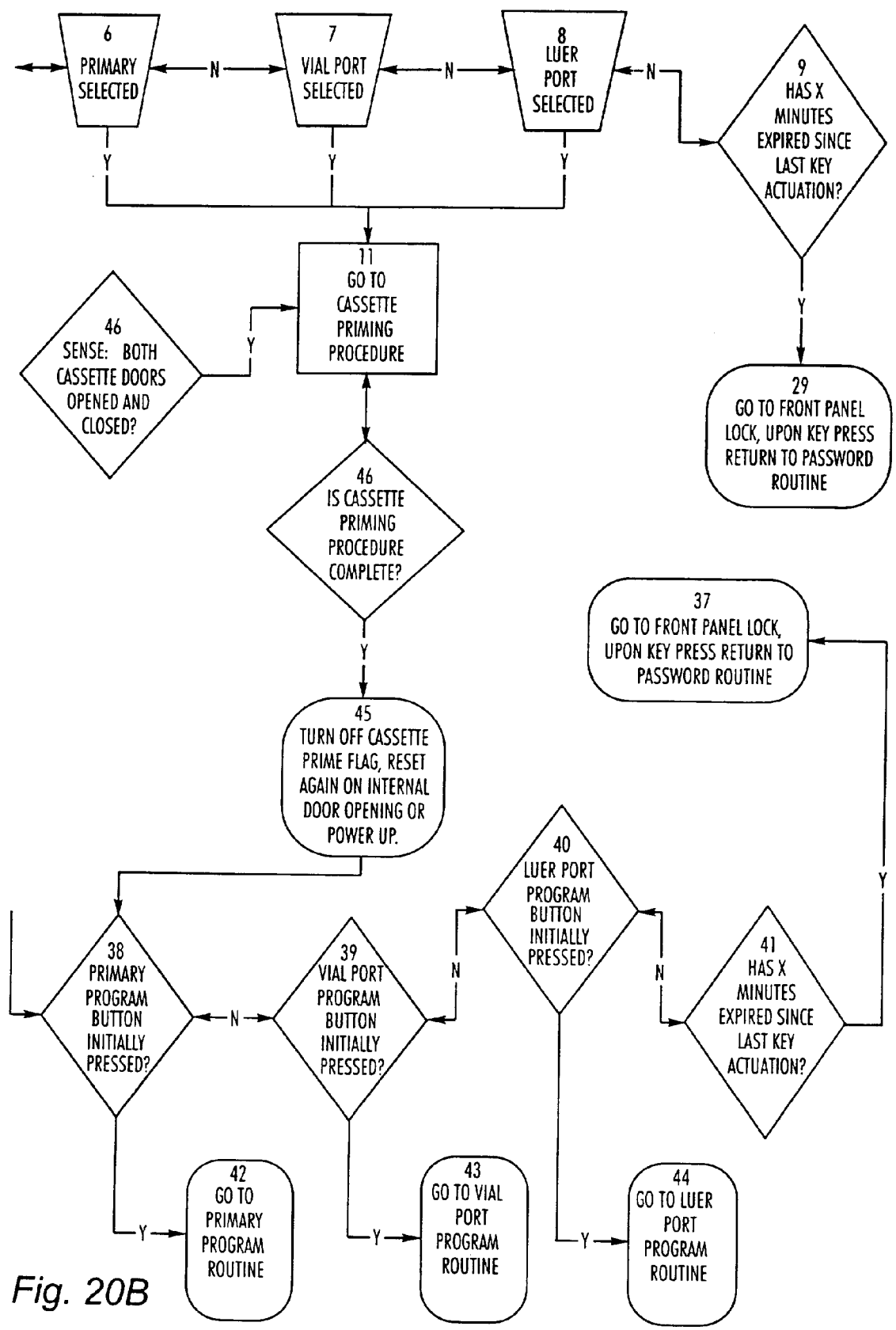
Figure 21A:
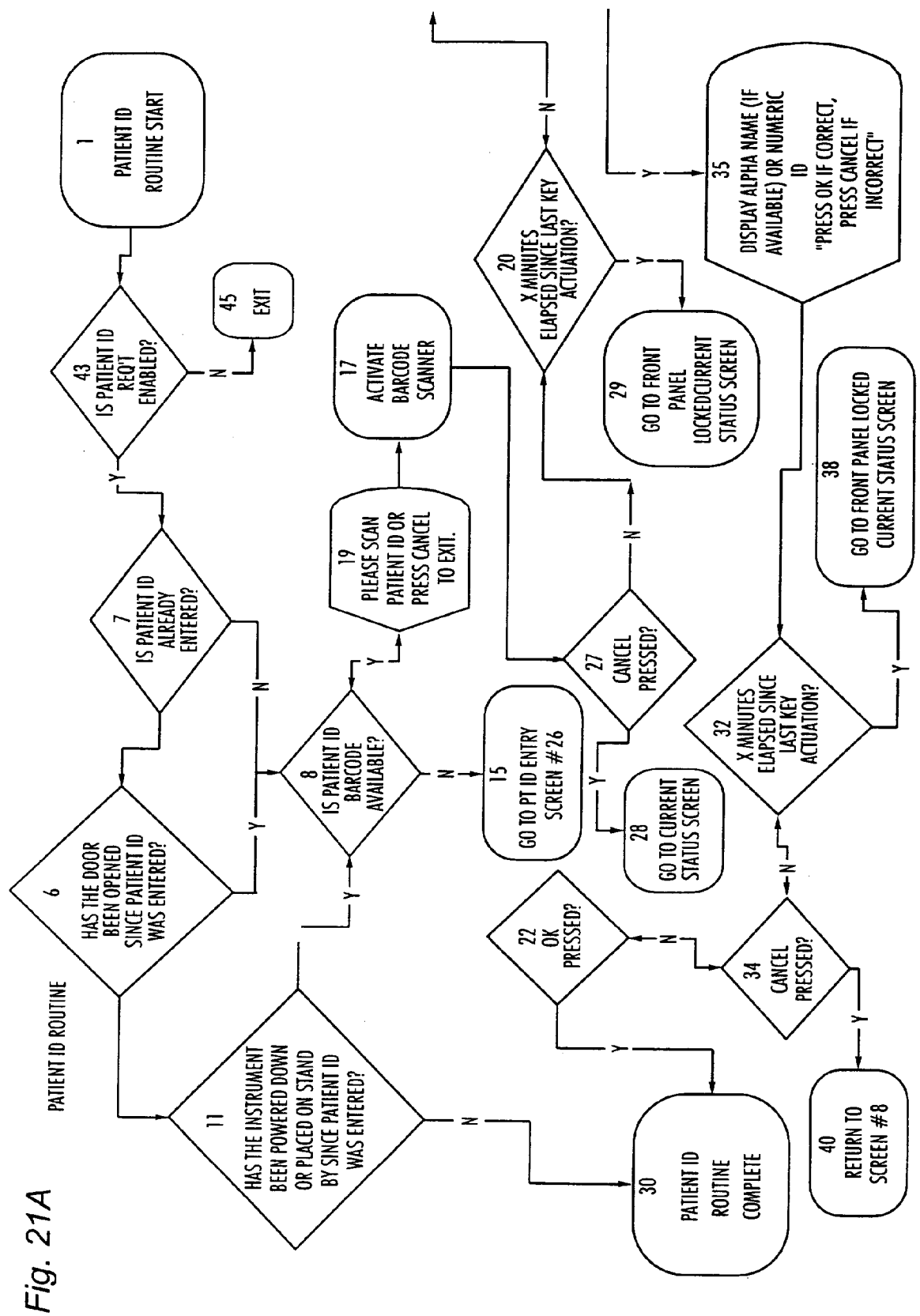
Figure 21B:
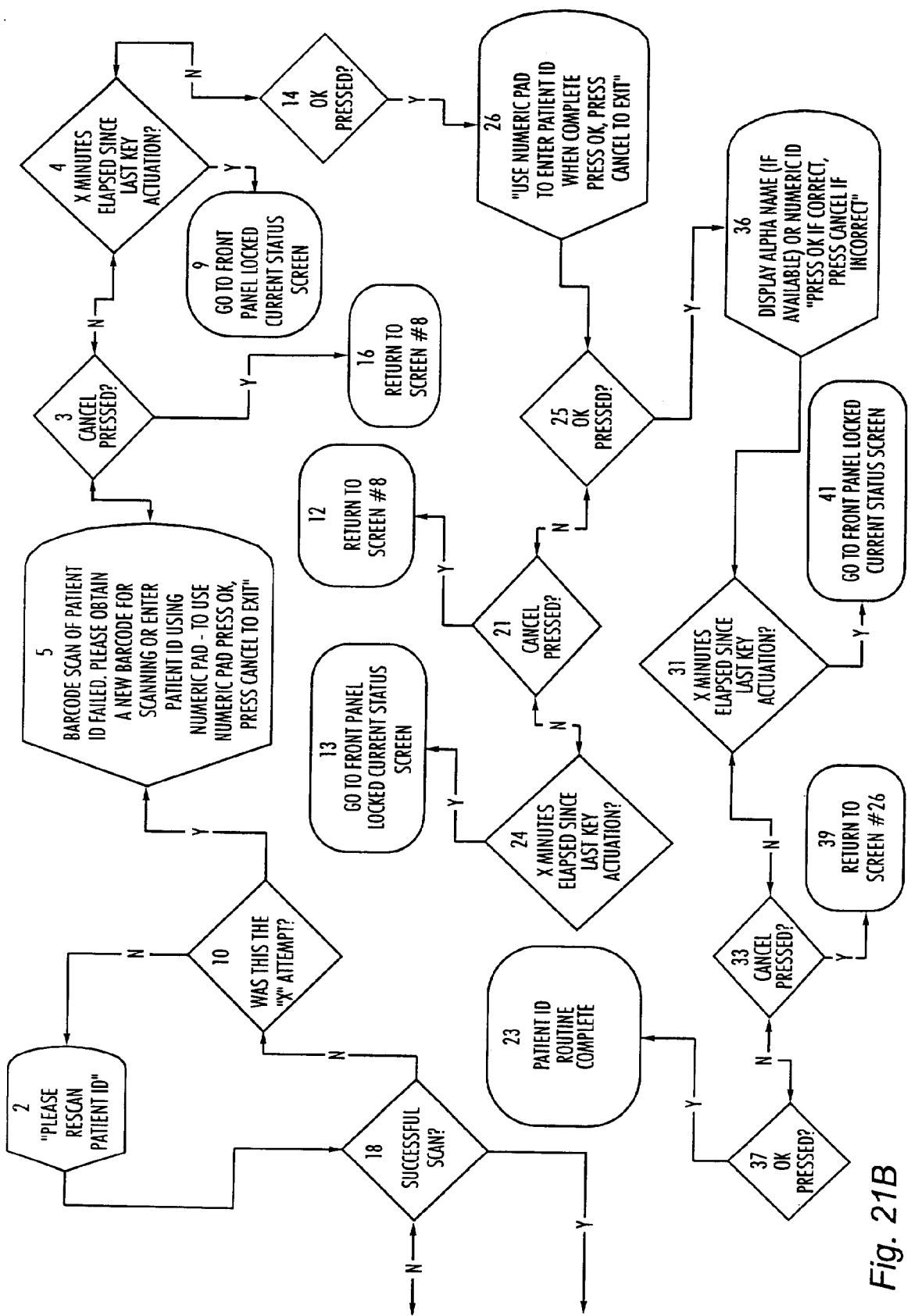
Figure 22A:
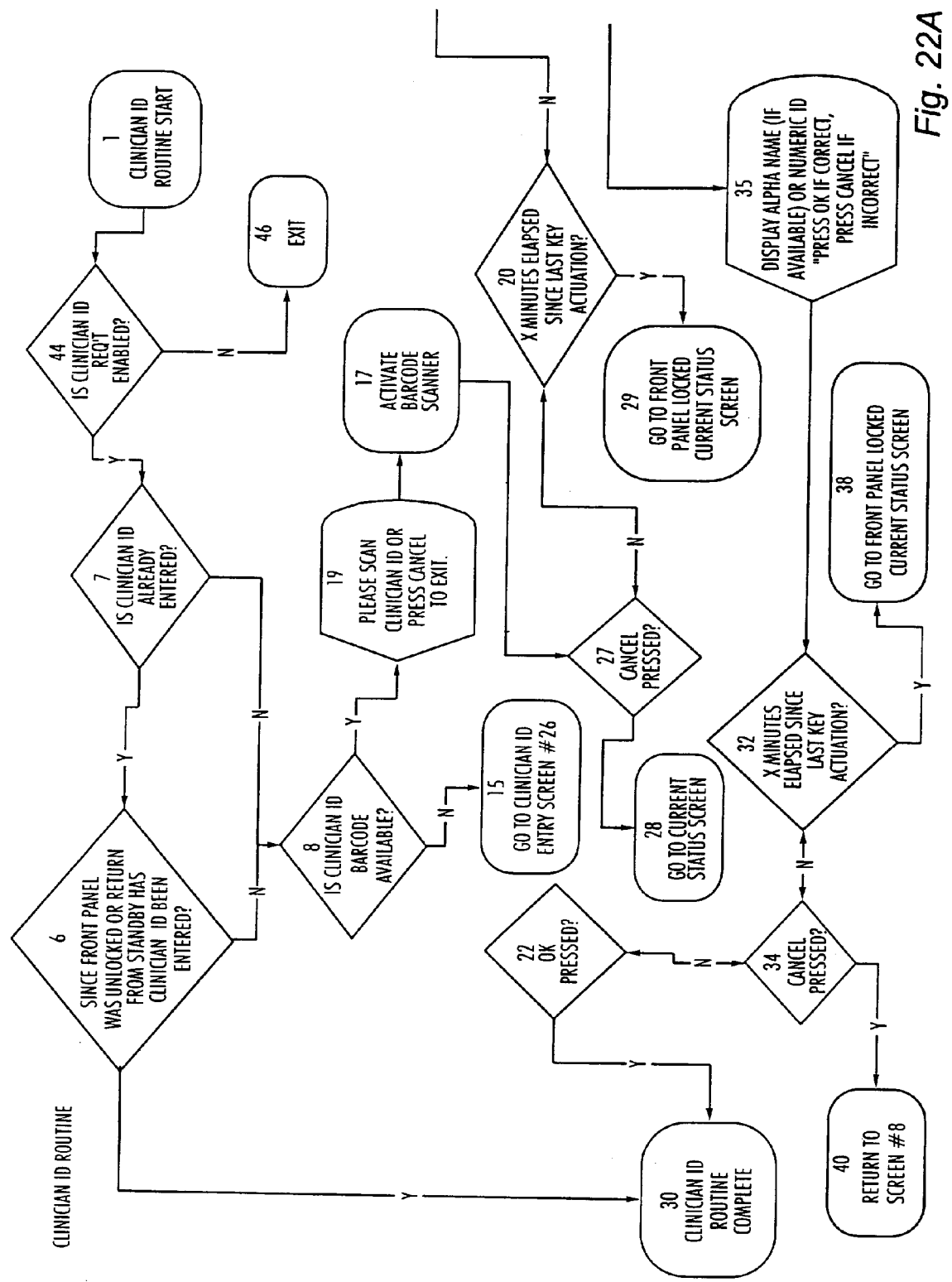
Figure 22B:
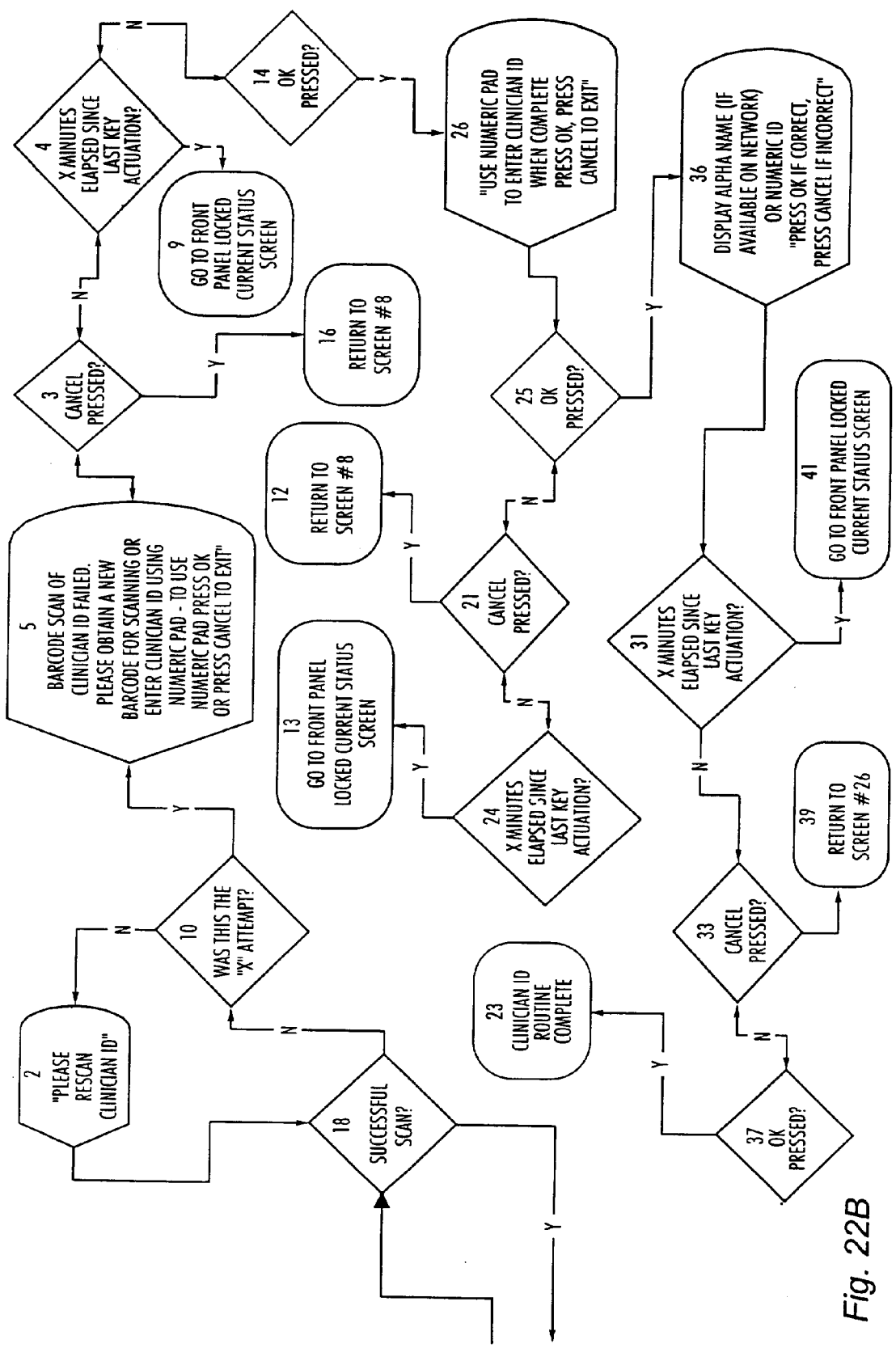
Figure 23A:
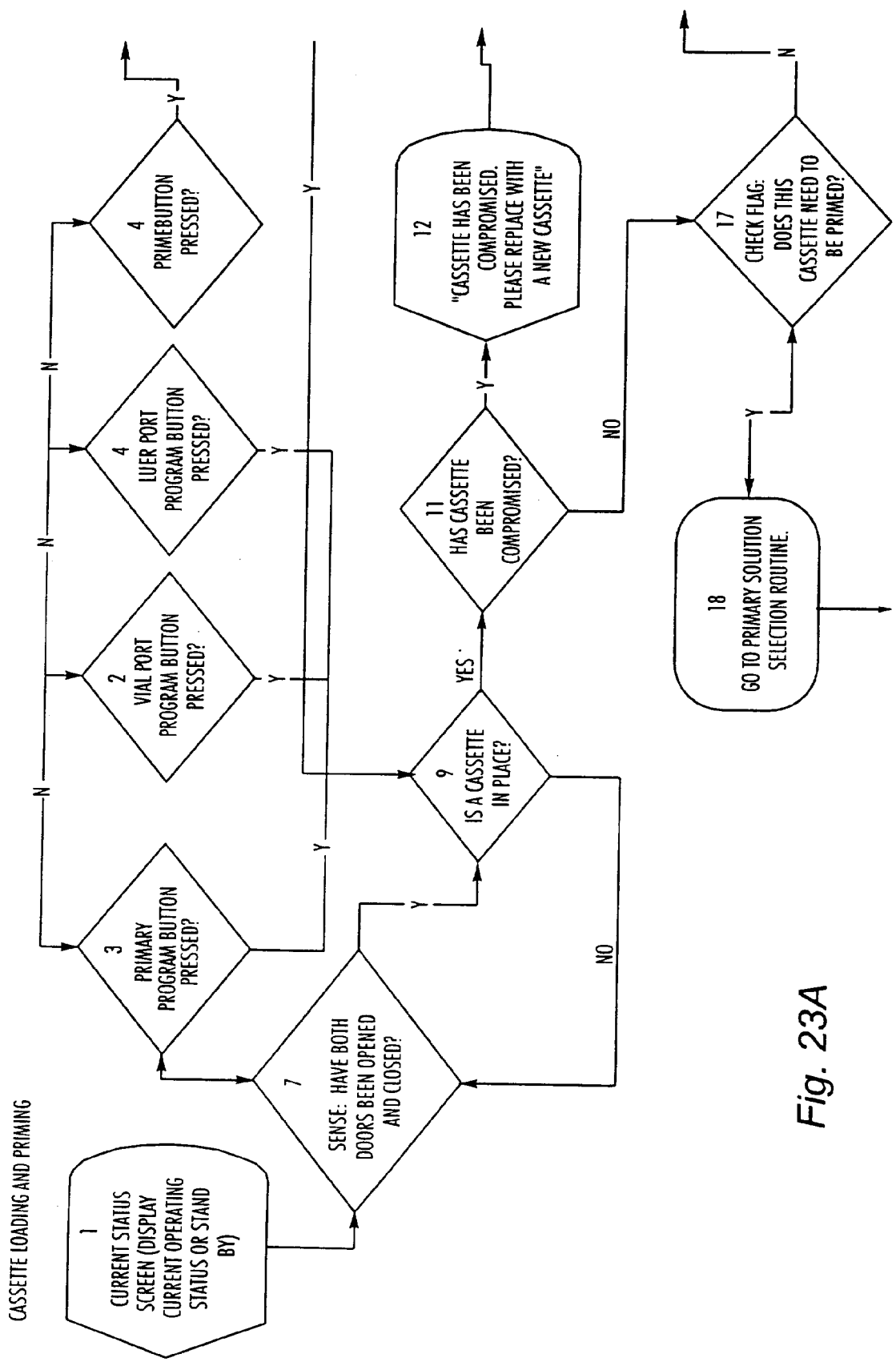
Figure 23B:
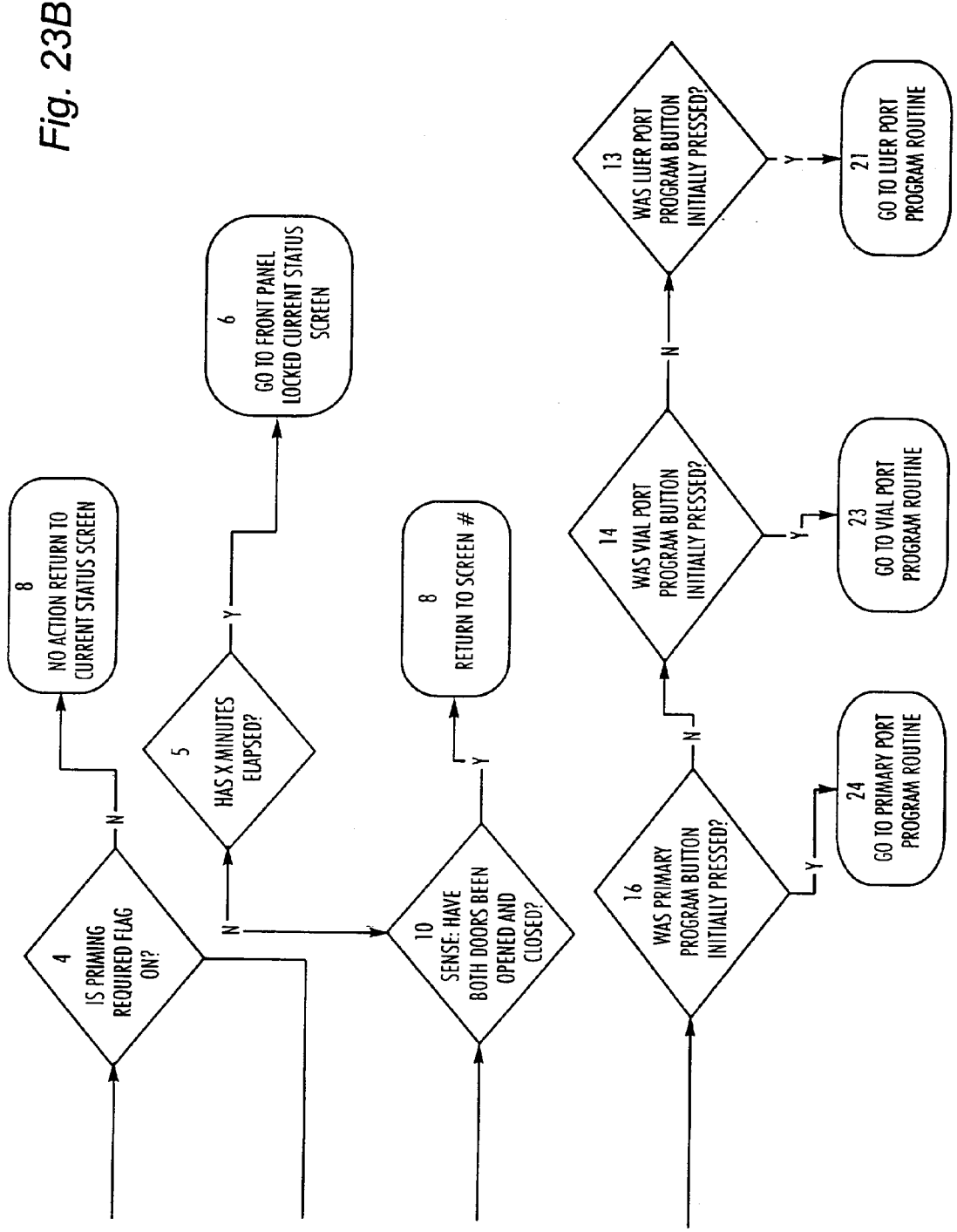
Figure 23C:
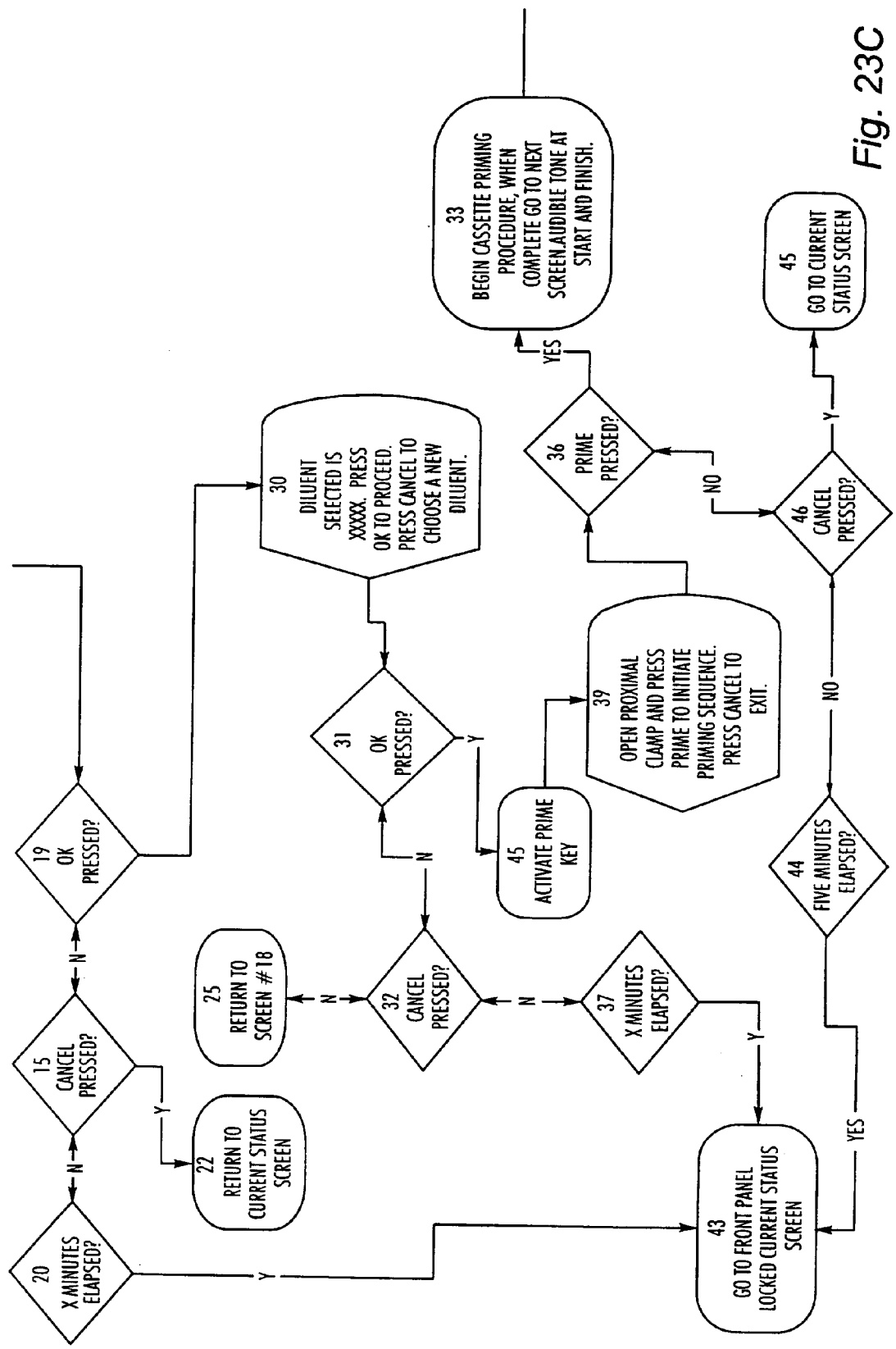
Figure 23D:
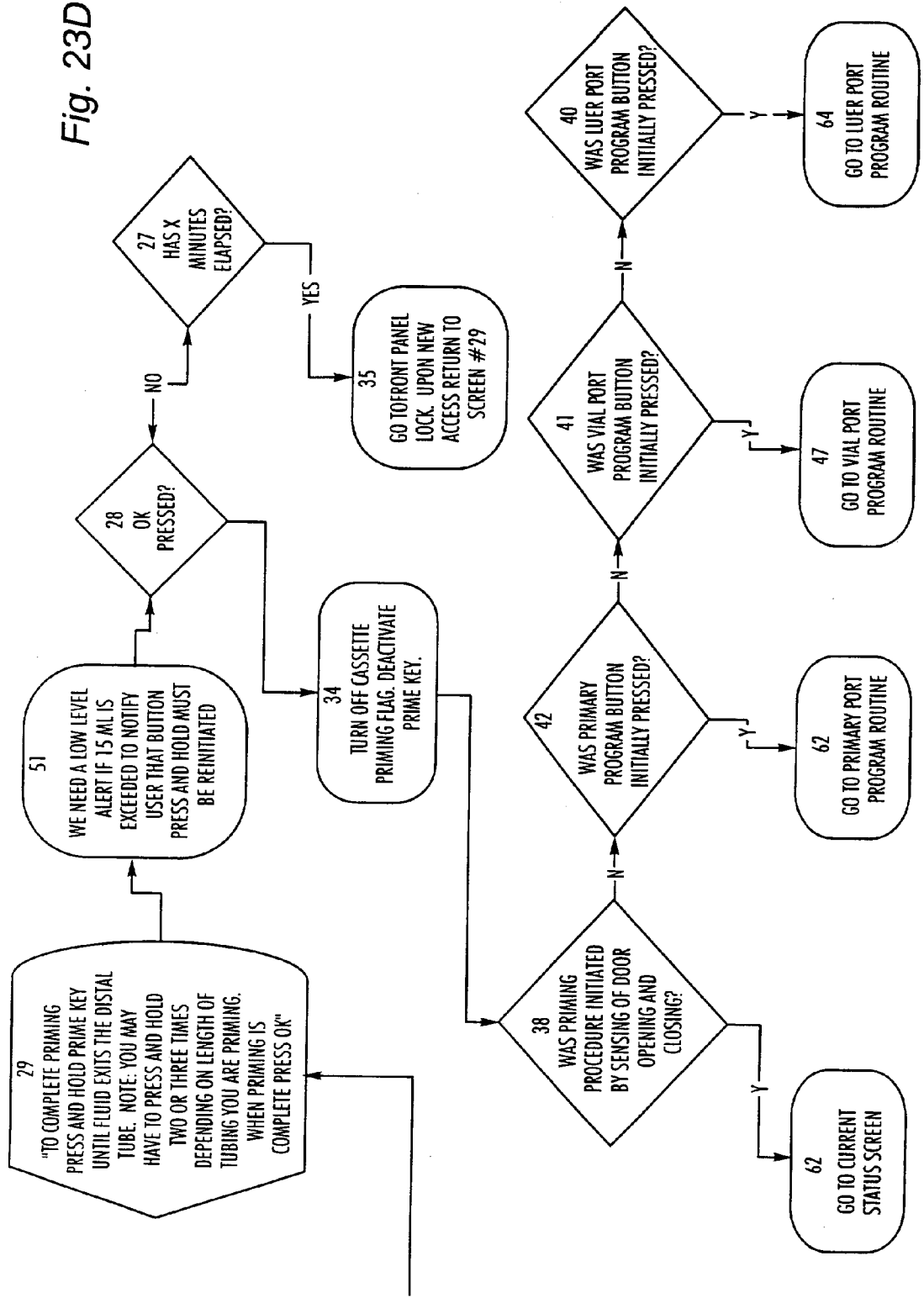
Figure 24A:
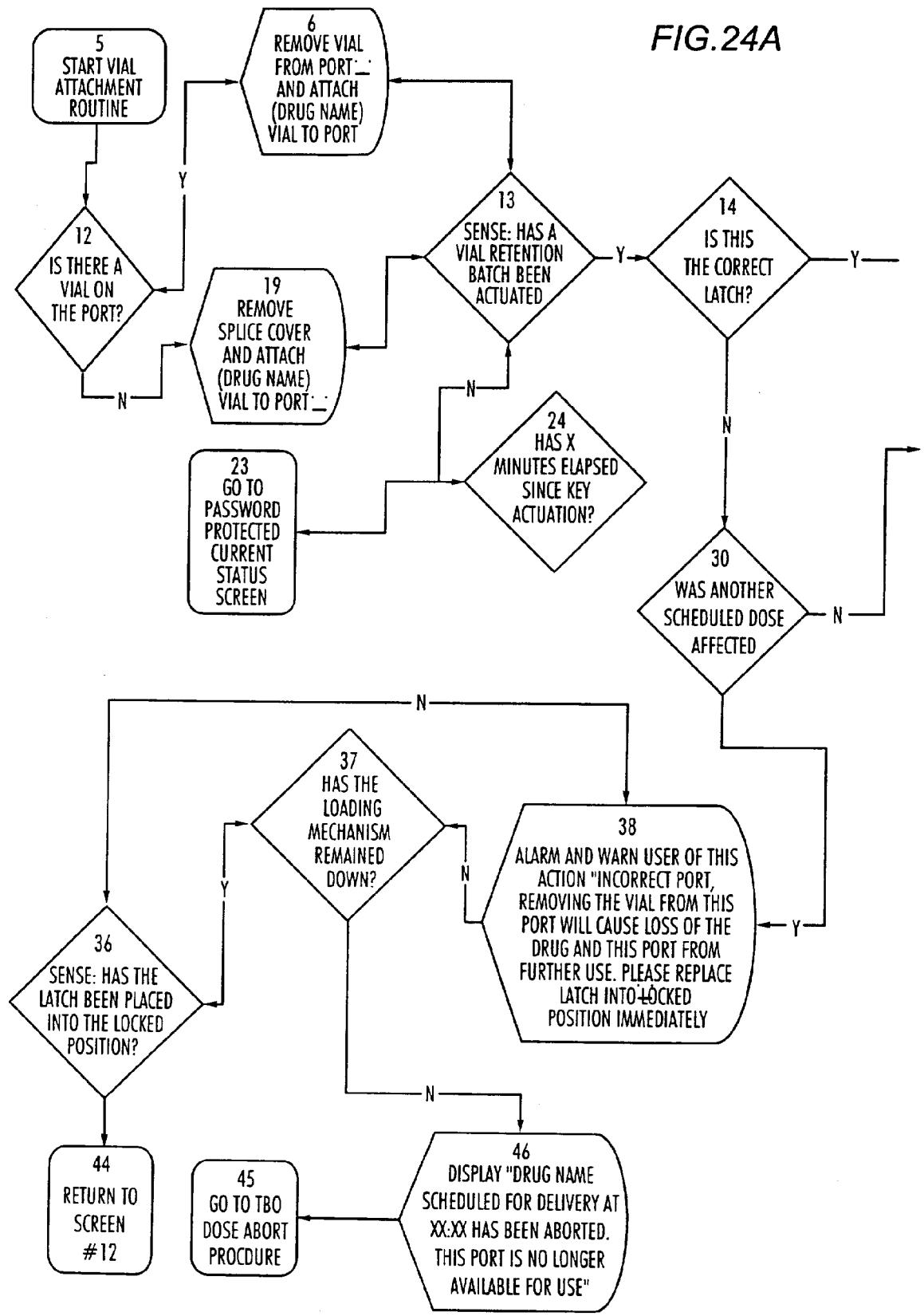
Figure 24B:
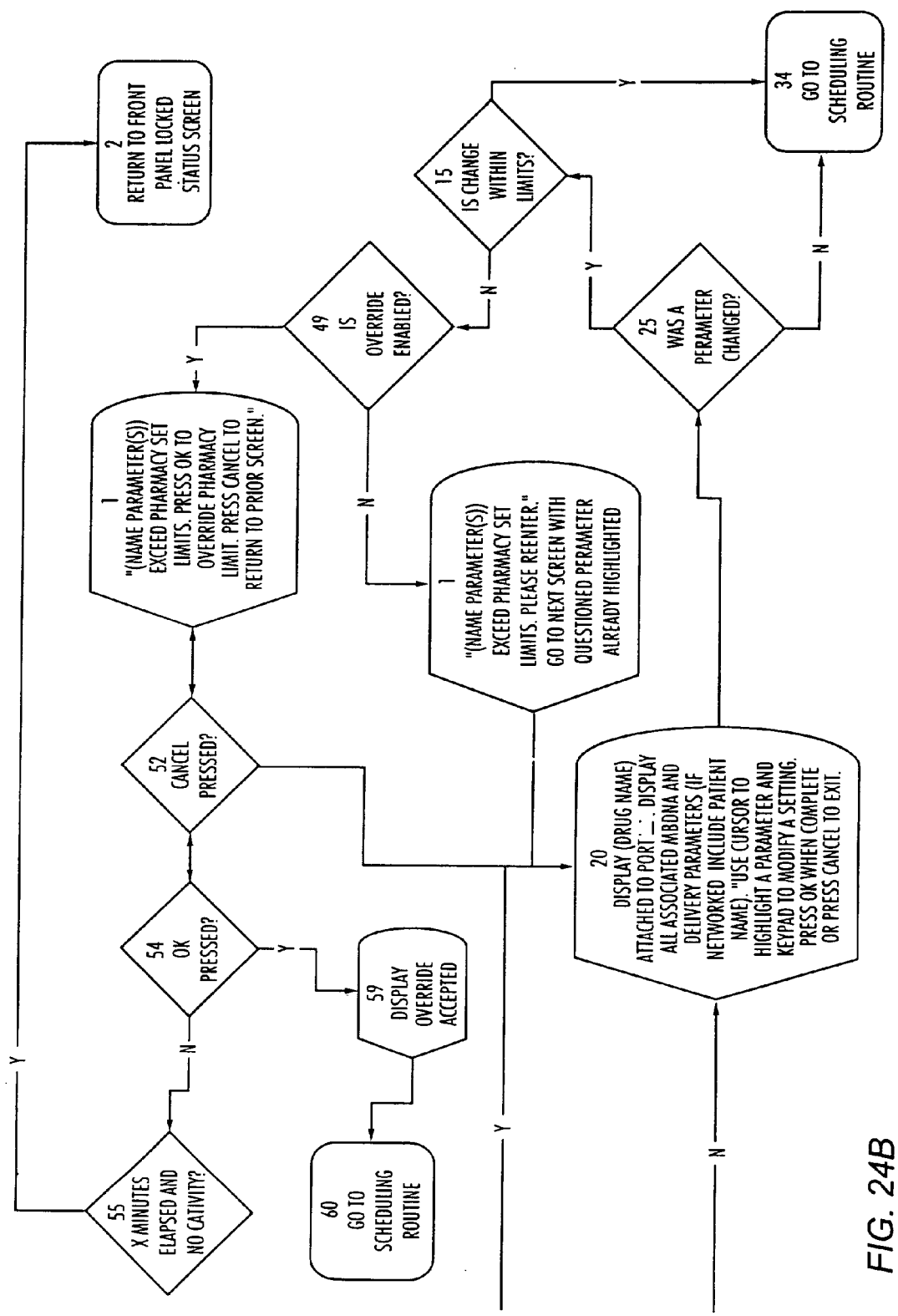
Figure 25:
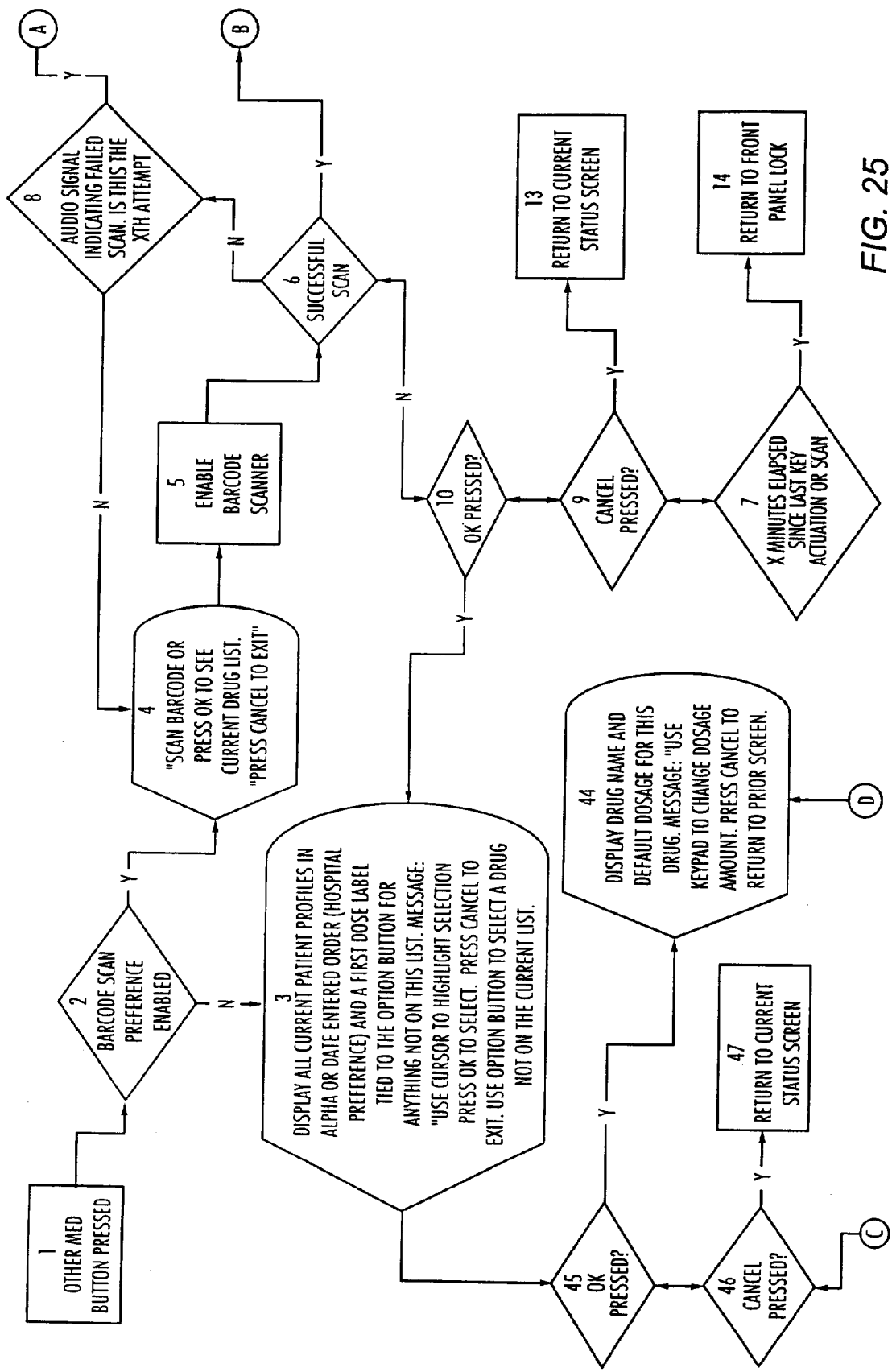
FIGS. 25, 26, 27, and 28 are a flow chart illustrating a non-IV programming routine according to one embodiment of the invention.
Figure 26:
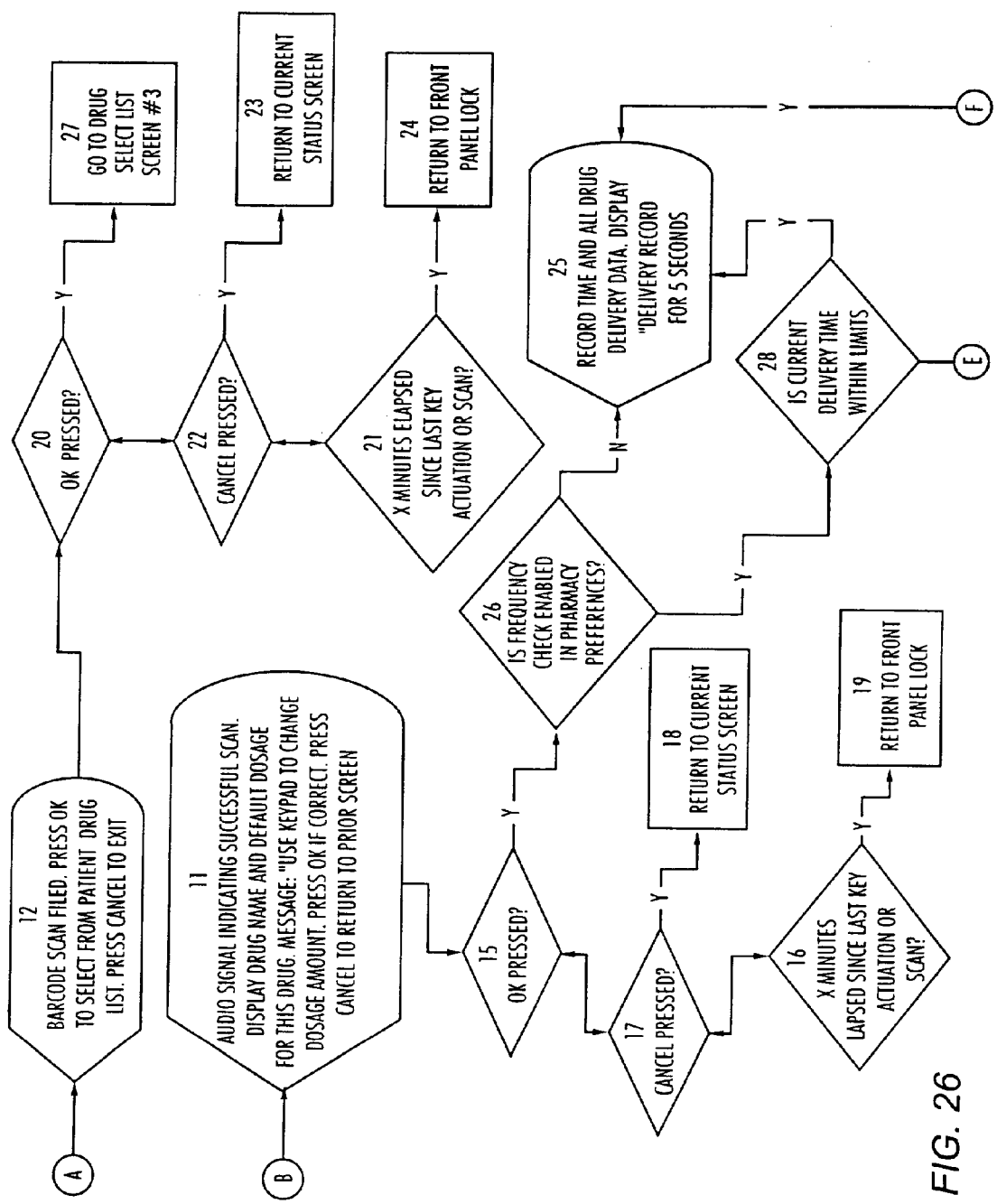
Figure 27:
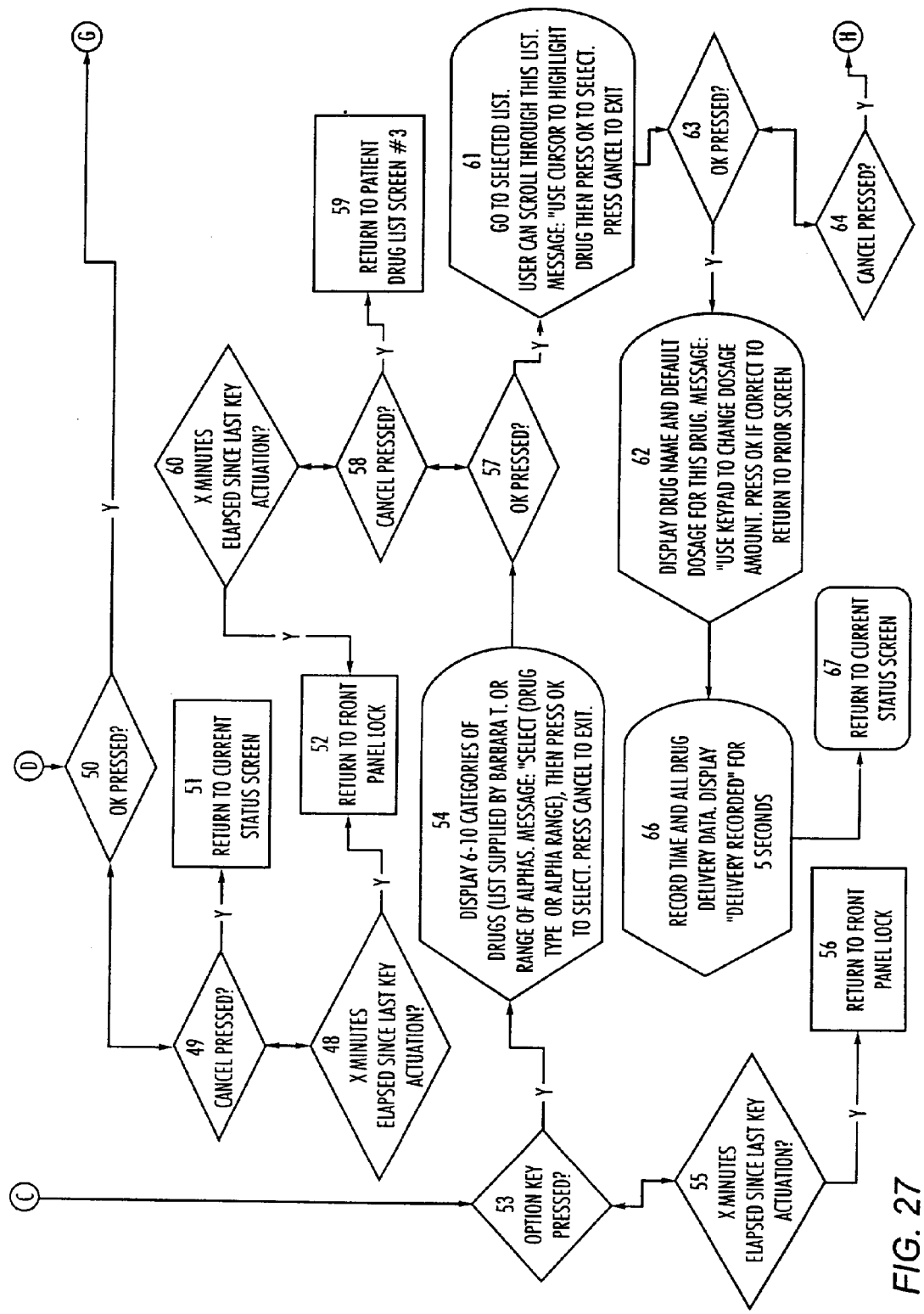
Figure 28:
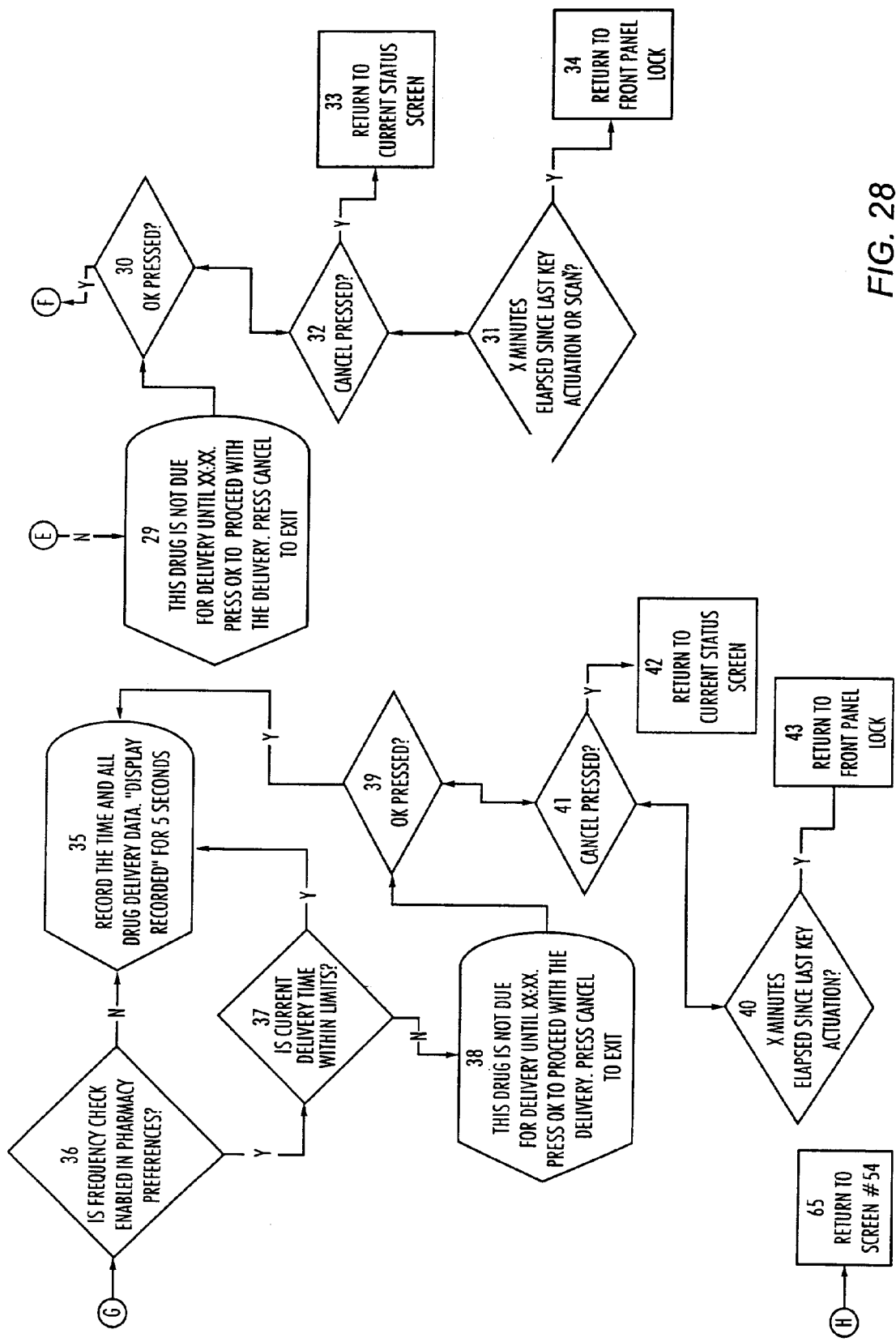
Figure 29A:
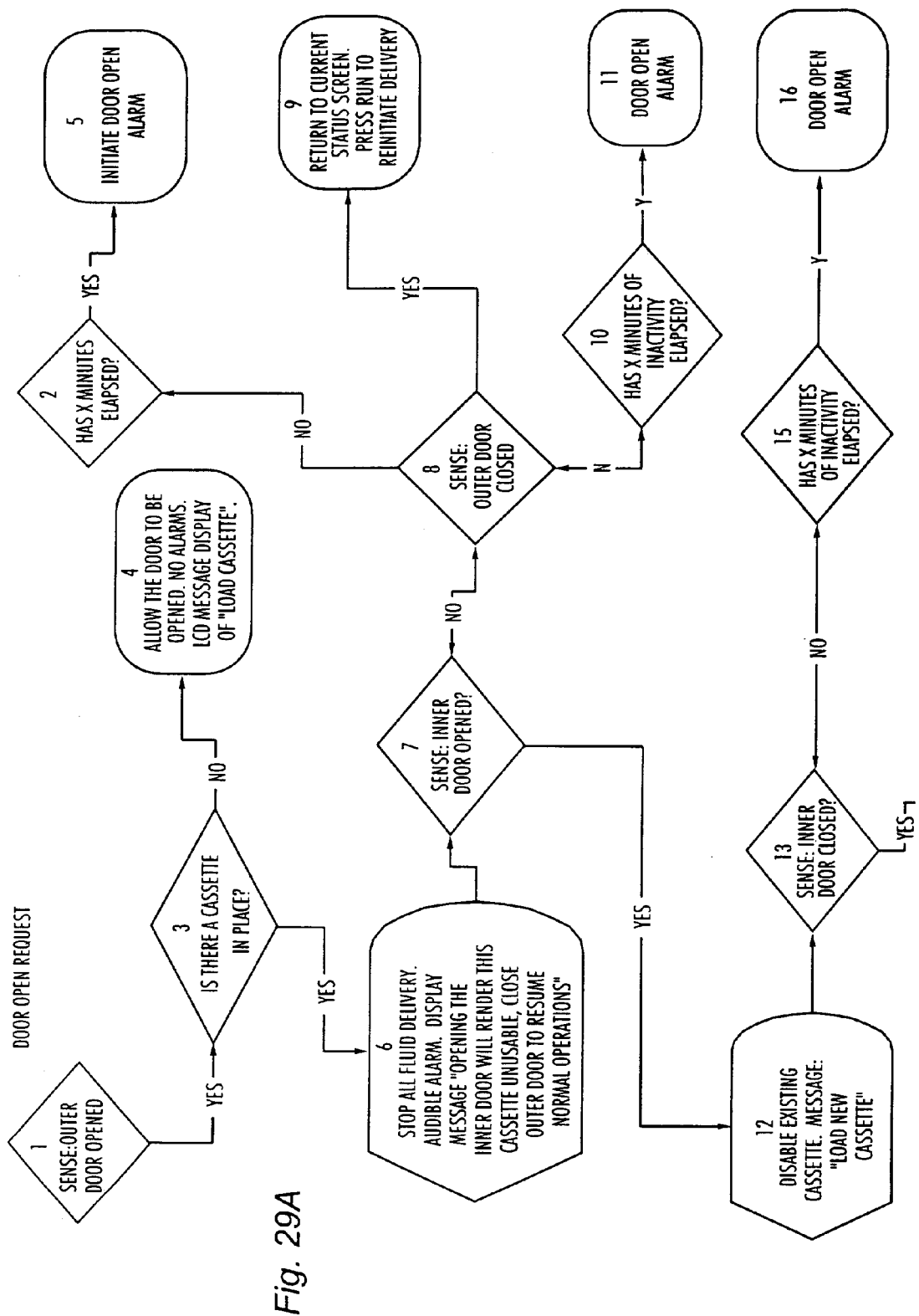
Figure 29B:
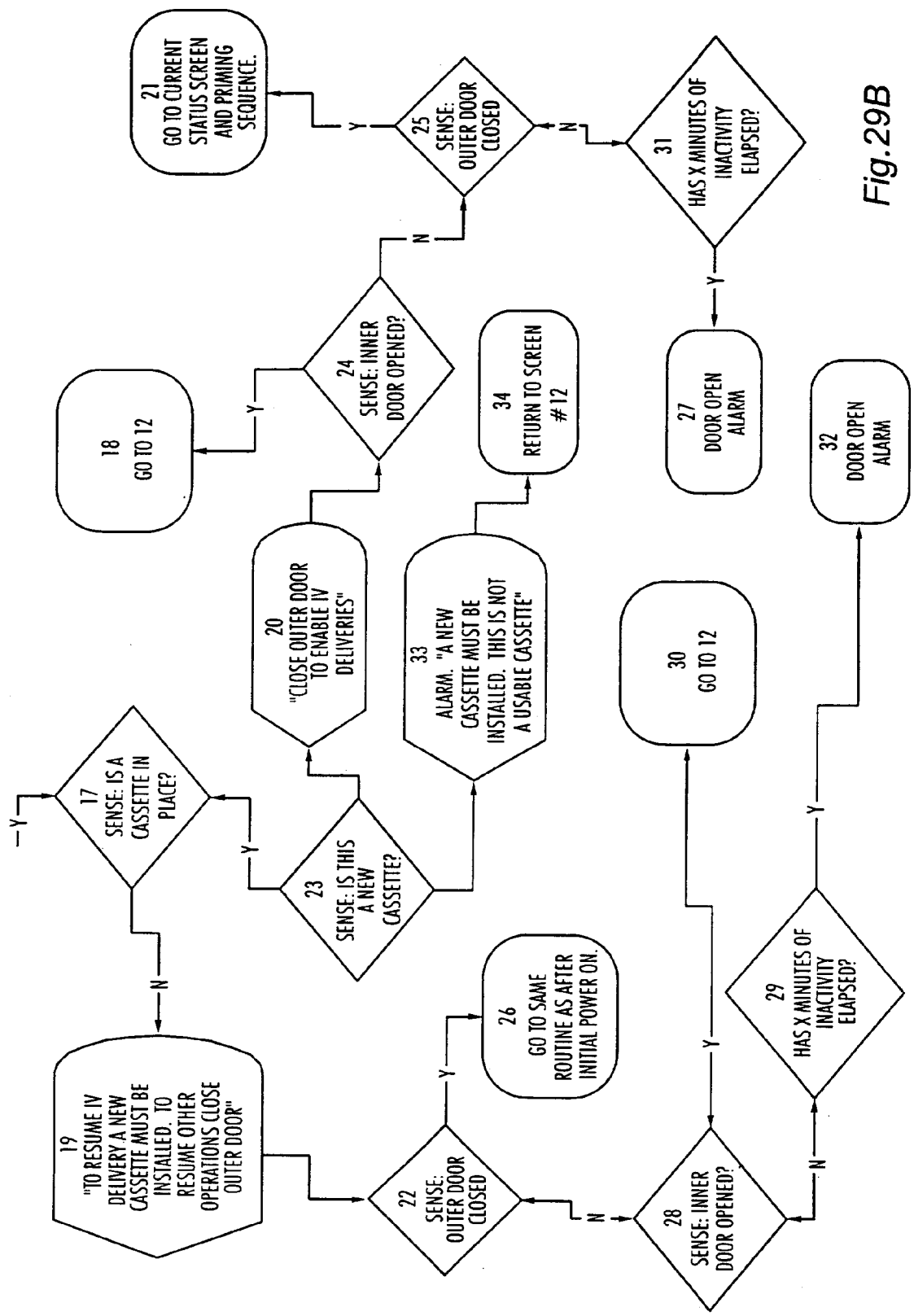
Figure 34:
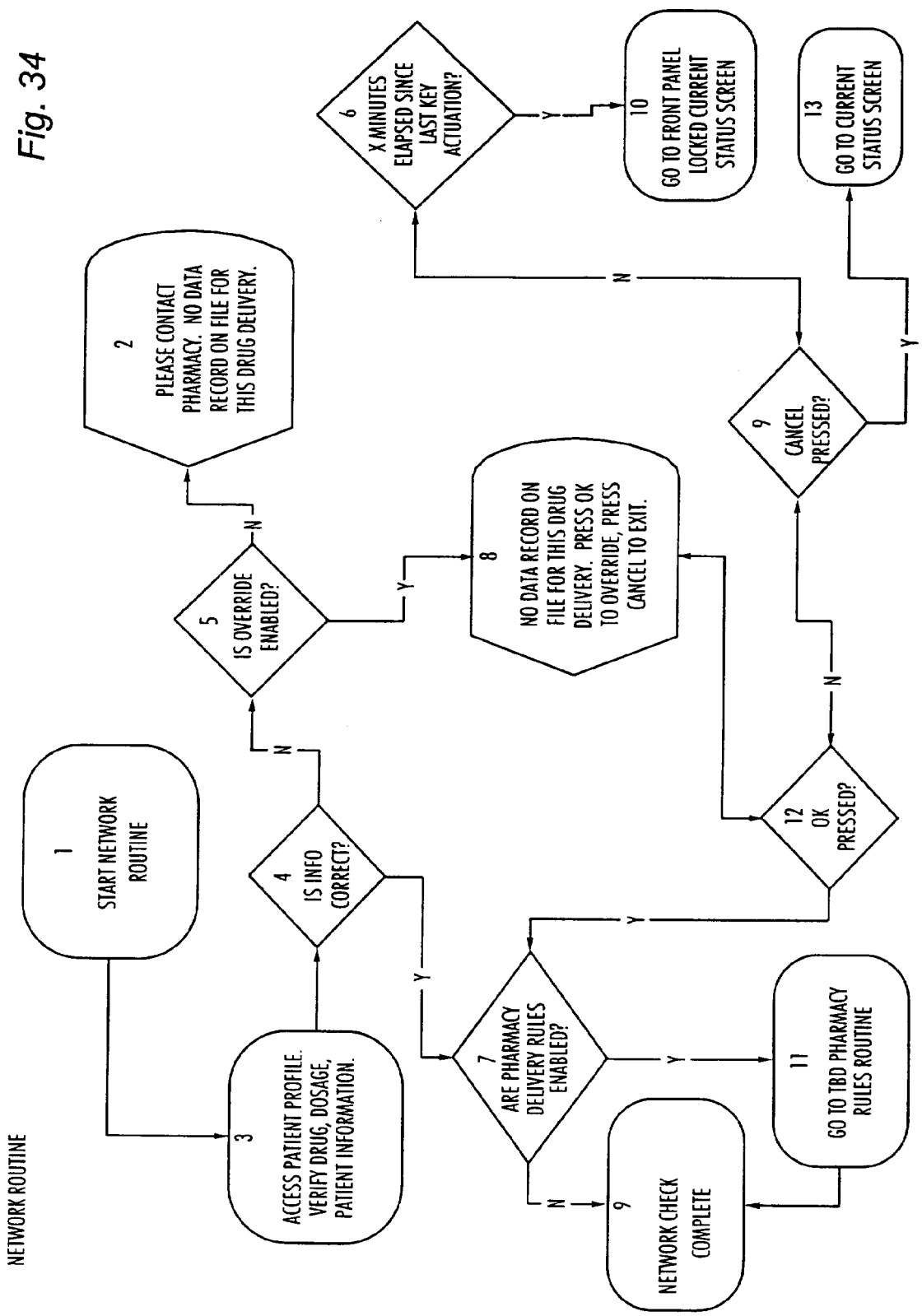
FIG. 34 is a flow chart illustrating a network routine according to one embodiment of the invention.
Figures 1, 35A:
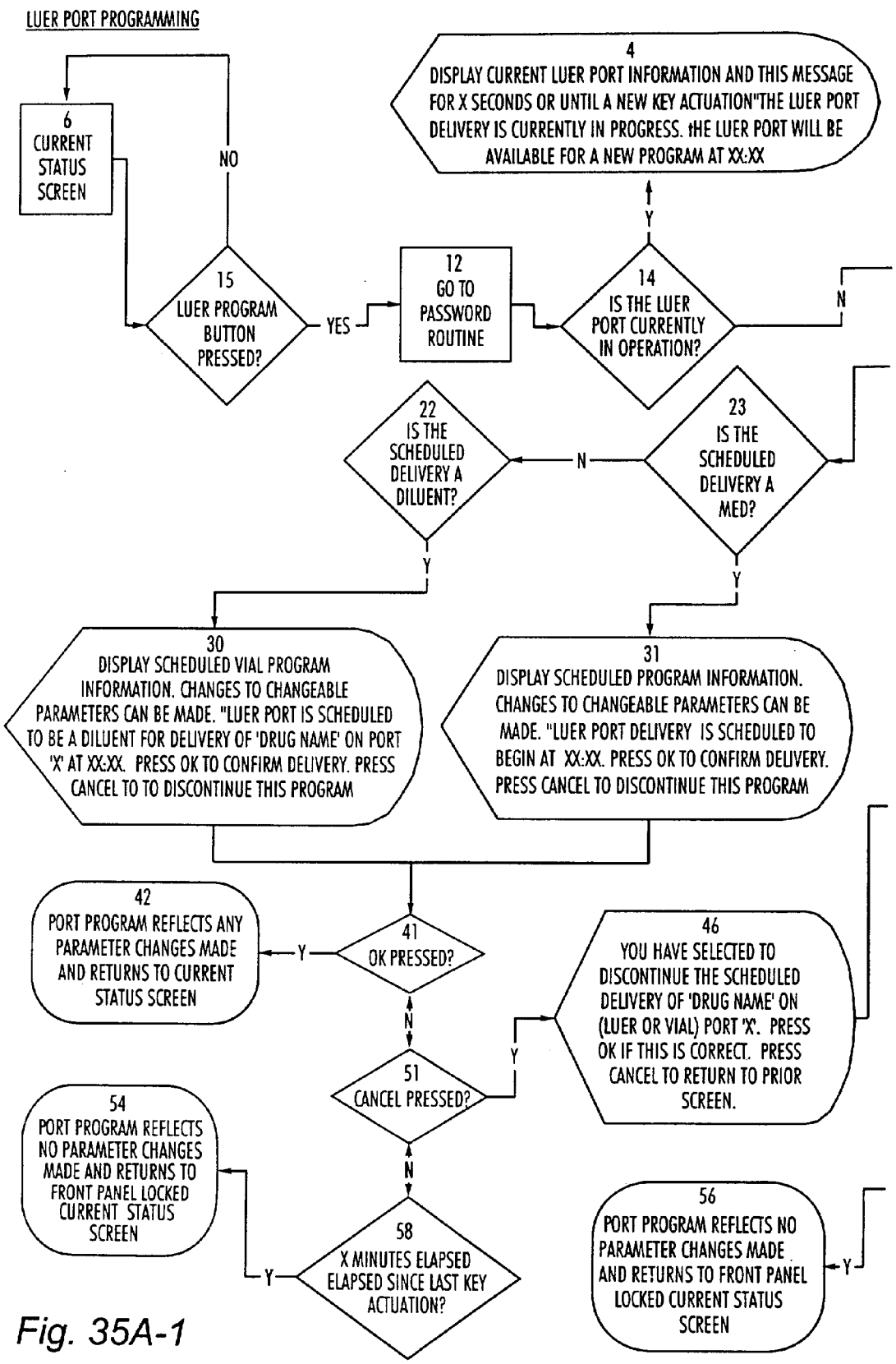
Figures 2, 35A:
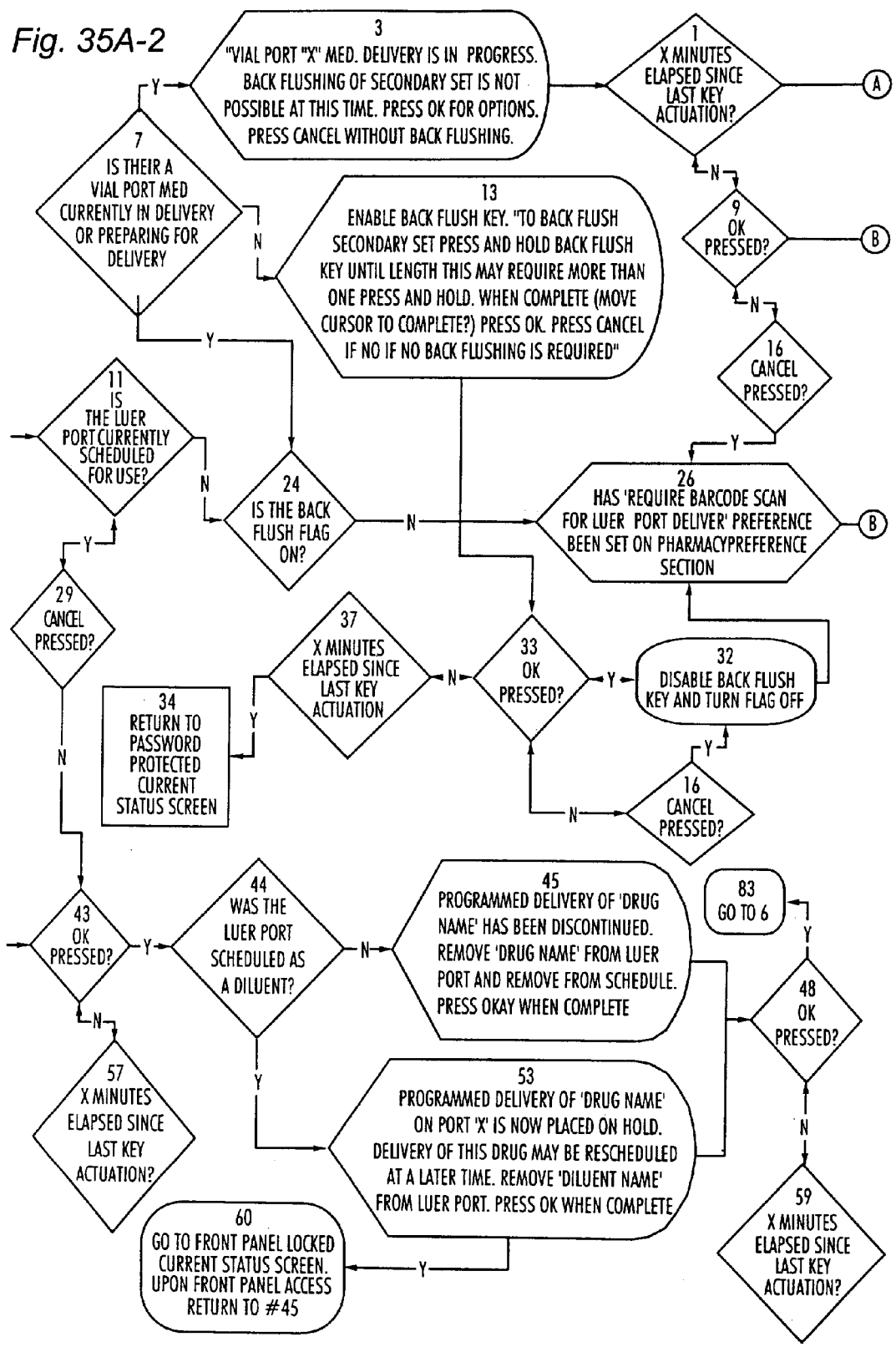
Figure 35B:
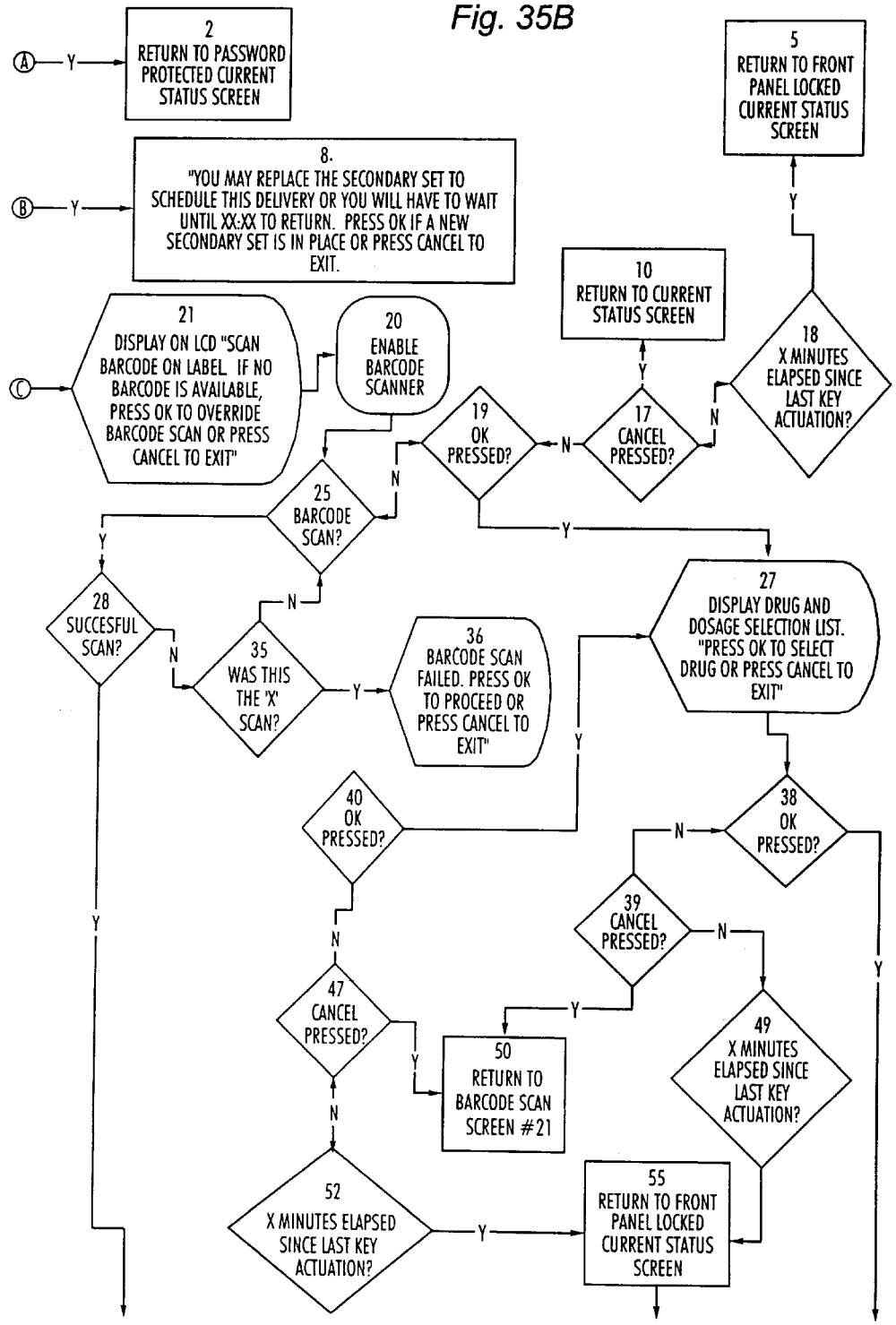
Figure 35:
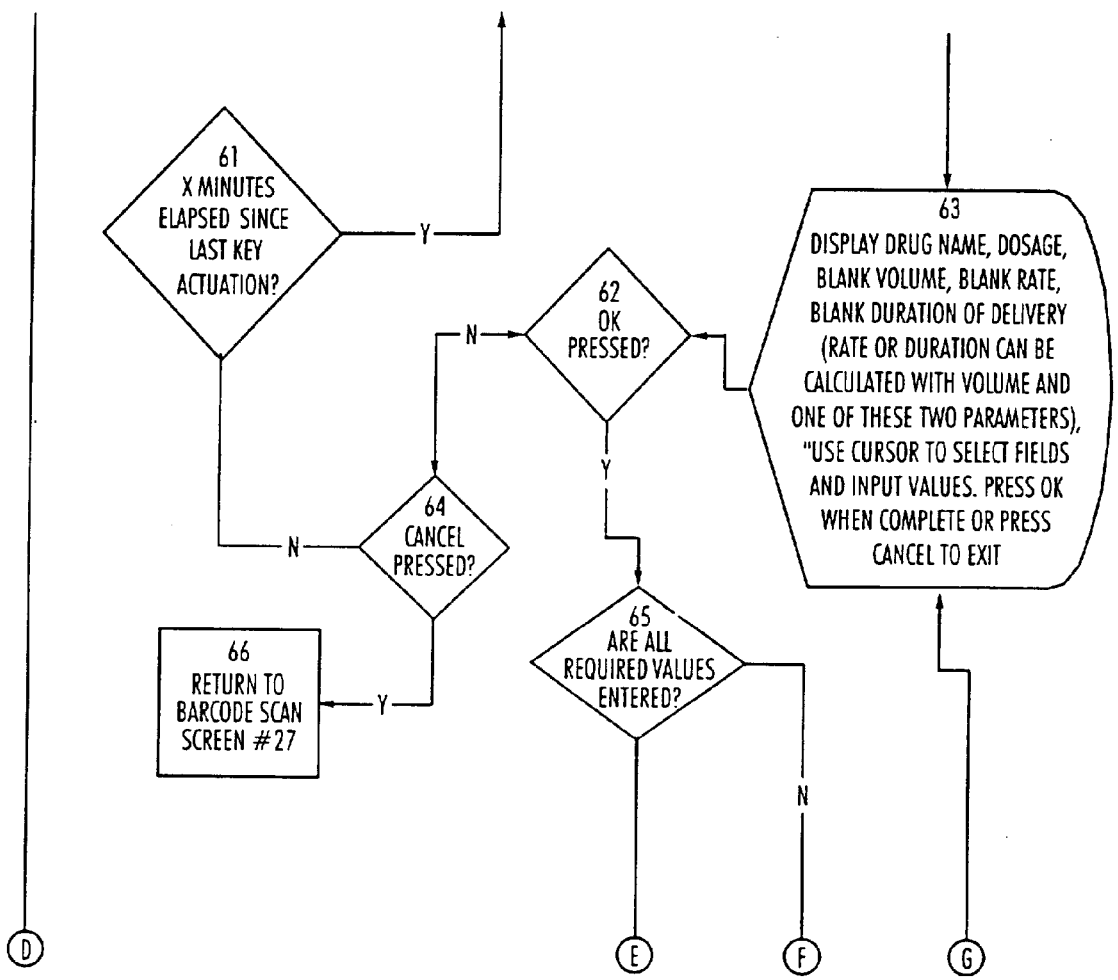
Figure 35C:
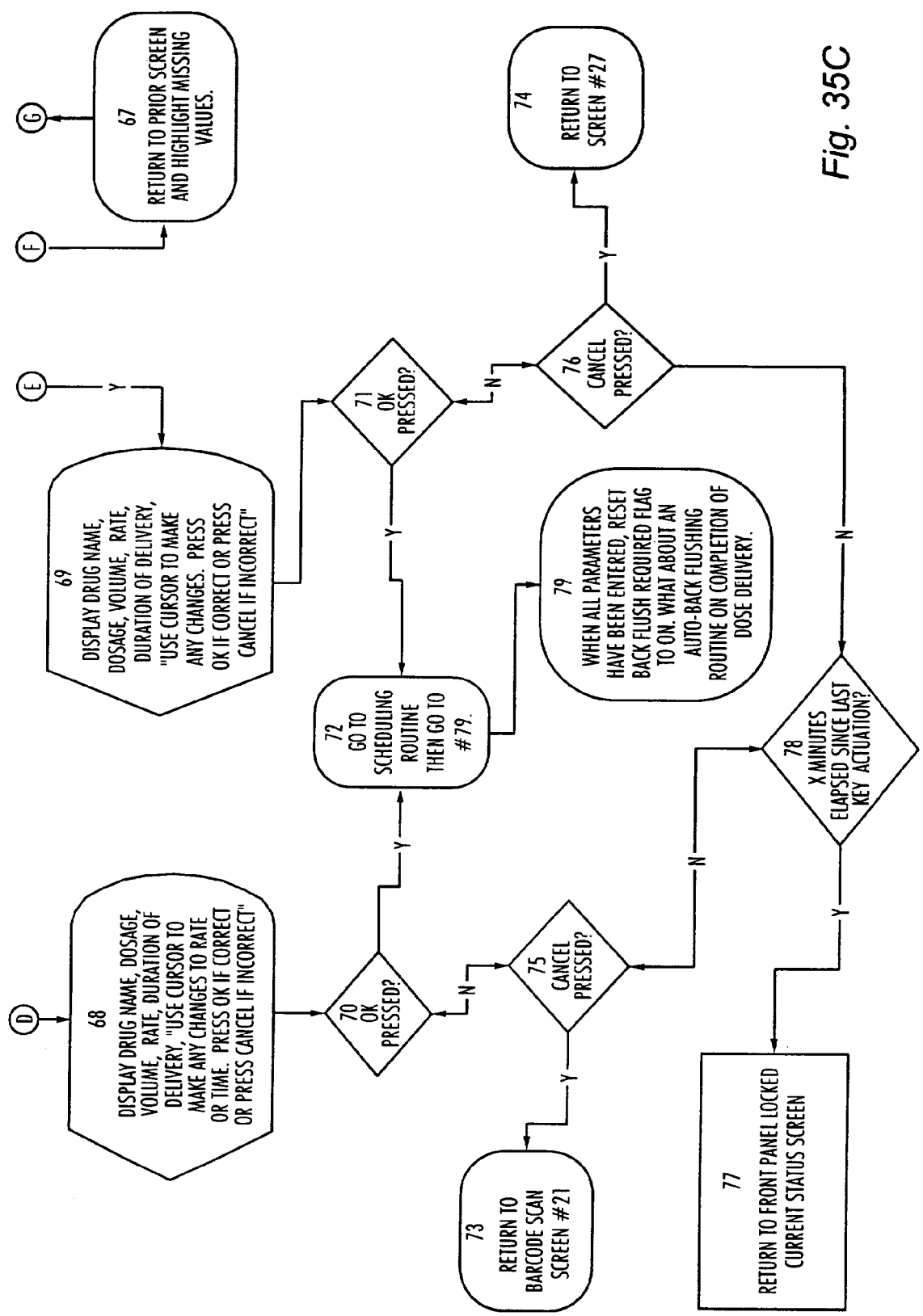

FIG. 34 generally outlines a network routine and checking of the Patient Profile according to one embodiment. The Luer port programming FIGS. 35A, 35B and 35C are a flow chart illustrating a luer port programming routine according to one embodiment of the invention. Flow diagram 35A describes the instrument operation when the L button is pressed on the keypad. This is a similar program to the Vial Port programming except for one difference: There is no reconstitution or dilution done on the Luer port in this embodiment. The Luer port is for use with a pharmacy-prepared admixture that may come in a mini-bag, a syringe or a larger volume container. The instrument would prompt the user to identify the drug by one of the three means mentioned earlier; bar code scanning the label, by pulling the drug name from the Patient Profile List, or going to the larger comprehensive list. The instrument performs the check in the case of the bar code scanned drug or a drug selected from the larger list to make sure that it was the drug for this patient. The drug is scheduled for delivery in a similar fashion as the vial ports.

Whether a vial port or a luer port, after each drug is delivered, the instrument preferably thoroughly rinses the cassette fluid paths, spikes, and in some cases the vials themselves to adequately clear any drug residual that could cause future compatibility problems. In the case of an incompatibility between a drug and solution, the instrument also rinses any incompatible solutions from the cassette prior to beginning the mixing of the drug with the new compatible solution.

The flowcharts illustrated in FIGS. 25–28 are related to the medications that are delivered outside of the automated medication management system unit. These could be oral, topical, eye drops, eardrops, suppositories lotions, and other IV's that are not delivered through automated medication management system 300 in one embodiment. Once the Other Meds button is pressed, the instrument performs the drug identification routine, Patient Profile, and other operations to check for administration of medication. The same checks for correctness of information can occur. Because automated medication management system 300 in this embodiment does not physically prepare these doses for delivery, automated medication management system 300 completes pre-administration verifications and checks and then prompts the user to administer the dose. The instrument then prompts the user to enter the actual dosage delivered, the time of delivery, and any other information pertinent to the delivery which may be useful in a data record. The user may also enter a notation from a predefined list of possible notes. In the case of a non-automated medication management system 300 administered IV, automated medication management system 300 can establish a record for that particular medication as well.

At a later time the user can complete these records by entry into one of the instruments menu selections. In this manner a record can be created for all meds delivered via automated medication management system 300 or external to the automated medication management system 300. The instrument can transmit that record to the various information systems within the health care facility, including, for example, the pharmacy; the admissions, discharges and transfers database, also known as the ADT; the billing information system; or other entity. The capability of creating an electronic Medication Administration Record (MAR) and other useful reports is another key capability. The instrument acts as a data collection point successfully acquiring all the information, at the patient's bedside, necessary to create those reports.

Figure 29:
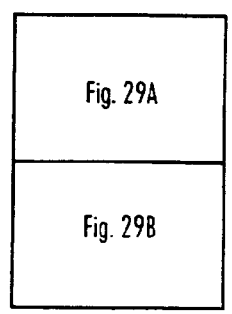
FIG. 29 is a flow chart illustrating door open request routine according to one embodiment of the invention.

FIG. 29 is a flowchart illustrating a process relating to a door open request. Sensors exist on each of the two fluid delivery module doors, the outer and the inner door. If the outer door is opened, the instrument displays a message to the clinician of the consequences of proceeding. If the user does not want to continue opening the door, they could close the outer door and continue normal operations. If they do continue and open the inner door the cassette may be compromised and rendered unusable. As discussed previously, this is a safety feature of the device. When a new cassette is loaded, the instrument senses when the doors are closed, test to verify proper closure, and check if the cassette has been previously compromised.

Figure 30:
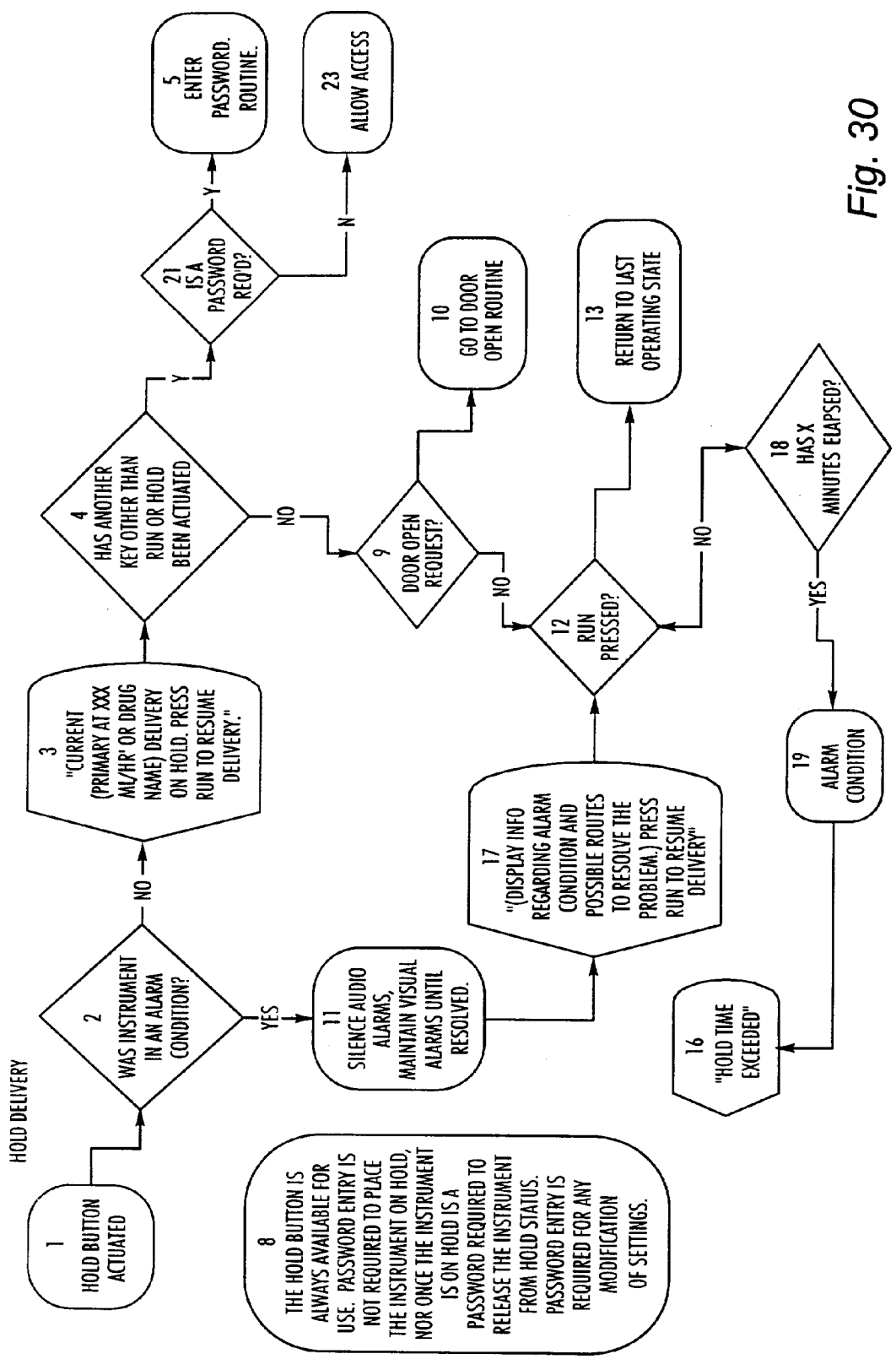
FIG. 30 is a flow chart illustrating a hold delivery routine according to one embodiment of the invention
Figure 31A:
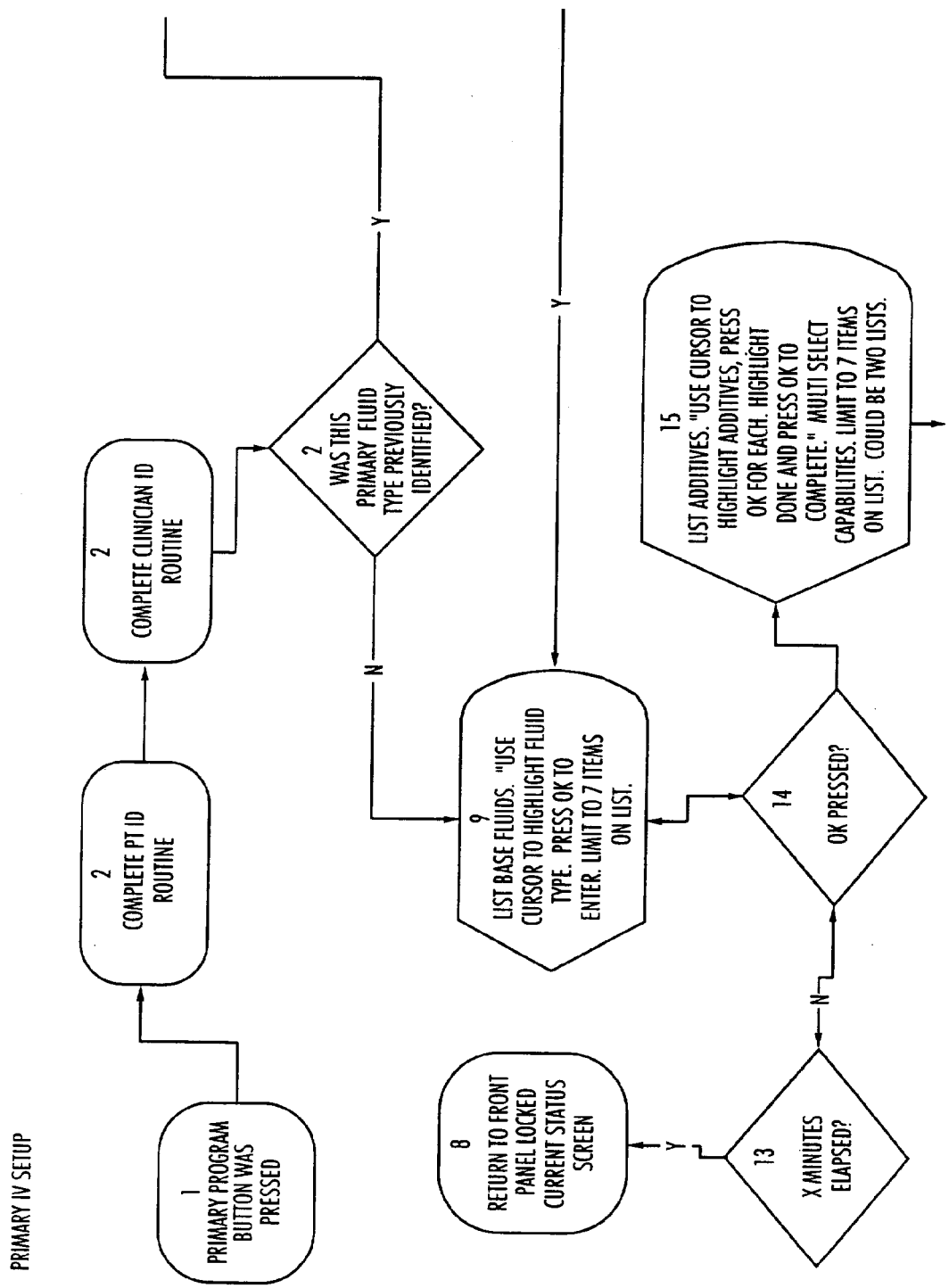
Figure 31B:
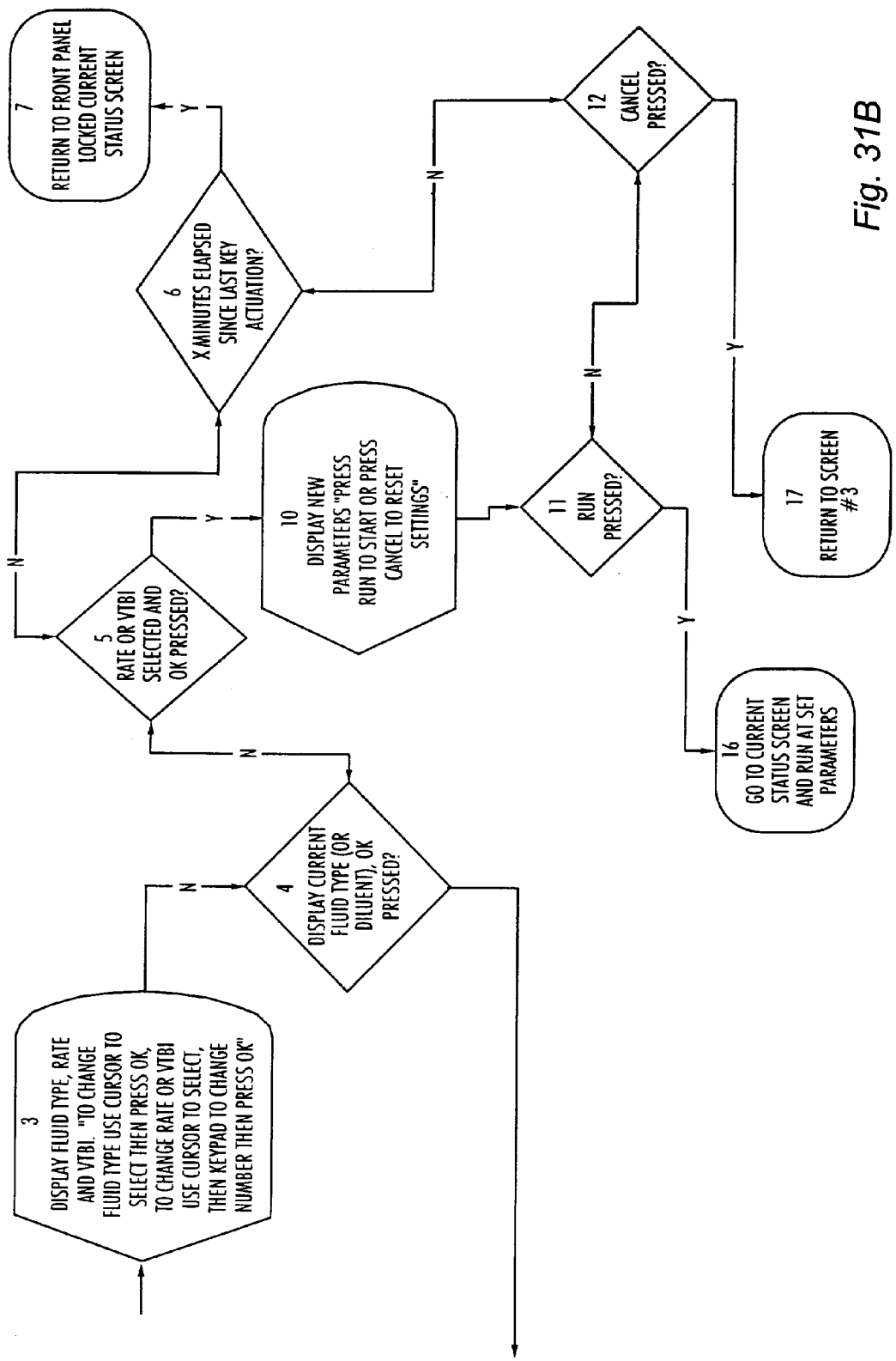
Figure 31C:
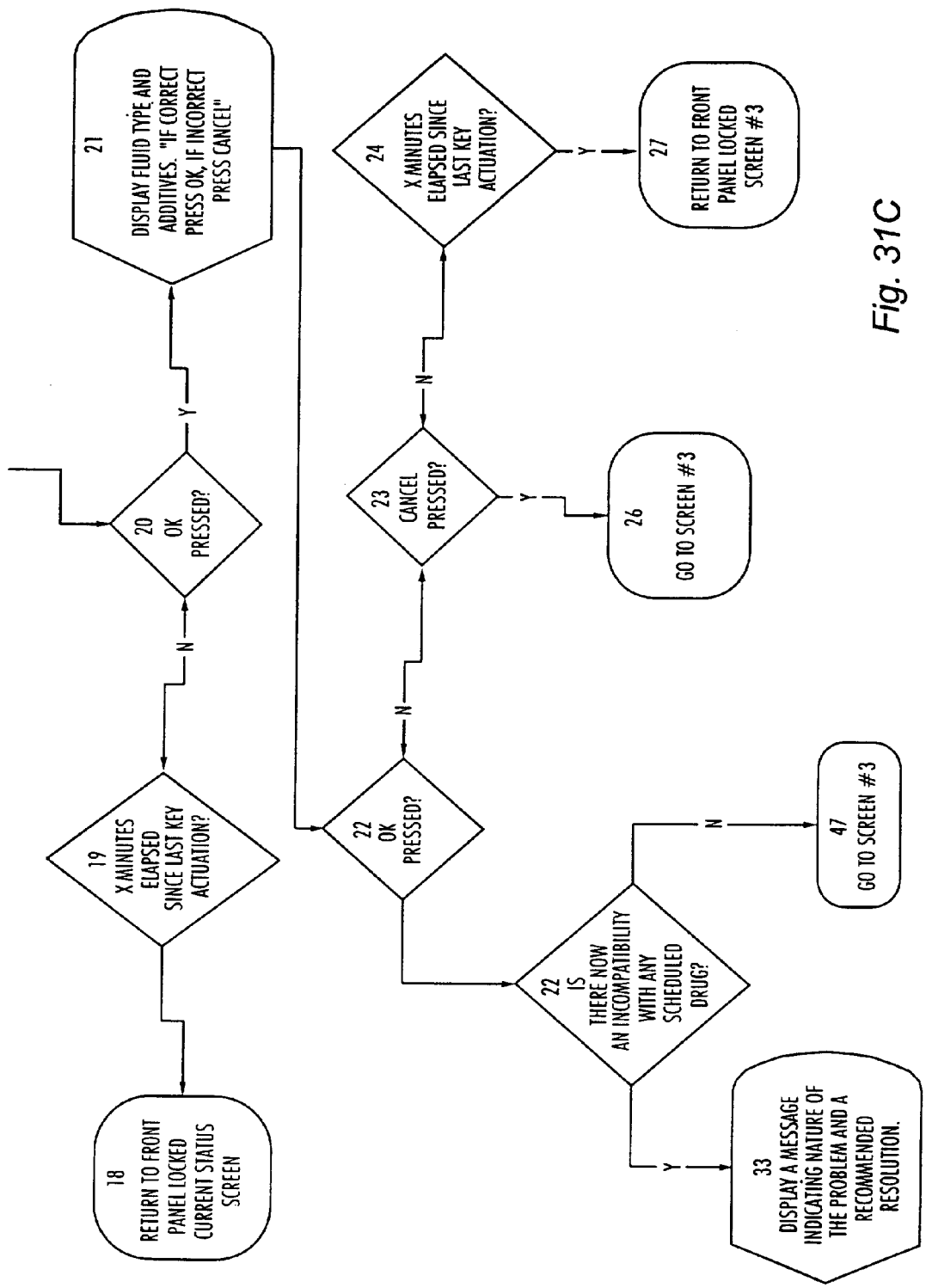
Figures 1, 32A:
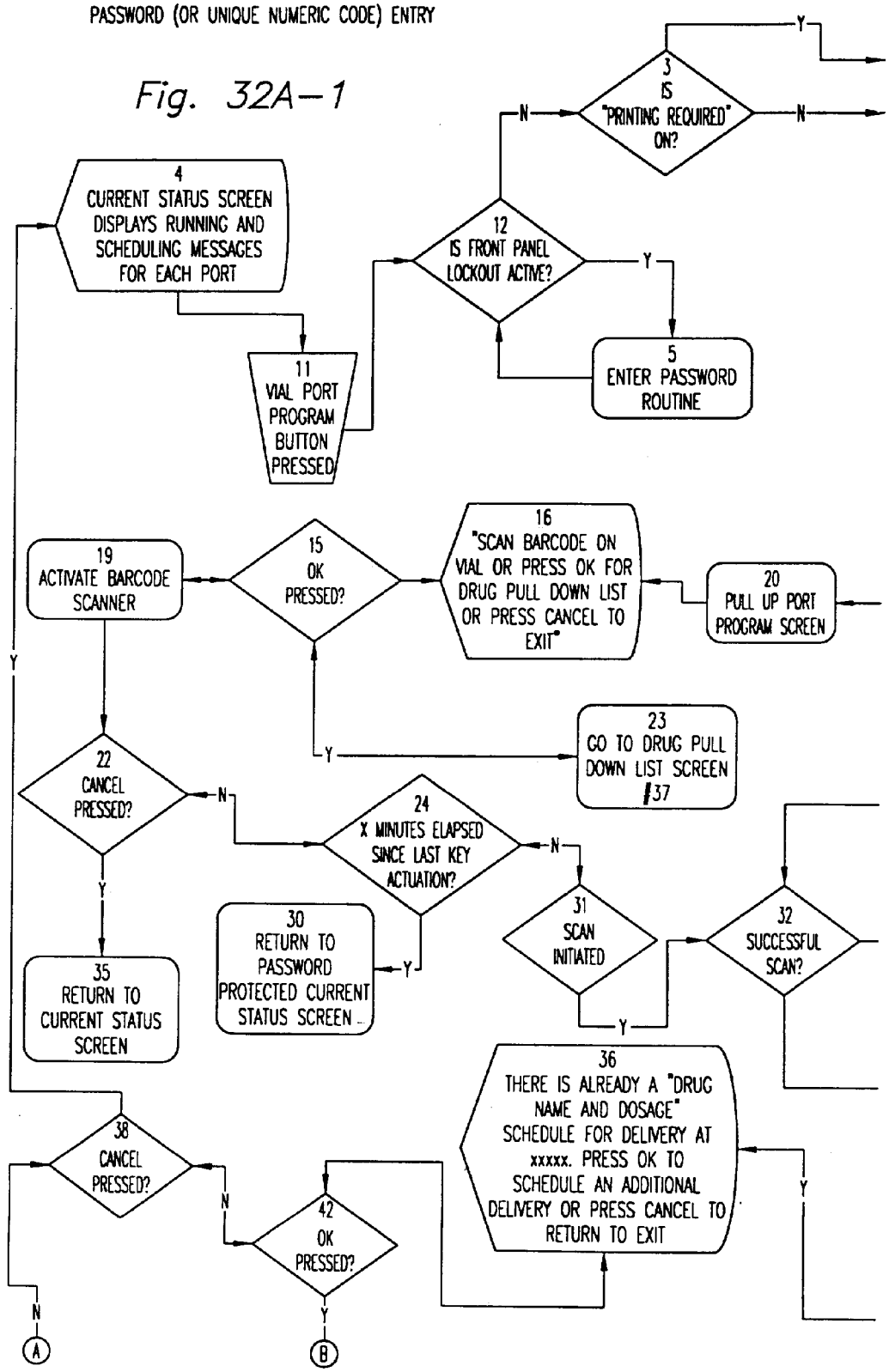
FIG. 1 is a flow chart illustrating a manual admixture and delivery process.
Figures 2, 32A:
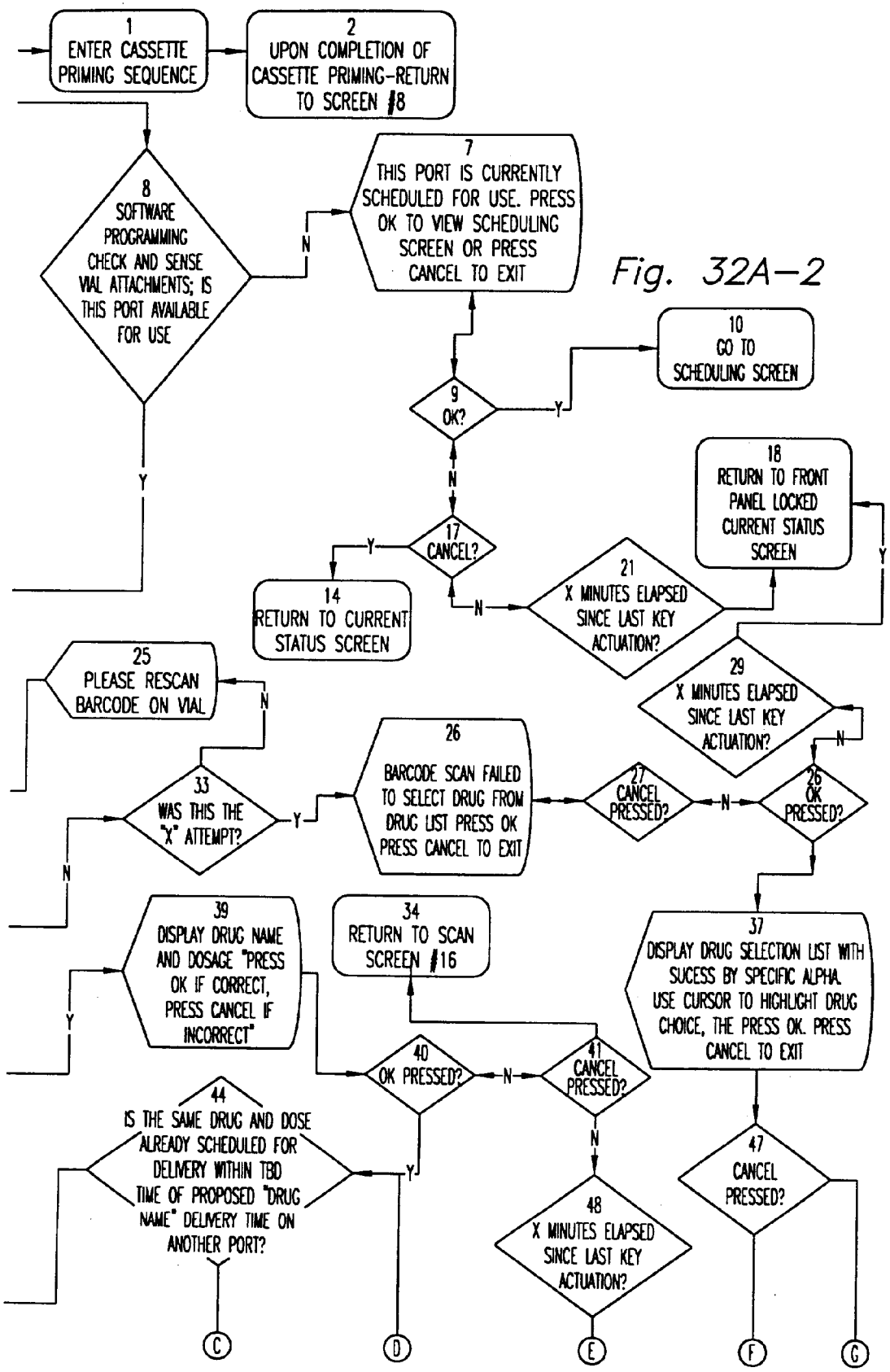
Figures 2, 32B:
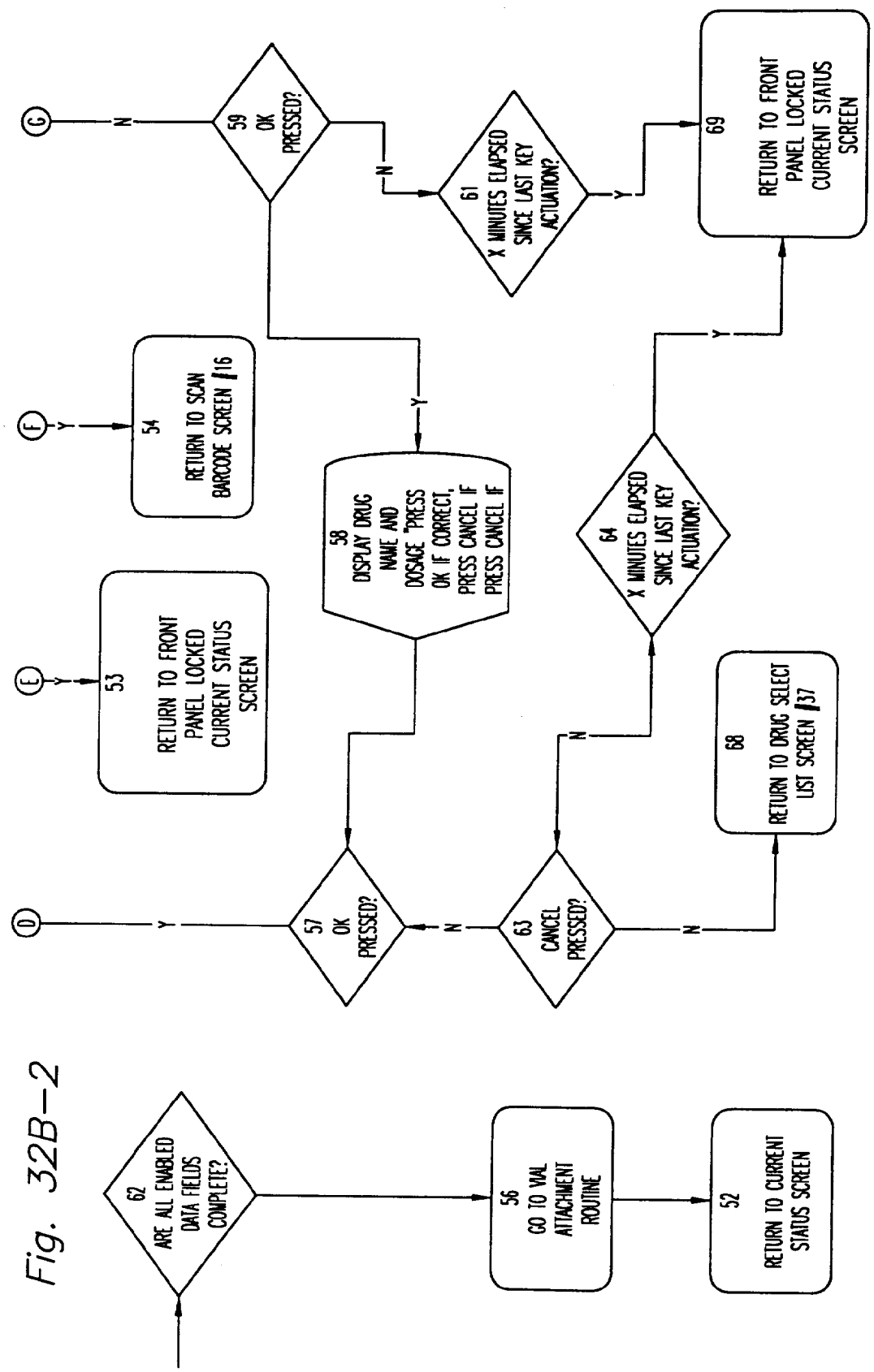
Figure 33A:
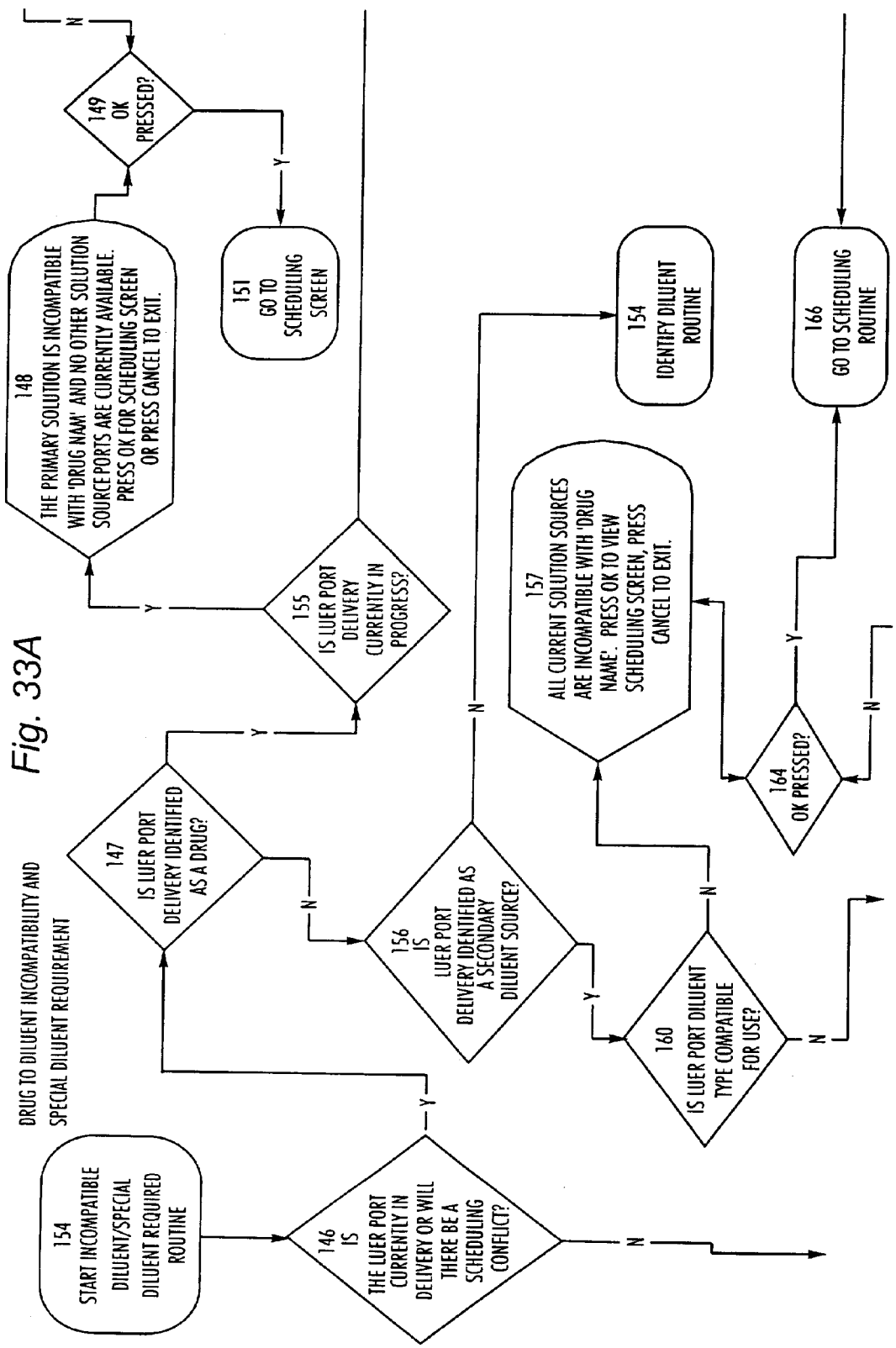
Figure 33B:
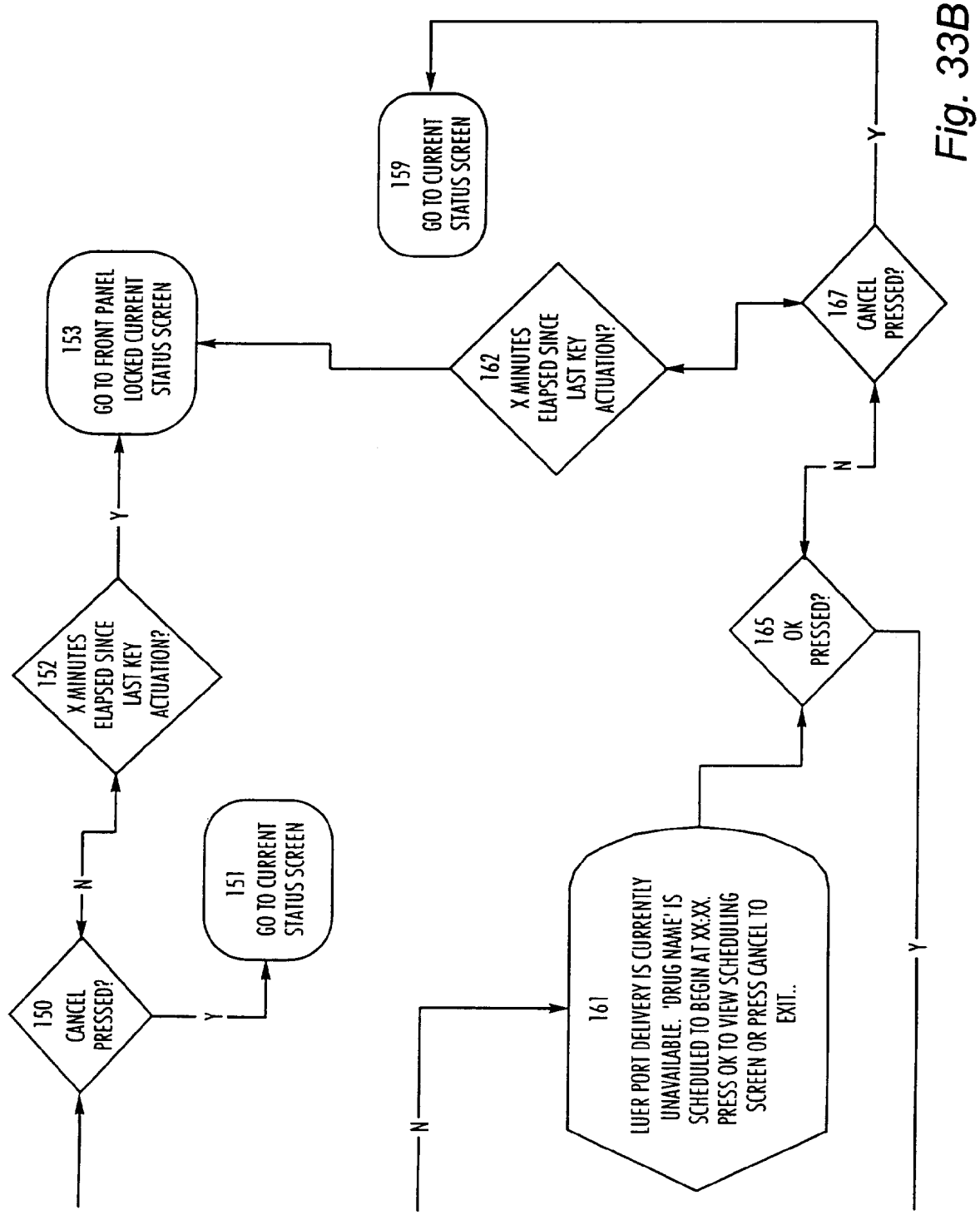
Figure 33C:
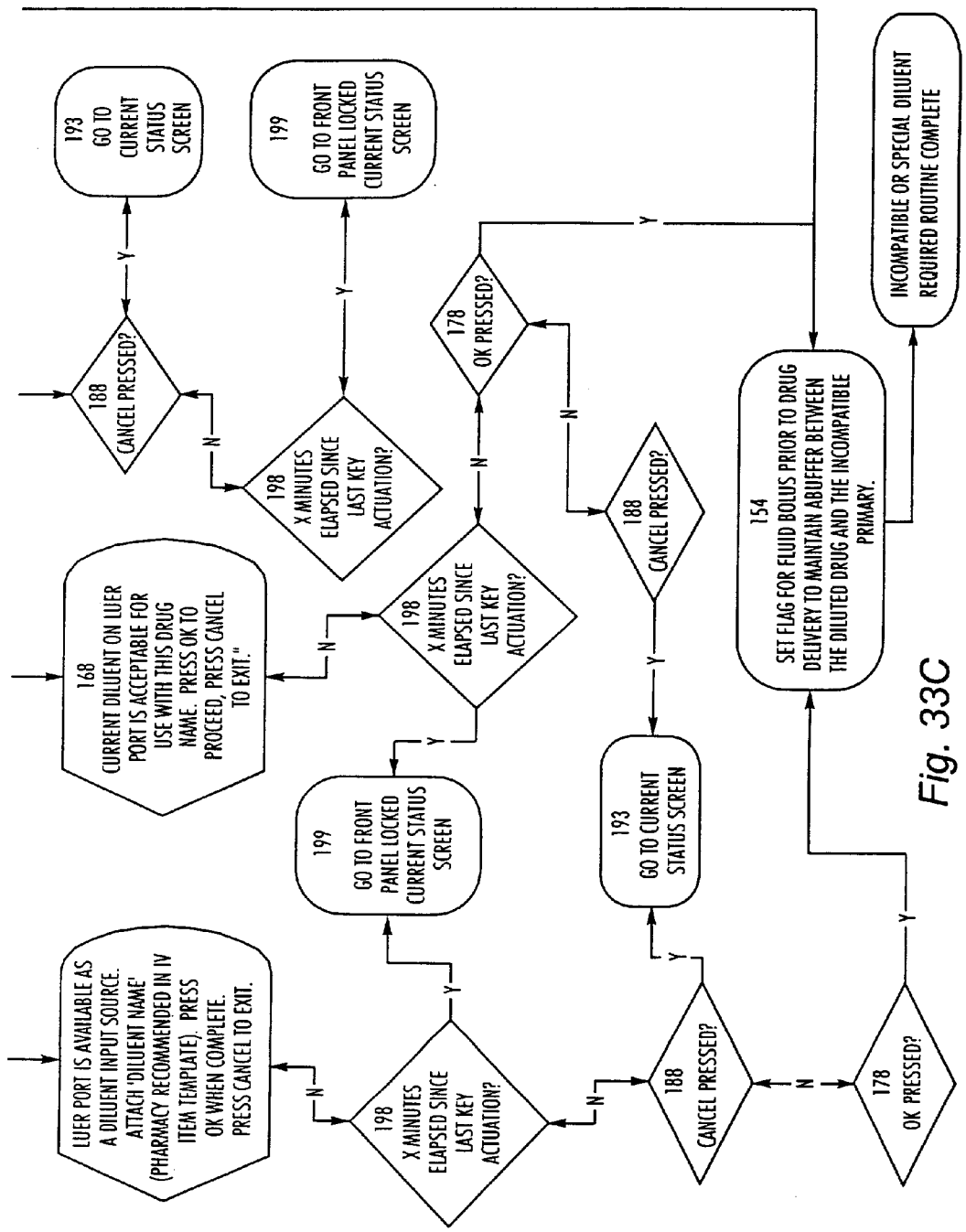

FIG. 30 is a flowchart describing the operation of the Hold/Run button according to one embodiment of the invention. The Hold button is typically a timed function enabling the instrument to be put on hold, stop all fluid delivery operations, at any time during its operation, subject to a typical five minute limitation before it will alarm that the instrument has been on hold too long. The Hold button can be used to silence an alarm condition. By pressing Hold the instrument is placed into a standby mode and the user has a period of time (five minutes in one embodiment) to fix the alarm condition. If the problem is unresolved, the instrument resumes the alarm indicating the hold period has expired. This is a safety feature to ensure that solutions continue to move to the patient and alarms are resolved quickly.

Another feature of the system related to the Hold button is the operation of the Standby button. If the instrument were powered down, there may be no visibility as to whether the cassette doors were opened or closed or vial attachment mechanisms were actuated. By incorporating a standby command, along with the power command, on the keypad, the user is offered a choice of the condition. The default is standby for the instrument, but the user can use the cursor to move down to a power down command and press "OK." If the power down command is chosen, the instrument informs the user of the consequences, such as, for example, loss of the cassette, loss of patient information or loss of the network connection. Upon power up, parameters may need to be reset, including for example patient ID, clinician ID, and so on. Standby mode maintains all the sensors on the doors and all the vial attachment mechanisms to notify users if there were any tampering going on the system would provide warnings and alarms to maintain the system's integrity. The patient's ID is maintained in the standby mode and upon recovery needs to be verified. If there are any drugs previously scheduled on this instrument, the instrument examines the schedule, the current time, and asks the user to help resolve any issues by asking them to either reschedule drugs, to confirm drug deliveries, etc.

In this document, the term database is generally used to refer to one or more data records or a collection of data regarding various types of information or data. This reference, along with any references to specific databases described herein are not intended to require a particular structure or organization of physical or logical databases. As would be apparent to one of ordinary skill in the art after reading this document, varying physical or logical data groupings can be provided in one or more locations or on one or more devices to implement the described databases.

While the embodiments and applications of this invention have been shown and described, and while the best mode contemplated at the present time by the inventors has been described, it should be apparent to those skilled in the art that many more modifications are possible, without departing from the inventive concepts therein. Both product and process claims have been included and in the process claims it is understood that the sequence of some of the claims can vary and still be within the scope of this invention. The invention therefore can be expanded, and is not to be restricted except as defined in the appended claims and reasonable equivalence departing therefrom.

We claim:

1. A vial-loading mechanism for loading a vial onto a spike, comprising:

a support member located adjacent to said spike;

a holding assembly including at least one holder having a holding portion that holds at least one vial, said holder reciprocally mounted to said support member for reciprocal motion in a predefined direction between an unlocked position where the vial does not contact the spike and a locked position where the vial does contact the spike;

means for providing an opposing force when said holding assembly is moved towards the locked position and urging said holding assembly into at least one of said positions; and a locking assembly including a locking arm with a cam, and wherein when said holder assembly is moved towards said locked position, said holder assembly engages said cam so as to cause said locking arm to move laterally away from said holder assembly, and wherein when said holder assembly is provided in said locked position, said locking arm restores itself to a natural position where it retains said holder assembly in said locked position.

2. The vial-loading mechanism of claim 1, wherein said locking arm includes a torsional spring.

3. The vial-loading mechanism of claim 1, wherein said locking arm is made of a resilient material.

4. A vial-loading mechanism for loading a vial onto a spike, comprising:

a holding assembly including a pair of holder arms pivotally connected to each other and each holder arm designed to hold a different size vial, the holding assembly movable in a predefined direction between an unlocked position where the vial does not contact the spike and a locked position where the vial does contact the spike;

means for providing an opposing force when said holding assembly is moved towards the locked position and urging said holding assembly into at least one of said positions; and a locking assembly adapted to lock the holding assembly in at least the locked position.

5. The vial-loading mechanism of claim 4, wherein one holder arm fits inside another.

6. The vial-loading mechanism of claim 5, wherein one holder arm pivots between an out-of-the-way position and an engaged position where the arm is used to hold the vial.

7. A vial-loading mechanism for loading a vial onto a spike, comprising:

a support member located adjacent to the spike;

a holding assembly mounted to said support member so as to be positionable between an unlocked position for loading a vial and a locked position for piercing the vial with a spike, said holding assembly having a first outer holding member for holding a vial;

a second holding assembly pivotally mounted to said first holding member, said second holding assembly having a second inner holding member for holding a second vial which is smaller than the first vial; and a catch having an engagement unit for securing said holding assembly in said locked position.

8. The vial-holding mechanism of claim 7, wherein said holding members have an inner surface which is corrugated.

9. A vial-loading mechanism for loading a vial onto a spike, comprising:

a holding assembly including at least one holder configured to hold more than one different sized vial, the holding assembly movable in a predefined direction between an unlocked position where the vial does not contact the spike and a locked position where the vial does contact the spike; and a locking assembly including a locking arm with a cam, and wherein when said holder assembly is moved towards said locked position, said holder assembly engages said cam so as to cause said locking arm to move laterally away from said holder assembly, and wherein when said holder assembly is provided in said locked position, said locking arm restores itself to a natural position where it retains said holder assembly in said locked position.

10. A vial-loading mechanism for loading a vial onto a spike, comprising:

a holding assembly including a pair of holder arms, each holder arm configured to hold a different sized vial and one holder arm adapted to fit inside another, the holding assembly movable in a predefined direction between an unlocked position where the vial does not contact the spike and a locked position where the vial does contact the spike; and a locking assembly adapted to lock the holding assembly in at least the locked position.

11. The vial-loading mechanism of claim 10, wherein the holder arms are pivotally connected to each other.

12. The vial-loading mechanism of claim 11, wherein one holder arm pivots between an out-of-the-way position and an engaged position where the arm is used to hold the vial.

* * * * *